United States Patent [19]
Stilz et al.

[11] Patent Number: 5,998,447
[45] Date of Patent: Dec. 7, 1999

[54] HETEROCYCLES AS INHIBITORS OF LEUCOCYTE ADHESION AND AS VLA-4 ANTAGONISTS

[75] Inventors: Hans Ulrich Stilz, Frankfurt; Volkmar Wehner, Sandberg; Christoph Huels, Wackernheim; Dirk Seiffge, Mainz-Kostheim, all of Germany

[73] Assignee: Hoechst Aktiengesellschaft AG, Frankfurt, Germany

[21] Appl. No.: 08/972,031

[22] Filed: Nov. 17, 1997

[30] Foreign Application Priority Data

Nov. 15, 1996 [DE] Germany ............................ 196 47 382

[51] Int. Cl.$^6$ .......................... A01N 43/40; A01N 57/16; C07F 9/32; C07D 233/40
[52] U.S. Cl. ........................... 514/341; 514/398; 514/94; 514/89; 546/22; 546/274.4; 548/112; 548/313.7; 548/314.7; 548/319.5
[58] Field of Search ............................ 548/319.5, 314.7, 548/313.7; 546/274.4; 514/341, 398

[56] References Cited

U.S. PATENT DOCUMENTS 5,424,293  6/1995  Zoller et al. ........................ 514/20

FOREIGN PATENT DOCUMENTS

| 580 008 | 1/1994 | European Pat. Off. |
|---|---|---|
| 0 796 855 | 9/1997 | European Pat. Off. |
| WO 93/13798 | 7/1993 | WIPO |
| WO 94/15958 | 7/1994 | WIPO |
| WO 95/14008 | 5/1995 | WIPO |
| WO 95/15973 | 6/1995 | WIPO |
| WO 96/00581 | 1/1996 | WIPO |
| WO 96/06108 | 2/1996 | WIPO |
| WO 96/20216 | 7/1996 | WIPO |
| 96/2296 | 8/1996 | WIPO |

OTHER PUBLICATIONS

Mariano J. Elices, et al., "VCAM–1 on Activated Endothelium Interacts with the Leukocyte Integrin VLA–4 at a Site Distinct from the VLA–4/Fibronectin Binding Site", *Cell*, vol. 60, pp. 577–584, Feb. 1990.

G. Kilger, et al., "Molecular anaylsis of the physiological and pathophysiological role of $\alpha_4$–integrins", *J. Mol. Med: Review*, vol. 73, pp. 347–354, 1995.

Thomas B. Issekutz, et al., "Rat Blood Neutrophils Express Very Late Antigen 4 and it Mediates Migration to Arthritic Joint and Dermal Inflammation", *J. Exp. Med.*, vol. 183, pp. 2175–2184, May 1996.

Bruce N. Cronstein, et al., "The Adhesion Molecules of Inflammation", *Arthritis and Rheumatism*, vol. 36, No. 2, pp. 147–157, Feb. 1993.

*Primary Examiner*—Johann Richter
*Assistant Examiner*—Dominic Keating
*Attorney, Agent, or Firm*—Foley & Lardner

[57] ABSTRACT

Compounds of the formula I

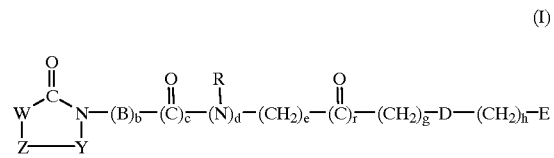

(I)

in which B, D, E, R, W, Y, Z, b, c, d, e, f, g and have the meanings indicated in the claims, are inhibitors of the adhesion and migration of leucocytes and/or antagonists of the adhesion receptor VLA-4 which belongs to the group of integrins. The invention relates to the use of compounds of the formula I, and of pharmaceutical preparations which contain such compounds, for the treatment and prophylaxis of diseases which are caused by an un desired extent of leucocyte adhesion and/or leucocyte migration or which are associated therewith or in which cell—cell or cell-matrix interactions play a part which are based on interactions of VLA-4 receptors with their ligands, for example of inflammatory processes, rheumatoid arthritis or allergic disorders, and it also relates to the use of compounds of the formula I for the production of pharmaceuticals for use in such diseases. It further relates to novel compounds of the formula I.

17 Claims, No Drawings

HETEROCYCLES AS INHIBITORS OF LEUCOCYTE ADHESION AND AS VLA-4 ANTAGONISTS

The present invention relates to compounds of the formula I

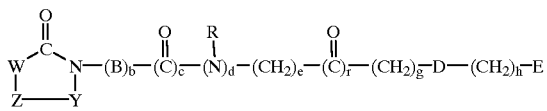

as inhibitors of the adhesion and migration of leucocytes and/or as antagonists of the adhesion receptor VLA-4 which belongs to the group of integrins. The invention relates to the use of compounds of the formula I and of pharmaceutical preparations which contain such compounds for the treatment or prophylaxis of diseases which are caused by an undesired extent of leucocyte adhesion and/or leucocyte migration or which are associated therewith or in which cell—cell or cell-matrix interactions which are based on interactions of VLA-4 receptors with their ligands play a part, for example of inflammatory processes, of rheumatoid arthritis or of allergic disorders, and it also relates to the use of compounds of the formula I for the production of pharmaceuticals for use in such diseases. It further relates to novel compounds of the formula I.

The integrins are a group of adhesion receptors which play an important part in cell—cell-binding and cell-extracellular matrix-binding processes. They have an αβ-heterodimeric structure and exhibit a wide cellular distribution and a high extent of evolutive conservation. The integrins include, for example, the fibrinogen receptor on platelets, which interacts especially with the RGD sequence of fibrinogen, or the vitronectin receptor on osteoclasts, especially with the RGD sequence of fibrinogen, or the vitronectin receptor on osteoclasts, which interacts especially with the RGD sequence of vitronectin or of osteopontin. The integrins are divided into three major groups, the β2 subfamily with the representatives LFA-1, Mac-1 and p150/95, which are responsible i particular for cell—cell interactions of the immune system, and the subfamiles β1 and β3, whose representatives mainly mediate cell adhesion to components of the extracellular matrix (Ruoslahti, Annu. Rev. Biochem. 1988, 57, 375). The integrins of the β1 subfamily, also called VLA proteins (very late (activation) antigen), include at least six receptors which interact specifically with fibronectin, collagen and/or laminin as ligands. Within the VLA family, the integrin VLA-4 (α4 β1) is atypical in so far as it is mainly restricted to lymphoid and myeloid cells and is responsible in these for cell—cell interactions with a large number of other cells. For example, VLA-4 mediates the interaction of T and B lymphocytes with the heparin II-binding fragment of human plasma fibronectin (FN). The binding of VLA-4 with the heparin II-binding fragment of plasma fibronectin is especially based on an interaction with an LDVP sequence. In contrast to the fibrinogen or vitronectin receptor, VLA-4 is not a typical RGD-binding integrin (Kilger and Holzmann, J. Mol. Meth. 1995, 73, 347).

The leucocytes circulating in the blood normally exhibit only a low affinity for the vascular endothelial cells which line the blood vessels. Cytokines which are released from inflamed tissue cause the activation of endothelial cells and thus the expression of a large number of cell surface antigens. These include, for example, the adhesion molecules ELAM-1 (endothelial cell adhesion molecule-1; also designated as E-selectin), which, inter alia, binds neutrophils, ICAM-1 (intercellular adhesion molecule-1), which interacts with LFA-1 (leucocyte function-associated antigen 1) on leucocytes, and VCAM-1 (vascular cell adhesion molecule-1), which binds various leucocytes, inter alia lymphocytes (Osborn et al., Cell 1989, 59, 1203). VCAM-1, like ICAM-1, is a member of the immunoglobulin gene superfamily. VCAM-1 (First known as INCAM-110) was identified as an adhesion molecule which is induced on endothelial cells by inflammatory cytokines such as TNF and IL-1 and lipopolysaccharides (LPS). Elices et al. (Cell 1990, 60, 577) showed that VLA-4 and VCAM-1 form a receptor-ligand pair which mediates the adhesion of lymphocytes to activated endothelium. The binding of VCAM-1 to VLA-4 does not take place here due to an interaction of the VLA-4 with an RGD sequence; such one is not contained in VCAM-1 (Bergelson et al, Current Biology 1995, 5, 615). VLA-4, however, also occurs on other leucocytes, and the adhesion of leucocytes other than lymphocytes is also mediated via the VCAM-1/VLA-4 adhesion mechanism. VLA-4 thus represents an individual example of a β1 integrin receptor which, via the ligands VCAM-1 and fibronectin, plays an important part in cell—cell interactions and in cell-extracellular matrix interactions.

The cytokine-induced adhesion molecules play an important part in the recruitment of leucocytes into extravascular tissue regions. Leucocytes are recruited into inflammatory tissue regions by cell adhesion molecules which are expressed on the surface of endothelial cells and serve as ligands for leucocyte cell surface proteins or protein complexes (receptors) (the terms ligand and receptor can also be used vise versa). Leucocytes from the blood must first adhere to endothelial cells before they can migrate into the synovium. Since VCAM-1 binds to cells which carry the integrin VLA-4 (α4β1), such as eosinophils, T and B lymphocytes, monocytes or also neutrophils, it and the VCAM-1/VLA-4 mechanism have the function of recruiting cells of this type from the blood stream into areas of infection and inflammatory foci (Elices et al., Cell 1990, 60, 577; Osborn, Cell 1990, 62, 3; Issekutz et al., J. Exp. Med. 1996, 183, 2175).

The VCAM-1/VLA-4 adhesion mechanism has been connected with a number of physiological and pathological processes. Apart from cytokine-induced endothelium, VCAM-1 is additionally expressed, inter alia, by the following cells: myoblasts, lymphoid dendritic cells and tissue macrophages, rheumatoid synovium, cytokine-stimulated neural cells, parietal epithelial cells of the Bowman's capsule, the renal tubular epithelium, inflamed tissue during heart and kidney transplant rejection and by intestinal tissue in graft-versus-host disease. VCAM-1 is also found to be expressed on those tissue areas of the arterial endothelium which correspond to early arteriosclerotic plaques of a rabbit model. Additionally, VCAM-1 is expressed on follicular dendritic cells of human lymph nodes and is found on stroma cells of the bone marrow, for example in the mouse. The latter finding points to a function of VCAM-1 in B-cell development. Apart from cells of hematopoietic origin, VLA-4 is also found, for example, on melanoma cell lines, and the VCAM-1/VLD-4 adhesion mechanism is connected with the metastasis of such tumors (Rice et al., Science 1989, 246, 1303).

The main form in which VCAM-1 occurs in vivo on endothelial cells and which is the dominant form in vivo is designated as VCAM-7D and carries seven immunoglobulin domains. The domains 4,5 and 6 are similar in their amino acid sequences to the domains 1,2 and 3. The fourth domain is removed in a further form, consisting of six domains, designated here as VCAM-6D, by alternative splicing. VCAM-6D can also bind VLA-4-expressing cells.

Further details on VLA-4, VCAM-1, integrins and adhesion proteins are found, for example, in the articles by Kiler and Holzmann, J. Mol. Meth. 1995, 73, 347; Elices, Cell Adhesion in Human Disease, Wiley, Chichester 1995, p. 79; Kuijpers, Springer Semin. Immunopathol. 1995, 16, 379.

On account of the role of the VCAM-1/VLA-4 mechanism in cell adhesion processes which are of importance, for example, in infections, inflammations or atherosclerosis, it has been attempted by means of interventions into these adhesion processes to control diseases, in particular, for example, inflammations (Osborn et al., Cell 1989, 59, 1203). A method of doing this is the use of monoclonal antibodies which are directed against VLA-4. Monoclonal antibodies (mAB) of this type which as VLA-4 antagonists block the interaction between VCAM-1 and VLA-4, are known. Thus, for example, the anti-VLA-4 mAB HP2/1 and HP1/3 inhibit the adhesion of VLA-4-expressing Ramos cells (B-cell-like cells) to human umbilical cord endothelial cells and to VCAM-1-transfected COS cells. The anti-VCAM-1 mAB 4B9 likewise inhibits the adhesion of Ramos cells, Jurkat cells (T-cell-like cells) and HL60 cells (granulocyte-like cells) to COS cells transfected with genetic constructs which cause VCAM-6D and VCAM-7D to be expressed. In vitro data with antibodies which are directed against the α4 subunit of VLA-4 show that the adhesion of lymphocytes to synovial endothelial cells is blocked, an adhesion which plays a part in rheumatoid arthritis (van Dinther-Janssen et al., J. Immunol. 1991, 147, 4207).

In vivo experiments have shown that an experimental autoimmune encephalomyelitis can be inhibited by anti-α4 mAB. The migration of leucocytes into an inflammatory focus is likewise blocked by a monoclonal antibody against the α4 chain of VLA-4. The influencing of the VLA-4-dependent adhesion mechanism by antibodies was also investigated in an asthma model in order to investigate the role of VLA-4 in the recruitment of leucocytes in inflamed lung tissue (U.S. Ser. No. 07/821,768; EP-A-626 861). The administration of anti-VLA-4 antibodies inhibited the late-phase reaction and respiratory tract overreaction in allergic sleep.

The VLA-4-dependent cell adhesion mechanism was also investigated in a primate model of inflammatory bowel disease (IBD). In this model, which corresponds to ulcerative colitis in man, the administration of anti-VLA-4 antibodies resulted in a significant reduction in the acute inflammation.

Moreover, it was possible to show that VLA-4-dependent cell adhesion plays a part in the following clinical conditions including the following chronic inflammatory processes: rheumatoid arthritis (Cronstein and Weismann, Arthritis Rheum. 1993, 36, 147; Elices et al., J. Clin. Invest. 1994, 93, 405), diabetes mellitus (Yang et al., Proc. Natl. Acad. Sci. USA 1993, 90, 10494), systemic lupus erythematosus (Takeuchi et al., J. Clin. Invest. 1993, 92, 3008), allergies of the delayed type (type IV allergy) (Elices et al., Clin. Exp. Rheumatol. 1993, 11, p. 77), multiple schlerosis (Yednock et al., Nature 1992, 356, 63), malaria (Ockenhouse et al., J. Exp. Med. 1992, 176, 1183), arteriosclerosis (Obrien et al., J. Clin. Invest. 1993, 92, 945), transplantation (Isobe et al., Transplantation Proceedings 1994, 26, 867–868), various malignancies, for example melanoma (Renkonen et al., Am. J. Pathol. 1992, 140, 763), lymphoma (Freedman et al., Blood 1992, 79, 206) and others (Albelda et al., J. Cell Biol. 1991, 114, 1059).

VLA-4 blocking by suitable antagonists accordingly offers effective therapeutic possibilities, in particular, for example, of treating various inflammatory conditions including asthma and IBD. The particular relevance of VLA-4 antagonists for the treatment of rheumatoid arthritis in this respect results, as already stated, from the fact that leucocytes from the blood must first adhere to endothelial cells before they can migrate into the synovium, and that the VLA-4 receptor plays a part in this adhesion. The fact that VCAM-1 is induced by inflammatory agents on endothelial cells (Osborn, Cell 1990, 62, 3; Stoolman, Cell 1989, 56, 907), and the recruitment of various leucocytes into areas of infection and inflammatory foci has already been dealt with above. In this respect, T cells adhere to activated endothelium mainly via the LFA-1/ICAM-1 and VLA-4/VCAM-1 adhesion mechanisms (Springer, Cell 1994, 76, 301). On most synovial T cells, the binding capacity of VLA-4 for VCAM-1 is increased in rheumatoid arthritis (Popstigo et al., J. Clin. Invest. 1992, 89, 1445). Additionally, an increased adhesion of synovial T cells to fibronectin has been observed (Laffon et al., J. Clin. Invest. 1991, 88, 546; Morales-Ducret et al., J. Immunol. 1992, 149, 1424). VLA-4 is also upregulated both in the course of its expression and with respect to its function on T lymphocytes of the rheumatoid synovial membrane. The blocking of the binding of VLA-4 to its physiological ligands VCAM-1 and fibronectin makes possible an effective prevention or alleviation of articular inflammatory processes. This is also confirmed by experiments with the antibody HP2/1 on Lewis rats with adjuvant arthritis, in which an effective prevention of illness has been observed (Barbadillo et al., Springer Semin. Immunopathol. 1995, 16, 427). VLA-4 is thus an important therapeutic target molecule.

The abovementioned VLA-4 antibodies and the use of antibodies as VLA-4 antagonists are described in the Patent Applications WO-A-93/13798, WO-A-93/15764, WO-A-94/16094, WO-A-94/17828 and WO-A-95/19790. In the Patent Applications WO-A-94/15958, WO-A-95/15973, WO-A-96/00581, WO-A-96/06108 and WO-A-96/20216, peptide compounds are described as VLA-4 antagonists. The use of antibodies and peptide compounds as pharmaceuticals, however, is afflicted with disadvantages, for example lack of oral availability, easy degradability or immunogenic action on longer-tern use, and there is thus a need for VLA-4 antagonists having a favorable profile of properties for use in therapy and prophylaxis.

WO-A-95/14008 describes substituted 5-membered ring heterocycles which have an amino, amidino or guanidino function at the N-terminal end of the molecule and which exhibit platelet aggregation-inhibiting activity. The German Patent Application 19635522.2 describes further heterocycles which are inhibitors of bone resorption. Indications that the compounds covered by the German patent Application 19635522.2 are VLA-4 antagonists or inhibit leucocyte adhesion are not found there, however. Surprisingly, it has now been found that compounds covered by the German Patent Application 19635522.2 also inhibit leucocyte adhesion and are VLA-4 antagonists.

The present invention thus relates to the use of compounds of the formula I

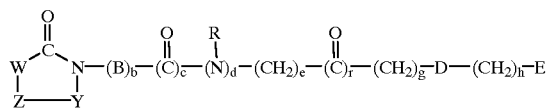

(I)

in which

W is $R^1$—A—($R^{13}$) or $R^1$—A—CH=C;

Y is a carbonyl, thiocarbonyl or methylene group;

Z is N($R^0$), oxygen, sulfur or a methylene group;

A is a bivalent radical from the group consisting of $C_1$–$C_6$-alkylene, ($C_3$–$C_{12}$)-cycloalkylene, ($C_1$–$C_6$)-alkylene-($C_3$–$C_{12}$)-cycloalkyl, phenylene, phenylene-($C_1$–$C_6$)-alkyl, ($C_1$–$C_6$)-alkylenephenyl, ($C_1$–$C_6$)-alkylenephenyl-($C_1$–$C_6$)-alkyl, phenylene-($C_2$–$C_6$)-alkenyl or a bivalent radical of a 5- or 6-membered saturated or unsaturated ring which can contain 1 or 2 nitrogen atoms and can be mono- or disubstituted by ($C_1$–$C_6$)-alkyl or doubly bonded oxygen or sulfur;

B is a bivalent radical from the group consisting of ($C_1$–$C_6$)-alkylene, ($C_2$–$C_6$-alkenylene, phenylene, phenylene-($C_1$–$C_3$)-alkyl, ($C_1$–$C_3$)-alkylenephenyl, where the bivalent ($C_1$–$C_6$)-alkylene radical can be unsubstituted or substituted by a radical from the group consisting of ($C_1$–$C_8$)-alkyl, ($C_2$–$C_8$)-alkyl, ($C_2$–$C_8$)-alkynyl, ($C_3$–$C_{10}$)-cycloalkyl, ($C_3$–$C_{10}$)-cycloalkyl-($C_1$–$C_6$)-alkyl, optionally substituted ($C_6$–$C_{14}$)-aryl, ($C_6$–$C_{14}$)-aryl-($C_1$–$C_6$)-alkyl optionally substituted in the aryl radical, optionally substituted heteroaryl and heteroaryl-($C_1$–$C_6$)-alkyl optionally substituted in the heteroaryl radical;

D is C($R^2$)($R^3$), N($R^3$) or CH=C($R^3$);

E is tetrazolyl, ($R^8$O)$_2$P(O), HOS(O)$_2$, $R^9$NHS(O)$_2$ or $R^{10}$CO;

R is hydrogen, ($C_1$–$C_8$)-alkyl, ($C_3$–$C_{12}$)-cycloalkyl, ($C_3$–$C_{12}$)-cycloalkyl-($C_1$–$C_8$)-alkyl, optionally substituted ($C_6$–$C_{14}$)-aryl, ($C_6$–$C_{14}$)-aryl-($C_1$–$C_8$)-alkyl optionally substituted in the aryl radical, optionally substituted heteroaryl or heteroaryl-($C_1$–$C_8$)-alkyl optionally substituted in the heteroaryl radical, where alkyl radicals can be mono- or polysubstituted by fluorine;

$R^0$ is hydrogen, ($C_1$–$C_8$)-alkyl, ($C_3$–$C_{12}$)-cycloalkyl, ($C_3$–$C_{12}$)-cycloalkyl-($C_1$–$C_8$)-alkyl, ($C_6$–$C_{12}$)-bicycloalkyl, ($C_6$–$C_{12}$)-bicycloalkyl-($C_1$–$C_8$)-alkyl, ($C_6$–$C_{12}$)-tricycloalkyl, ($C_6$–$C_{12}$)-tricycloalyl-($C_1$–$C_8$)-alkyl, optionally substituted ($C_6$–$C_{14}$)-aryl, ($C_6$–$C_{14}$)-aryl-($C_1$–$C_8$)-alkyl optionally substituted in the aryl radical, optionally substituted heteroaryl, heteroaryl-($C_1$–$C_8$)-alkyl optionally substituted in the heteroaryl radical CHO, ($C_1$–$C_8$)-alkyl—CO, ($C_3$–$C_{12}$)-cycloalkyl—CO, ($C_3$–$C_{12}$)-cycloalkyl-($C_1$–$C_8$)-alkyl—CO, ($C_6$–$C_{12}$)-bicycloalkyl—CO, ($C_6$–$C_{12}$)-bicycloalkyl-($C_1$–$C_8$)-alkyl—CO, ($C_6$–$C_{12}$)-tricycloalkyl—CO, ($C_6$–$C_{12}$)-tricycloalkyl-($C_1$–$C_8$)-alkyl-CO, optionally substituted ($C_6$–$C_{14}$)-aryl—CO, ($C_6$–$C_{14}$)-aryl-($C_1$–$C_8$)-alkyl—CO optionally substituted in the aryl radical, optionally substituted heteroaryl—CO, heteroaryl-($C_1$–$C_8$)-alkyl—CO optionally substituted in the heteroaryl radical, ($C_1$–$C_8$)-alkyl—S(O)$_n$, ($C_3$–$C_{12}$)-cycloalkyl—S(O)$_n$, ($C_3$–$C_{12}$)-cycloalkyl-($C_1$–$C_8$)-alkyl-S(O)$_n$, ($C_6$–$C_{12}$)-bicycloalkyl—S(O)$_n$, ($C_6$–$C_{12}$)-bicycloalkyl-($C_1$–$C_8$)-alkyl—S(O)$_n$, ($C_6$–$C_{12}$)-tricycloalkyl—S(O)$_n$, ($C_6$–$C_{12}$)-tricycloalkyl-($C_1$–$C_8$)-alkyl—S(O)$_n$, optionally substituted ($C_6$–$C_{14}$)-aryl—S(O)$_n$, ($C_6$–$C_{14}$)-aryl-($C_1$–$C_8$)-alkyl—S(O)$_n$ optionally substituted in the aryl radical, optionally substituted heteroaryl—S(O)$_n$ or heteroaryl-($C_1$–$C_8$)-alkyl—S(O)$_n$ optionally substituted in the heteroaryl radical, where n is 1 or 2;

$R^1$ is hydrogen, ($C_1$–$C_{10}$)-alkyl, which can optionally be mono substituted or polysubstituted by fluorine, ($C_3$–$C_{12}$)-cycloalkyl, ($C_3$–$C_{12}$)-cycloalkyl-($C_1$–$C_8$)-alkyl, optionally substituted $R^{21}$—(($C_6$–$C_{14}$)-aryl), ($R^{21}$-(($C_6$–$C_{14}$)-aryl))-($C_1$–$C_8$)-alkyl, optionally substituted in the aryl radical, the radical Het-, Het-($C_1$–$C_8$)-alkyl or one of the radicals $R^{21}$O-, $R^{22}$O—NH—, $R^{21}$O—N($R^{23}$)-, $R^{24}$NH—, $R^{25}$N($R^{25}$)-, HO—(($C_1$–$C_8$)-alkyl—N($R^{26}$)-, $R^{27}$C(O)—NH—, $R^{21}$C(O)—N($R^{23}$)-, $R^{21}$C(O)-, $R^{21}$O—C(O)—, $R^{28}$N($R^{21}$)—C(O)—, $R^{21}$O—N=, O= and S=;

$R^2$ is hydrogen, ($C_1$–$C_8$)-alkyl, optionally substituted ($C_6$–$C_{14}$)-aryl-($C_1$–$C_8$)-alkyl optionally substituted in the aryl radical or ($C_3$–$C_8$)-cycloalkyl;

$R^3$ is hydrogen, ($C_1$–$C_8$)-alkyl, optionally substituted ($C_6$–$C_{14}$)-aryl, ($C_6$–$C_{14}$)-aryl-($C_1$–$C_8$)-alkyl optionally substituted in the aryl radical, ($C_3$–$C_8$)-cycloalkyl, ($C_2$–$C_8$)-alkenyl, ($C_2$–$C_8$)-alkynyl, ($C_2$–$C_8$)-alkenylcarbonyl, ($C_2$–$C_8$)-alkynylcarbonyl, pyridyl, $R^{11}$NH, $R^4$CO, COOR$^4$, CON(CH$_3$)R$^4$, CONHR$^4$, CSNHR$^4$, COOR$^{15}$, CON(CH$_3$)R$^{15}$ or CONHR$^{15}$;

$R^4$ is hydrogen or ($C_1$–$C_{28}$)-alkyl which can optionally be mono- or polysubstituted by identical or different radicals from the group consisting of hydroxyl, hydroxycarbonyl, aminocarbonyl, mono- or di-(($C_1$–$C_{18}$)-alkyl)aminocarbonyl, amino-($C_2$–$C_{18}$)-alkylaminocarbonyl, amino-($C_1$–$C_3$)-alkylphenyl-($C_1$–$C_3$)-alkylaminocarbonyl, ($C_1$–$C_{18}$)-alkylcarbonylamino-($C_1$–$C_3$)-alkylphenyl-($C_1$–$C_3$)-alkylaminocarbonyl, ($C_1$–$C_{18}$)-alkylcarbonylamino-($C_2$–$C_{18}$)-alkylaminocarbonyl, ($C_6$–$C_{14}$)-aryl,($C_1$–$C_8$)-alkoxycarbonyl which can also be substituted in the aryl radical, amino, mercapto, ($C_1$–$C_{18}$)-alkoxy, ($C_1$–$C_{18}$)-alkoxycarbonyl, optionally substituted ($C_3$–$C_8$)-cycloalkyl, HOS(O)$_2$—($C_1$–$C_3$)-alkyl, $R^9$NHS(O)$_2$—($C_1$–$C_3$)-alkyl, ($R^8$O)$_2$P(O)—($C_1$–$C_3$)-alkyl, tetrazolyl-($C_1$–$C_3$)-alkyl, halogen, nitro, trifluoromethyl or the radical $R^5$;

$R^5$ is optionally substituted ($C_6$–$C_{14}$)-aryl, ($C_6$–$C_{14}$)-aryl-($C_1$–$C_8$)-alkyl optionally substituted in the aryl radical, a mono- or bicyclic 5- to 12-membered heterocyclic ring which can be aromatic, partially hydrogenated or completely hydrogenated and which can contain one, two or three identical or different heteroatoms from the group consisting of nitrogen, oxygen and sulfur, a radical $R^6$ or a radical $R^6$CO—, where the aryl radical and, independently thereof, the heterocyclic radical can be mono- or polysubstituted by identical or different radicals from the group consisting of ($C_1$–$C_{18}$)-alkyl, ($C_1$–$C_{18}$)-alkoxy, halogen, nitro, amino and trifluoromethyl;

$R^6$ is $R^7R^8$N, $R^7$O or $R^7$S or an amino acid side chain, a natural or unnatural amino acid, imino acid, optionally N—($C_1$–$C_8$)-alkylated or N-(($C_6$–$C_{14}$)-aryl-($C_1$–$C_8$)-alkylated) azaamino acid or a dipeptide radical which can also be substituted in the aryl radical and/or reduced in the peptide bond to —NH—CH$_2$—, and their esters and amides, where hydrogen or hydroxymethyl can optionally stand in place of free functional groups and/or where free functional groups can be protected by protective groups customary in peptide chemistry;

$R^7$ is hydrogen, ($C_1$–$C_{18}$)-alkyl, ($C_6$–$C_{14}$)-aryl-($C_1$–$C_8$)-alkyl, ($C_1$–$C_{18}$)-alkylcarbonyl, ($C_1$–$C_{18}$)-alkoxycarbonyl, ($C_6$–$C_{14}$)-arylcarbonyl, ($C_6$–$C_{14}$)-aryl-($C_1$–$C_8$)-alkylcarbonyl or ($C_6$–$C_{14}$)-aryl-($C_1$–$C_{18}$)-alkyloxycarbonyl, where the alkyl groups can optionally be substituted by an amino group and/or where the aryl radicals can be mono- or polysubstituted, preferably monosubstituted, by identical or different radicals from the group consisting of $(C_1-C_8)$-alkyl, $(C_1-C_8)$-alkoxy, halogen, nitro, amino and trifluoromethyl, or is a natural or unnatural amino acid, imino acid, optionally N—$(C_1-C_8)$-alkylated or N-$((C_6-C_{14})$-aryl-$(C_1-C_8)$-alkylated) azaamino acid or a dipeptide radical which can also be substituted in the aryl radical and/or reduced in the peptide bond to —NH—CH$_2$—;

$R^8$ is hydrogen, $(C_1-C_{18})$-alkyl, optionally substituted $(C_6-C_{14})$-aryl or $(C_6-C_{14})$-aryl-$(C_1-C_8)$-alkyl which can also be substituted in the aryl radical;

$R^9$ is hydrogen, aminocarbonyl, $(C_1-C_{18})$-alkylaminocarbonyl, $(C_3-C_8)$-cycloalkylaminocarbonyl, optionally substituted $(C_6-C_{14})$-arylaminocarbonyl, $(C_1-C_{18})$-alkyl, optionally substituted $(C_6-C_{14})$-aryl or $(C_3-C_8)$-cycloalkyl;

$R^{10}$ is hydroxyl, $(C_1-C_{18})$-alkoxy, $(C_6-C_{14})$-aryl-$(C_1-C_8)$-alkoxy which can also be substituted in the aryl radical, optionally substituted $(C_6-C_{14})$-aryloxy, amino or mono- or di$((C_1-C_{18})$-alkyl)amino;

$R^{11}$ is hydrogen, $(C_1-C_{18})$-alkyl, $R^{12}CO, R^{12a}CS$, optionally substituted $(C_6-C_{14})$-aryl—S(O)$_2$, $(C_1-C_{18})$-alkyl—S(O)$_2$, $(C_6-C_{14})$-aryl-$(C_1-C_8)$-alkyl optionally substituted in the aryl radical, $R^9NHS(O)_2$ or the radical $R^{15}$;

$R^{12}$ is hydrogen, $(C_1-C_{18})$-alkyl, $(C_2-C_8)$-alkenyl, $(C_2-C_8)$-alkynyl, optionally substituted $(C_6-C_{14})$-aryl, $(C_1-C_{18})$-alkoxy, $(C_6-C_{14})$-aryl-$(C_1-C_8)$-alkoxy which can also be substituted in the aryl radical, optionally substituted $(C_6-C_{14})$-aryloxy, the radical $R^{15}$, the radical $R^{15}$—O—, amino, mono- or di-$((C_1-C_{18})$-alkyl)amino, $(C_2-C_8)$-alkenylamino, $(C_2-C_8)$-alkynylamino, $(C_3-C_{12})$-cycloalkylamino, $(C_3-C_{12})$-cycloalkyl-$(C_1-C_8)$-alkylamino, the radical $R^{15}$—NH—, optionally substituted $(C_6-C_{14})$-aryl—NH, $(C_6-C_{14})$-aryl-$(C_1-C_8)$-alkyl—NH which can also be substituted in the aryl radical, optionally substituted heteroaryl—NH or heteroaryl-$(C_1-C_8)$-alkyl—NH optionally substituted in the heteroaryl radical;

$R^{12a}$ is amino, mono- or di-$((C_1-C_{18})$-alkyl)amino, $(C_2-C_8)$-alkenylamino, $(C_2-C_8)$-alkynylamino, $(C_3-C_{12})$-cycloalkylamino, $(C_3-C_{12})$-cycloalkyl-$(C_1-C_8)$-alkylamino, the radical $R^{15}$—NH—, optionally substituted $(C_6-C_{14})$-aryl-NH, $(C_6-C_{14})$-aryl-$(C_1-C_8)$-alkyl-NH, which can also be substituted in the aryl radical, optionally substituted heteroaryl-NH or heteroaryl-$(C_1-C_8)$-alkyl—NH optionally substituted in the heteroaryl radical;

$R^{13}$ is hydrogen, $(C_1-C_6)$-alkyl, $(C_6-C_{14})$-aryl-$(C_1-C_8)$-alkyl optionally substituted in the aryl radical or $(C_3-C_8)$-cycloalkyl;

$R^{15}$ is $R^{16}$—$(C_1-C_6)$-alkyl or $R^{16}$;

$R^{16}$ is a 6- to 24-membered bicyclic or tricyclic radical which is saturated or partially unsaturated and which can also contain one to four identical or different heteroatoms from the group consisting of nitrogen, oxygen and sulfur and which can also be substituted by one or more identical or different substituents from the group consisting of $(C_1-C_4)$-alkyl and oxo;

$R^{21}$ is hydrogen, $(C_1-C_8)$-alkyl, $(C_3-C_{12})$-cycloalkyl, $(C_3-C_{12})$-cycloalkyl-$(C_1-C_8)$-alkyl, $(C_6-C_{14})$-aryl, $(C_6-C_{14})$-aryl-$(C_1-C_8)$-alkyl, the radical Het- or Het-$(C_1-C_8)$-alkyl, where alkyl radicals can be monosubstituted or polysubstituted by fluorine and the radicals $R^{21}$ can be identical or different if they occur several times;

$R^{22}$ is $(C_3-C_{12})$-cycloalkyl, $(C_3-C_{12})$-cycloalkyl-$(C_1-C_8)$-alkyl, $(C_6-C_{14})$-aryl, the radical Het- or Het-$(C_1-C_8)$-alkyl, where alkyl radicals can be monosubstituted or polysubstituted by fluorine;

$R^{23}$ is $(C_1-C_8)$-alkyl, $(C_3-C_{12})$-cycloalkyl, $(C_3-C_{12})$-cycloalkyl-$(C_1-C_8)$-alkyl, $(C_6-C_{14})$-aryl, $(C_6-C_{14})$-aryl-$(C_1-C_8)$-alkyl, the radical Het- or Het-$(C_1-C_8)$-alkyl, where alkyl radicals can be monosubstituted or polysubstituted by fluorine;

$R^{24}$ $(C_3-C_{12})$-cycloalkyl, $(C_3-C_{12})$-cycloalkyl-$(C_1-C_8)$-alkyl, $(C_6-C_{14})$-aryl, $(C_6-C_{14})$-aryl-$(C_1-C_8)$-alkyl, the radical Het- or Het-$(C_1-C_8)$-alkyl, where alkyl radicals can be monosubstituted or polysubstituted by fluorine;

$R^{25}$ has the meanings of $R^{23}$, where the radicals $R^{25}$ can be identical or different;

$R^{26}$ has the meanings of $R^{21}$ or HO—$((C_1-C_8)$-alkyl), where alkyl radicals can be monosubstituted or polysubstituted by fluorine;

$R^{27}$ is hydrogen, $(C_3-C_{12})$-cycloalkyl, $(C_3-C_{12})$-cycloalkyl-$(C_1-C_8)$-alkyl, $(C_6-C_{14})$-aryl-$(C_1-C_8)$-alkyl, the radical Het- or Het-$(C_1-C_8)$-alkyl, where alkyl radicals can be monosubstituted or polysubstituted by fluorine;

$R^{28}$ is one of the radicals $R^{21}$—, $R^{21}O$—, $R^{26}N(R^{26})$—, $R^{21}C(O)$—, $R^{21}O$—C(O)—, $((C_1-C_{18})$-alkyl-O—C(O)—$((C_1-C_6)$-alkyl)—O—C(O)—, $R^{21}N(R^{21})$—C(O)—, $R^{21}N(R^{21})$—C(=N($R^{21}$))— or $R^{21}C(O)$—N($R^{21}$)—;

Het is a mono- or polycyclic, 4- to 14-membered, aromatic or nonaromatic ring which contains 1, 2, 3 or 4 identical or different heteroatoms from the group consisting of N, O and S as ring members and which can optionally be substituted by one or more, identical or different substituents;

b, c, d and f independently of one another are 0 or 1, but cannot all simultaneously be 0;

e, g and h independently of one another are 0, 1, 2, 3, 4, 5 or 6;

in all their stereoisomeric forms and mixtures thereof in any ratio, and of their physiologically tolerable salts for the production of pharmaceuticals for inhibition of the adhesion and/or migration of leucocytes or for inhibition of the VLA-4 receptor, i.e. of pharmaceuticals for the treatment or prophylaxis of diseases in which leucocyte adhesion and/or leucocyte migration has an undesired extent, or of diseases in which VLA-4-dependent adhesion processes play a part, for example of inflammatory disorders, and the use of the compounds of the formula I in the treatment and prophylaxis of diseases of this type.

Alkyl radicals can be straight-chain or branched. This also applies if they carry substituents or occur as substituents of other radicals, for example in alkoxy, alkoxycarbonyl or aralkyl radicals. The same applies to alkylene radicals. Examples of suitable $(C_1-C_{28})$-alkyl radicals are: methyl, ethyl, propl, butyl, pentyl, hexyl, heptyl, octyl, decyl, undecyl, dodecyl, tridecyl, pentadecyl, hexadecyl, heptadecyl, nonadecyl, eicosyl, docosyl, tricosyl, pentacosyl, hexacosyl, heptacosyl, octacosyl, isopropyl, isobutyl, isopentyl, neuopentyl, isohexyl, 3-methylpentyl, 2,3,5-trimethylhexyl, sec-butyl, tert-butyl, tert-pentyl. Preferred alkyl radicals are methyl, ethyl, propyl, isopropyl, butyl, isobutyl, sec-butyl and tert-butyl. Examples of alkylene radicals are methylene, ethylene, tri-, tetra-, penta- and hexamethylene or methylene substituted by an alkyl radical, for example methylene which is substituted by a methyl group, an ethyl group, an isopropyl group, an isobutyl group or a tert-butyl group.

Alkenyl and alkenylene radicals as well as alkynyl radicals can also be straight-chain or branched. Examples of alkenyl radicals are vinyl, 1-propenyl, allyl, butenyl, 3-methyl-2-butenyl, examples of alkenylene radicals are vinylene or propenylene, and examples of alkynyl radicals are ethynyl, 1-propynyl or propargyl.

Cycloalkyl radicals are, in particular, cyclopropyl, cyclobutyl, cyclopentyl, cyclohexyl, cycloheptyl, cyclooctyl, cyclononyl, cyclodecyl, cycloundecyl and cyclododecyl, which, however, can also be substituted by, for example, $(C_1-C_4)$-alkyl. Examples of substituted cycloalkyl radicals which may be mentioned are 4-methylcyclohexyl and 2,3-dimethylcyclopentyl. The same applies to cycloalkylene radicals.

The 6- to 24-membered bicyclic and tricyclic radicals $R^{16}$ are formally obtained by abstraction of a hydrogen atom from bicyclic systems or tricyclic systems. The bicyclic systems and tricyclic systems on which they are based can contain only carbon atoms as ring members, i. e. they can be bicycloalkanes or tricycloalkanes, but they can also contain one to four identical or different heteroatoms from the group consisting of nitrogen, oxygen and sulfur, i. e. they can be aza-, oxa- and thiabicyclo- and -tricycloalkanes. If heteroatoms are contained, preferably one or two heteroatoms, in particular nitrogen or oxygen atoms, are contained. The heteroatoms can assume any desired positions in the bi- or tricyclic structure; they can be located in the bridges, or in the case of nitrogen atoms, also at the bridgeheads. Both the bicyclo- and tricycloalkanes and their heterocyclic analogs can be completely saturated or can contain one or more double bonds. They preferably contain one or two double bonds or, in particular, are completely saturated. Both the bicyclo- and tricycloalkanes and the heterocyclic analogs and both the saturated and the unsaturated representatives can be unsubstituted or substituted in any desired suitable positions by one or more oxo groups and/or one or more identical or different $(C_1-C_4)$-alkyl groups, for example methyl or isopropyl groups, preferably methyl groups. The free bond of the bi- or tricyclic radical can be located in any desired position of the molecule; the radical can thus be bonded via a bridgehead atom or an atom in a bridge. The free bond can also be located in any desired stereochemical position, for example in an exo or an endo position.

Examples of parent structures of bicyclic ring systems from which a bicycle radical can be derived are norbornane (=bicyclo[2.2.1]heptane), bicyclo[2.2.2]octane and bicyclo[3.2.1]octane, examples of unsaturated or substituted systems or systems containing heteroatoms are 7-azabicyclo[2.2.1]-heptane, bicyclo[2.2.2]oct-5-ene and camphor (=1,7,7-trimethyl-2-oxobicyclo[2.2.1]heptane).

Examples of systems from which a tricyclic radical can be derived are twistane (=tricyclo[4.4.0.0$^{3,8}$]decane), adamantane (=tricyclo[3.3.1.1$^{3,7}$]-decane), noradamantane (=tricyclo[3.3.1.0$^{3,7}$]nonane), tricyclo[2.2.1.0$^{2,6}$]-heptane, tricyclo[5.3.2.0$^{4,9}$]dodecane, tricyclo[5.4.0.0$^{2,9}$]undecane or tricyclo[5.5.1.0$^{3,11}$]tridecane.

Preferably, bicyclic or tricyclic radicals are derived from bridged bicyclic systems or tricyclic systems, i.e. from systems in which rings together have two or more than two atoms. Bicyclic or tricyclic radicals having 6 to 18 ring members are additionally preferred, particularly preferably those having 7 to 12 ring members.

Specifically particularly preferred bi- and tricyclic radicals are the 2-norbornyl radical, both that with the free bond in the exo position and also that with the free bond in the endo position, the 2-bicyclo[3.2.1]octyl radical, the 1-adamantyl radical, the 2-adamantyl radical and the noradamantyl radical, for example the 3-noradamantyl radical. The 1- and the 2-adamantyl radicals are moreover preferred.

$(C_6-C_{14})$-aryl groups are, for example, phenyl, naphthyl, biphenylyl, anthryl or fluorenyl, where 1-naphthyl, 2-naphthyl and in particular phenyl are preferred. Aryl radicals, in particular phenyl radicals, can be mono- or polysubstituted, preferably mono-, di- or trisubstituted, by identical or different radicals from the groups consisting of $(C_1-C_8)$-alkyl, in particular $(C_1-C_4)$-alkyl, $(C_1-C_8)$-alkoxy, in particular $(C_1-C_4)$-alkoxy, halogen, nitro, amino, trifluoromethyl, hydroxyl, methylenedioxy, ethylenedioxy, cyano, hydroxycarbonyl, aminocarbonyl, $(C_1-C_4)$-alkoxycarbonyl, phenyl, phenoxy, benzyl, benzyloxy, $(R^8O_2P(O)$, $(R^8O)_2P(O)$—O—, tetrarzolyl. The same applies, for example, to radicals such as aralkyl or arylcarbonyl. Aralkyl radicals are, in particular, benzyl as well as 1- and 2-naphthylmethyl, 2-, 3- and 4-biphenylylmethyl and 9-fluorenylmethyl which can also be substituted. Substituted aralkyl radicals are, for example, benzyl and naphthylmethyl substituted in the aryl moiety by one or more $(C_1-C_8)$-alkyl radicals, in particular $(C_1-C_4)$-alkyl radicals, for example 2-, 3- and 4-methylbenzyl, 4-isobutylbenzyl, 4-tert-butylbenzyl, 4-octlbenzyl, 3,5-dimethylbenzyl, pentamethylenzyl, 2-, 3- 4-, 5-, 6-, 7-, and 8-methyl-1-naphthylmethyl, 1-, 3-, 4-, 5-, 6-, 7- and 8-methyl-2-naphthylmethyl, or benzyl and naphthylmethyl substituted in the aryl moiety by one or more $(C_1-C_8)$-alkoxy radicals, in particular $(C_1-C_4)$-alkoxy radicals, for example 4-methoxybenzyl, 4-neopentyloxybenzyl, 3,5-dimethoxybenzyl, 3,4-methylenedioxybenzyl, 2,3,4-trimethoxybenzyl, further 2-, 3- and 4-nitrobenzyl, halobenzyl, for example 2-, 3- and 4-chloro- and 2-, 3- and 4-fluorobenzyl, 3,4-dichlorobenzyl, pentafluorobenzyl, trifluoromethylbenzyl, for example 3- and 4-trifluoromethylbenzyl or 3,5-bis(trifluoromethyl)benzyl. Substituted aralkyl radicals, however, can also have different substituents. Examples of pyridyl are 2-pyridyl, 3-pyridyl and 4-pyridyl.

In monosubstituted phenyl radicals, the substituent can be located in the 2-, the 3- or the 4-position, the 3- and the 4-positions being preferred. If phenyl is disubstituted, the substituents can be in the 1,2-, 1,3- or 1,4-position relative to one another. Disubstituted phenyl can thus be substituted in the 2,3-position, the 2,4-position, the 2,5-position, the 2,6-position, the 3,4-position or the 3,5-position, relative to the linkage site. Preferably, in disubstituted phenyl radicals the two substituents are arranged in the 3-position and the 4-position, relative to the linkage site. The same applies for phenylene radicals which, for example, can be present as 1,4-phenylene or as 1,3-phenylene.

Phenylene-$(C_1-C_6)$-alkyl is, in particular, phenylenemethyl (—$C_1H_4$—$CH_2$) and phenyleneethyl, $(C_1-C_6)$-alkylenephenyl is, in particular, methylenephenyl (—$CH_2$—$C_6H_4$—). Phenylene-$(C_2-C_6)$-alkenyl is, in particular, phenyleneethenyl and phenylenepropenyl.

Heteroaryl is a mono- or polycyclic aromatic radical having 5 to 14 rings members, which contains 1 to 5 heteroatoms as ring members. Examples of heteroatoms are N, O and S. If several heteroatoms are contained, these can be identical or different. Heteroaryl radicals can also be mono- or polysubstituted, preferably mono-, di- or trisubstituted, by identical or different radicals from the group consisting of $(C_1-C_8)$-alkyl, in particular $(C_1-C_4)$-alkyl, $(C_1-C_8)$-alkoxy, in particular $(C_1-C_4)$-alkoxy, halogen, nitro, amino, trifluoromethyl, hydroxyl, methylenedioxy, cyano, hydroxycarbonyl, aminocarbonyl, $(C_1-C_4)$-alkoxycarbonyl, phenyl, phenoxy, benzyl, benzyloxy, $(R^8O)_2P(O)$, $(R^8O)_2P(O)$—O—, tetrazolyl. Preferably, heteroaryl is a mono- or bicyclic aromatic radical which contains 1, 2, 3 or 4, particular 1 to 3, identical or different heteroatoms from the group consisting of N, O and S and which can be substituted by 1, 2, 3 or 4, in particular 1 to 3, identical or different substituents from the group consisting of $(C_1-C_6)$-alkyl, $(C_1-C_6)$-alkoxy, fluorine, chlorine, nitro, amino, trifluoromethyl, hydroxyl, (C₁–C₄)-alkoxycarbonyl, phenyl, phenoxy, benzyloxy and benzyl. Particularly preferably, heteroaryl is a mono- or bicyclic aromatic radical having 5 to 10 ring members, in particular a corresponding 5- to 6-membered monocyclic aromatic radical, which contains 1 to 3 heteroatoms from the group consisting of N, O and S and can be substituted by 1 to 2 substituents from the group consisting of (C₁–C₄)-alkyl, (C₁–C₄)-alkoxy, phenyl, phenoxy, benzyloxy and benzyl.

Het on the one hand includes aromatic heterocycles and thus also the groups representing heteroaryl insofar as these come under the definition of Het with respect to the number of ring members and heteroatoms. Additionally, however, Het also includes nonaromatic heterocycles which are completely saturated or which contain one or more double bonds in the ring system. Het can be substituted on nitrogen atoms and/or carbon atoms by one or more identical or different substituents, for example by (C₁–C₈)-alkyl, in particular (C₁–C₄)-alkyl, (C₃–C₁₂)-cycloalkyl, (C₃–C₁₂)-cycloalkyl-(C₁–C₈)-alkyl, optionally substituted (C₆–C₁₄)-aryl, (C₆–C₁₄)-aryl-(C₁–C₈)-alkyl optionally substituted in the aryl radical, heteroaryl, heteroaryl-(C₁–C₈)-alkyl, (C₁–C₈)-alkoxy, in particular (C₁–C₄)-alkoxy, optionally substituted phenoxy, benzyloxy, halogen, nitro, amino, (C₁–C₈)-alkylamino, di-((C₁–C₈)-alkyl)amino, trifluoromethyl, hydroxyl, methylenedioxy, ethylenedioxy, cyano, hydroxylcarbonyl, aminocarbonyl, (C₁–C₄)-alkoxycarbonyl and generally by ester groups, acyl groups (R⁸O)₂P(O), (R⁸O)₂P(O)—O—, oxo, thioxo, where alkyl radicals can be monosubstituted or polysubstituted by fluorine.

Heterocycles which represent mono- or bicyclic 5- to 12-membered heterocyclic rings can be aromatic or partially or completely saturated and can be substituted, i particular on a nitrogen atom, by (C₁–C₇)-alkyl, for example methyl or ethyl, phenyl or phenyl-(C₁–C₄)-alkyl, for example benzyl, and/or on one or more carbon atoms by (C₁–C₄)-alkyl, halogen, hydroxyl, (C₁–C₄)-alkoxy, for example methoxy, phenyl-(C₁–C₄)-alkoxy, for example benzyloxy, or oxo.

Examples of heterocycles on which the groups heteroaryl, Het or the mono- or bicyclic 5- to 12-membered heterocyclic ring can be based are pyrrole, furan, thiophene, imidazole, pyrazole, oxazole, isoxazole, thiazole, isothiazole, tetrazole, pyridine, pyrazine, pyrimidine, indole, isoindole, indazole, phthalazine, quinoline, isoquinoline, quinoxaline, quinazoline, cinnoline, β-carboline or benzo-fused, cyclopenta-, cyclohexa- or cyclohepta-fused derivatives of these heterocycles. Nitrogen heterocycles can also be present as N-oxides.

Radicals which can represent heteroaryl, Het or the radical of a mono- or bicyclic 5- to 12-membered heterocyclic ring are, for example, 2- or 3-pyrrolyl, phenylpyrrolyl, for example 4- or 5-phenyl-2-pyrrolyl, 2-furyl, 2-thienyl, 4-imidazoly, methylimidizolyl, for example 1-methyl-2-, -4- or -5-imidazolyl, 1,3-thiazol-2-yl, 2-pyridyl, 3-pyridyl, 4-pyridyl, 2-, 3- or 4-pyridyl-N-oxide, 2-pyrazinyl, 2-, 4- or 5-pyrimidinyl, 2-, 3- or 5-indolyl, substituted 2-indolyl, for example 1-methyl-, 5-methyl, 5-methoxy, 5-benzyloxy-, 5-chloro or 4,5-dimethyl-2-indolyl, 1-benzyl-2-, or -3-indolyl, 4,5,6,7-tetrahydro-2-indolyl, cyclohepta[b]-5-pyrrolyl, 2-, 3- or 4-quinolyl, 1-, 3- or 4-isoquinolyl, 1-oxo-1,2-dihydro-3-isoquinolyl, 2-quinoxalinyl, 2-benzofuranyl, 2-benzothienyl, 2-benzoxazolyl or benzothiazolyl or, as radicals of partially hydrogenated or completely hydrogenated heterocyclic rings, for example also dihydropyridinyl, pyrrolidinyl, for example 2- or 3-(N-methylpyrrolidinyl), piperazinyl, morpholinyl, thiomorpholinyl, tetrahydrothienyl, benzodioxolanyl.

Further examples of radicals which in particular can represent Het- and the substituent R¹ are

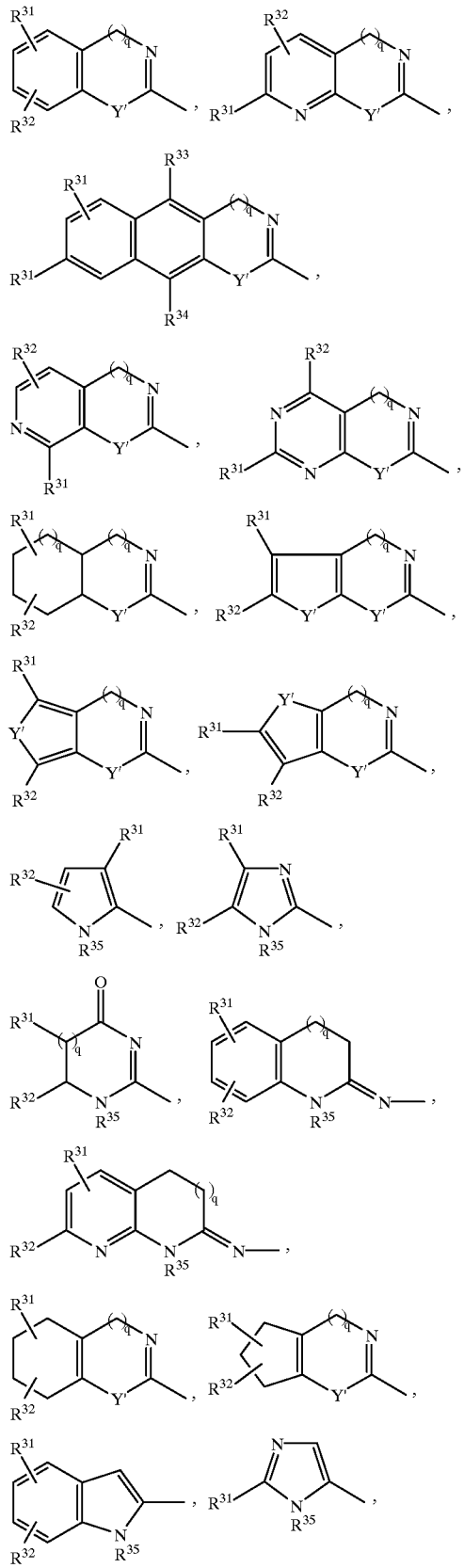

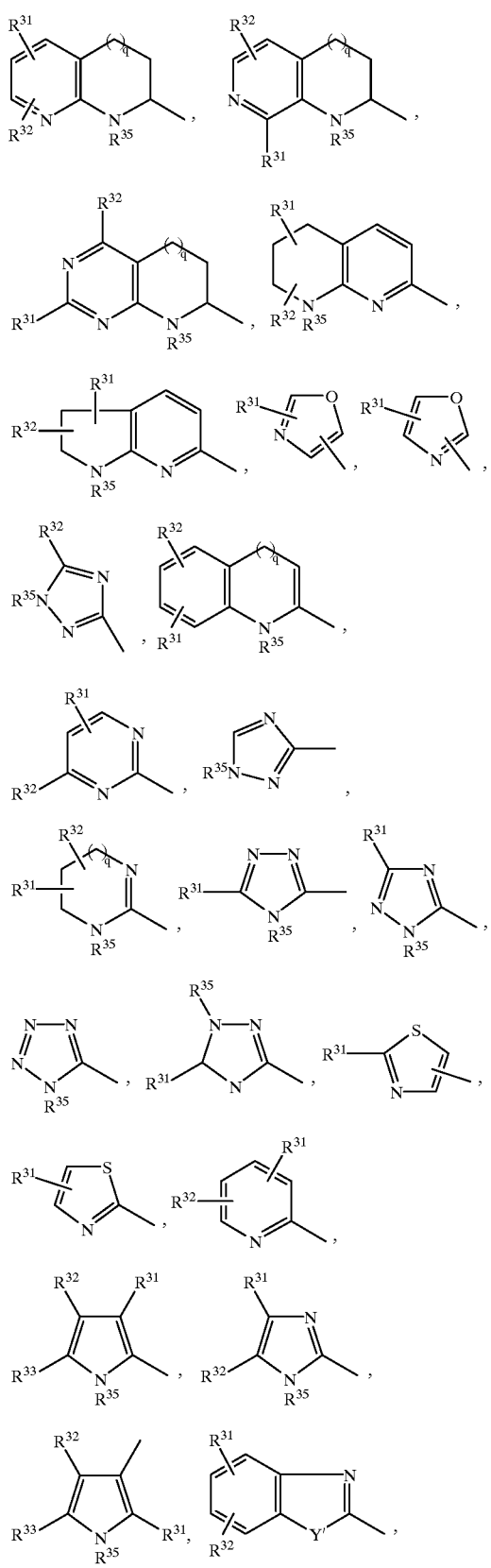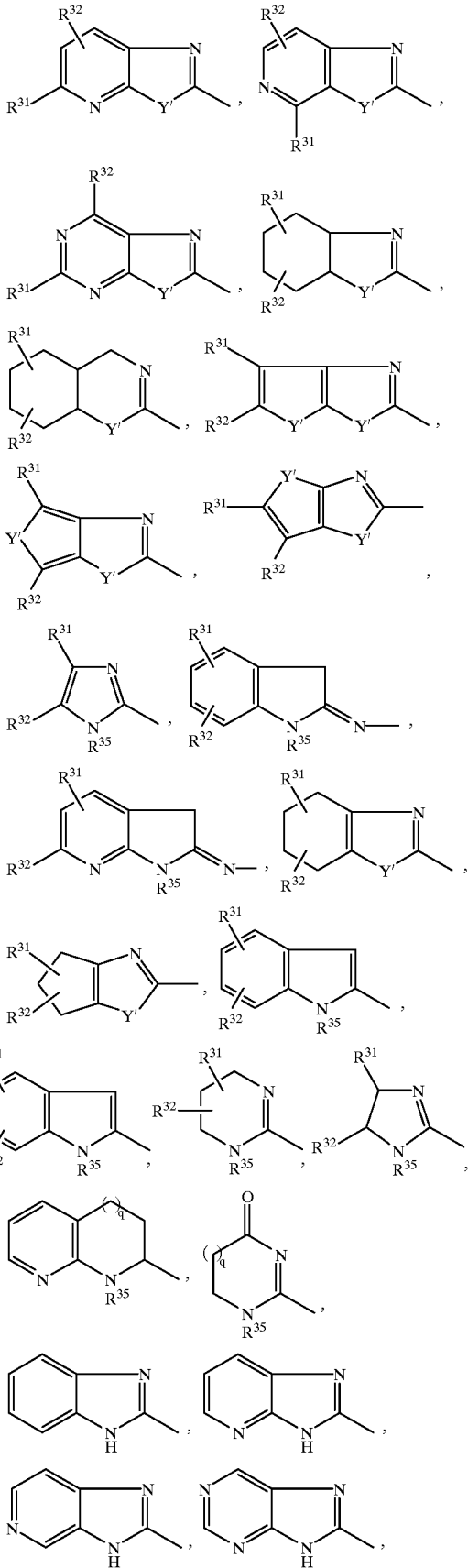

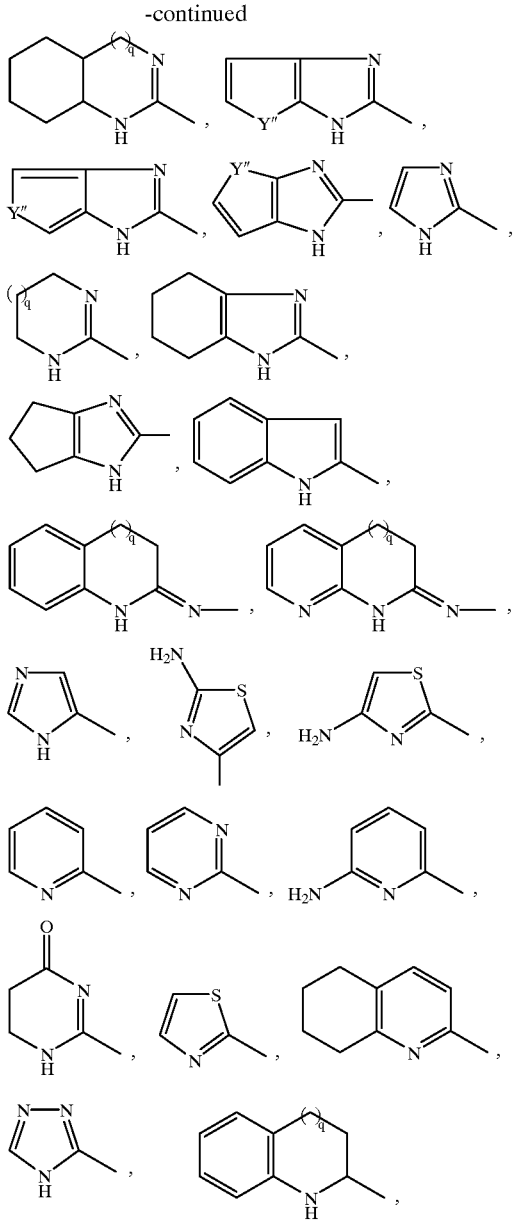

in which Y' is NR³⁵, O or S;

Y" is NH, O or S;

R³¹, R³², R³³ and R³⁴ independently of one another are hydrogen, (C₁–C₈)-alkyl, in particular (C₁–C₄)-alkyl, (C₃–C₁₂)-cycloalkyl, (C₃–C₁₂)-cycloalkyl-(C₁–C₈)-alkyl, optionally substituted (C₆–C₁₄)-aryl, (C₆–C₁₄)-aryl-(C₁–C₈)-alkyl optionally substituted in the aryl radical, heteroaryl, heteroaryl-(C₁–C₈)-alkyl, (C₁–C₈)-alkoxy, in particular (C₁–C₄)-alkoxy, halogen, nitro, amino, (C₁–C₈)-alkylamino, di((C₁–C₈)-alkyl)amino, trifluoromethyl, hydroxyl, methylenedioxy, cyano, hydroxylcarbonyl, aminocarbonyl, (C₁–C₄)-alkoxycarbonyl, optionally substituted phenoxy, benzyloxy, (R⁸O)₂P(O),(R₈O)₂P(O)—O—, oxo, thioxo, where alkyl radicals can be monosubstituted or polysubstituted by fluorine;

R³⁵ is hydrogen, (C₁–C₁₀)-alkyl which can optionally be monosubstituted or polysubstituted by fluorine, (C₃–C₁₂)-cycloalkyl, (C₃–C₁₂)-cycloalkyl-(C₁–C₈)-alkyl, optionally substituted (C₆–C₁₄)-aryl, (C₆–C₁₄)-aryl-(C₁–C₈)-alkyl optionally substituted in the aryl radical, heteroaryl, heteroaryl-(C₁–C₈)-alkyl, hydroxyl, (C₁–C₈)-alkoxy, amino aminocarbonyl, formyl, R³⁶C(O), R³⁶O—C(O) or ((C₁–C₁₈)-alkyl,—O—C(O)—((C₁–C₆)-alkyl—O—C(O)—;

R³⁶ is (C₁–C₁₀)-alkyl, (C₃–C₁₂)-cycloalkyl, (C₃–C₁₂)-cycloalkyl-(C₁–C₈)-alkyl, optionally substituted (C₆–C₁₄)-aryl, (C₆–C₁₄)-aryl-(C₁–C₈)-alkyl optionally substituted in the aryl radical, heteroaryl or heteroraryl-(C₁–C₈)-alkyl;

q is 0 or 1.

Halogen is fluorine, chlorine, bromine or iodine, in particular fluorine or chlorine.

If chiral, natural or unnatural amino acids can be present in the D- or L-form, α-Amino acids are preferred. Examples which may be mentioned are (cf. Houben-Weyl, Methoden der organischen Chemie [Methods of organic chemistry], Volume 15/1 and 15/2, Georg Thieme Verlag, Stuttgart, 1974);

AAd, Abu, γAbu, ABz, 2ABz, εAca, Ach, Acp, Adpd, Ahb, Aib, βAib, Ala, βAla, ΔAla, Alg, All, Ama, Amt, Ape, Apm, Apr, Arg, Asn, Asp, Asu, Aze, Azi, Bai, Bph, Can, Cit, Cys, (Cys)₂, Cyta, Daad, Dab, Dadd, Dap, Dapm, Dasu, Djen, Dpa, Dte, Fel, Gln, Glu, Gly, Guv, hAla, hArg, hCys, hGln, hGlu, His, hIle, hLeu, hLys, hMet, hPhe, hPro, hSer, hThr, hTrp, hTyr, Hyl, Hyp, 3Hyp, Ile, Ise, Iva, Kyn, Lant, Lcn, Leu, Lsg, Lys, βLys, ΔLys, Met, Mim, Min, nArg, Nle, Nva, Oly, Orn, Pan, Pec, Pen, Phe, Phg, Pic, Pro, ΔPro, Pse, Pya, Pyr, Pza, Qin, Ros, Sar, Sec. Sem, Ser. Thi, βThi, Thr, Thy, Thx, Tia, Tle, Tly, Trp, Trta, Tyr, Val, tert-butylglycine (TBg), neopentylglycine (Npg), cyclohexylglycine (Chg), cyclohexylalanine (Cha), 2-thienylalanine (Thia), 2,2-diphenylaminoacetic acid, 2-(p-tolyl)-2-phenylaminoacetic acid, 2-(p-chlorophenyl)-amino acetic acid.

Amino acid side chains are understood as meaning side chains of natural or unnatural amino acids. Azaamino acids are natural or unnatural amino acids in which the central unit

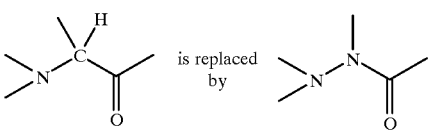

Suitable radicals of an imino acid are, in particular, radicals of heterocycles from the following group: pyrrolidine-2-carboxylic acid; piperidine-2-carboxylic acid; 1,2,3,4-tetrahydroisoquinoline-3-carboxylic acid; decahydroisoquinoline-3-carboxylic acid; octahydroindole-2-carboxylic acid; decahydroquinoline-2-carboxylic acid; octahydrocyclopenta[b]pyrrole-2-carboxylic acid; 2-azabicyclo[2.2.2]octane-3-carboxylic acid; 2-azabicyclo[2.2.1]heptane-3-carboxylic acid; 2-azabicyclo[3.1.0] hexane-3-carboxylic acid; 2-azaspiro[4.4]nonane-3-carboxylic acid; 2-azaspiro[4.5]decane-3-carboxylic acid; spiro(bicyclo[2.2.1](heptane)-2,3-pyrrolidine-5-carboxylic acid; spiro(bicyclo[2.2.2]octane)-2,3-pyrrolidine-5-carboxylic acid; 2-azatricyclo[4.3.0.1⁶,⁹]decane-3-carboxylic acid; decahydrocyclohepta[b]pyrrole-2-carboxylic acid; decahydrocycloocta[c]pyrrole-2-carboxylic acid; octahydrocyclopenta[c]pyrrole-2-carboxylic acid; octahydroisoindole-1-carboxylic acid; 2,3,3a,4,6a-hexahydrocyclopenta[b]pyrrole-2-carboxylic acid, 2,3,3a,4, 5,7a-hexahydroindole-2-carboxylic aid; tetrahydrothiazole-4-carboxylic acid; isoxazolidine-3-carboxylic acid; pyrazolidine-3-carboxylic acid, hydroxypyrrolidine-2-carboxylic acid, all of which can optionally be substituted (see following formulae):

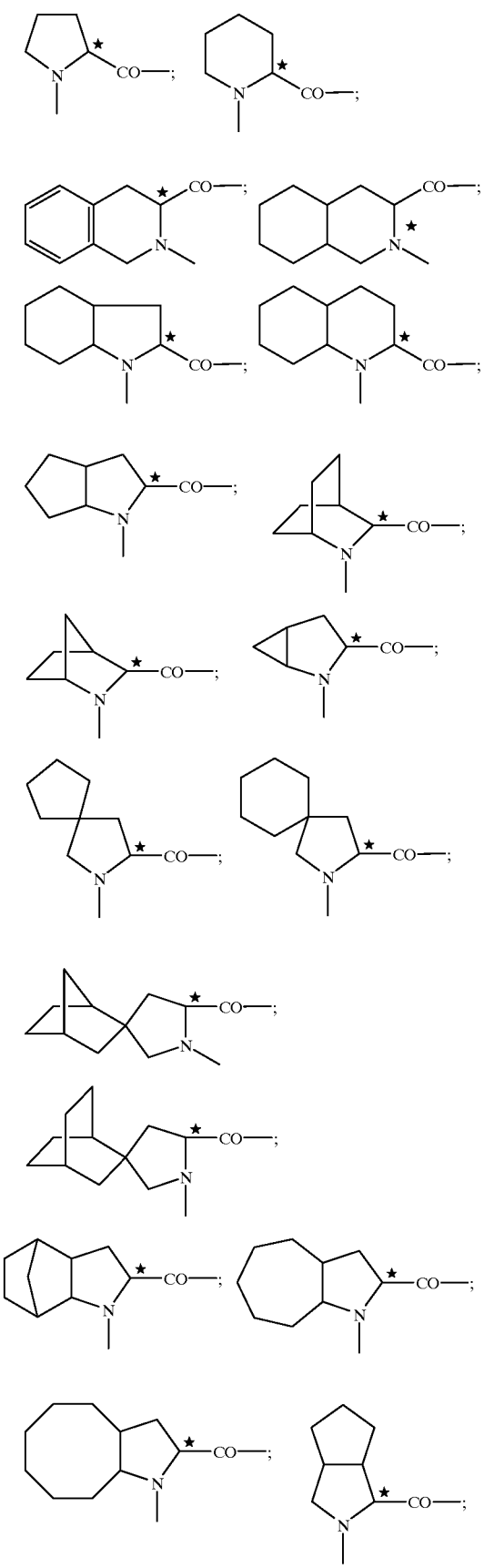
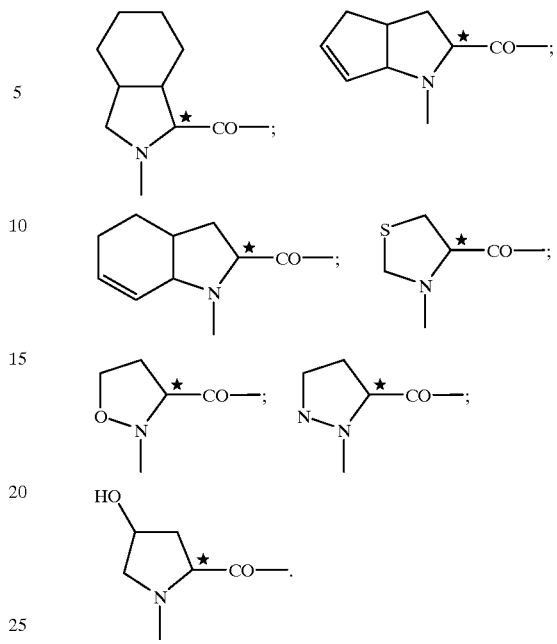

The heterocycles on which the abovementioned radicals are based are disclosed, for example, in U.S. Pat. No. 4,344,949; U.S. Pat. No. 4,374,847; U.S. Pat. No. 4,350,704; EP-A 29,488; EP-A 31,741; EP-A 46,953; EP-A 49,605; EP-A 49,658; EP-A 50,800; EP-A 51,020; EP-A 52,870; EP-A 79,022; EP-A 84,164; EP-A 89,637; EP-A 90,341; EP-A 90,362; EP-A 105,102; EP-A 109,020; EP-A 111,873; EP-A 271,865 and EP-A 344,682.

Dipeptides can contain natural or unnatural amino acids, imino acids as well as azaamino acids as structural units. The natural or unnatural amino acids, imino acids, azaamino acids and dipeptides can further be present also as esters or amides, such as, for example, as the methyl ester, ethyl ester, isopropyl ester, isobutyl ester, tert-butyl ester, benzyl ester, unsubstituted amide, ethylamide, semicarbazide or ω-amino-$(C_2-C_8)$-alkylamide.

Functional groups of the amino acids, imino acids and dipeptides can be present in protected form. Suitable protective groups such as, for example, urethane protective groups, carboxyl protective groups and side chain protective groups are described in Hubbuch, Kontakte (Merck) 1979, No. 3, pages 14 to 23, and in Büllesbach, Kontakte (Merck) 1980, No. 1, pages 23 to 35. The following may be mentioned in particular; Aloc, Pyoc, Fmoc, Tcboc, Z, Boc, Ddz, Bpoc, Adoc, Msc, Moc, $Z(NO_2)$, $Z(Hal_n)$, Bobz, Iboc, Adpoc, Mboe, Acm, tert-butyl, OBzl, ONbzl, OMbzl, Bzl, Mob, Pic, Trt.

Physiologically tolerable salts of the compounds of the formula I are, in particular, pharmaceutically utilizable or nontoxic salts.

Such salts are formed, for example, from compounds of the formula I which contain acidic groups, for example carboxyl, with alkali metals or alkaline earth metals, such as, for example, Na, K, Mg and Ca, and also with physiologically tolerable organic amines, such as, for example, triethylamine, ethanolamine or tris(2-hydroxyethyl)amine.

Compounds of the formula I which contain basic groups, for example an amino group or a guanidino group, form salts with inorganic acids, such as, for example, hydrochloric acid, sulfuric acid or phosphoric acid, and with organic carboxylic or sulfonic acids, such as, for example, acetic acid, citric acid, benzoic acid, maleic acid, fumaric acid, tartaric acid, methanesulfonic acid or p-toluenesulfonic acid.

Salts can be obtained from the compounds of the formula I by customary methods known to the person skilled in the art, for example by combination with an organic or inorganic acid or base in a solvent or dispersant, or alternatively from other salts by anion exchange or cation exchange.

The compounds of the formula I can be present in stereoisomeric forms. If the compounds of the formula I contain one or more centers of asymmetry, these can independently of one another have the S configuration or the R configuration. The invention includes all possible stereoisomers, for example enantiomers and diastereomers, and mixtures of two or more stereoisomeric forms, for example mixtures of enantiomers and/or diastereomers, in all ratios. The invention thus relates to enantiomers in enantiomerically pure form, both as levo- and as dextrorotatory antipodes, in the form of racemates and in the form of mixtures of the two enantiomers in all ratios. If cis/trans isomerism is present, the invention relates to both the cis form and the trans form and mixtures of these forms.

The compounds of the formula I according to the invention can moreover contain mobile hydrogen atoms, i.e. can be present in various tautomeric forms. The present invention also relates to all these tautomers. The present invention furthermore includes all solvates of compounds of the formula I, for example hydrates or adducts with alcohols, as well as derivatives of the compounds of the formula I, for example esters, prodrugs and metabolites which act like the compounds of the formula I.

The individual structural elements in the formula I preferably have the following meanings.

W is preferably $R^1$—A—$C(R^{13})$.

A is preferably methylene, ethylene, trimethylene, tetramethylene, pentamethylene, cyclohexylene, phenylene, methylenephenyl methylenephenylmethyl, phenylenemethyl or phenyleneethyl.

Y is preferably a carbonyl groups.

Z is preferably $N(R^0)$.

B is preferably methylene, ethylene, trimethylene, tetramethylene, vinylene, phenylene or substituted methylene or ethylene. B is particularly preferably a bivalent methylene radical or ethylene radical (=1,2-ethylene), where each of these radicals can be unsubstituted or substituted, in particular an unsubstituted or substituted methylene radical. These two radicals are very particularly preferably substituted. If a bivalent methylene radical or ethylene radical (=1,2-ethylene) representing B is substituted, it is preferably substituted by a radical from the group consisting of $(C_1-C_8)$-alkyl, $(C_2-C_6)$-alkenyl, $(C_2-C_6)$-alkynyl, $(C_3-C_8)$-cycloalkyl, in particular $(C_5-C_6)$-cycloalkyl, $(C_3-C_8)$-cycloalkyl-$(C_1-C_4)$-alkyl, in particular $(C_5-C_6)$-cycloalkyl-$(C_1-C_4)$-alkyl, optionally substituted $(C_6-C_{10})$-aryl, $(C_6-C_{10})$-aryl-$(C_1-C_4)$-alkyl optionally substituted in the aryl radical, optionally substituted heteroaryl or heteroaryl-$(C_1-C_4)$-alkyl optionally substituted in the heteroaryl radical, and it is particularly preferably substituted by $(C_1-C_8)$-alkyl, i.e. by a straight-chain or branched alkyl radical having 1,2,3,4, 5,6,7 or 8 carbon atoms.

D is preferably $C(R^2)(R^3)$.

E is preferably $R^{10}CO$.

R is preferably hydrogen, $(C_1-C_6)$-alkyl or benzyl, in particular hydrogen, methyl or ethyl.

$R^0$ is preferably $(C_1-C_8)$-alkyl, $(C_3-C_{12})$-cycloalkyl, $(C_3-C_{12})$-cycloalkyl-$(C_1-C_8)$-alkyl, optionally substituted $(C_6-C_{14})$-aryl, $(C_6-C_{14})$-aryl-$(C_1-C_8)$-alkyl optionally substituted in the aryl radical, optionally substituted heteroaryl or heteroaryl-$(C_1-C_8)$-alkyl optionally substituted in the heteroaryl radical, particularly preferably $(C_1-C_8)$-alkyl, $(C_3-C_{12})$-cycloalkyl, $(C_3-C_{12})$-cycloalkyl-$(C_1-C_4)$-alkyl, optionally substituted $(C_6-C_{14})$-aryl, $(C_6-C_{14})$-aryl-$(C_1-C_4)$-alkyl optionally substituted in the aryl radical, optionally substituted heteroaryl or heteroaryl-$(C_1-C_4)$-alkyl optionally substituted in the heteroaryl radical, very particularly preferably optionally substituted $(C_6-C_{14})$-aryl or $(C_6-C_{14})$-aryl-$(C_1-C_8)$-alkyl optionally substituted in the aryl radical, moreover preferably $(C_6-C_{14})$-aryl-$(C_1-C_8)$-alkyl optionally substituted in the aryl radical. It is specifically preferred if $R^0$ is biphenylylmethyl, naphthylmethyl or benzyl, each of which is unsubstituted or mono- or polysubstituted in the aryl radical.

$R^1$ is preferably one of the radicals $R^{21}O$—, $R^{24}NH$—, $R^{25}N(R^{25})$-, HO—$((C_1-C_8)$-alkyl)—$N(R^{26})$—, $R^{21}O$—$C(O)$— and $R^{28}N(R^{21})$—$C(O)$—.

$R^2$ is preferably hydrogen or $(C_1-C_8)$-alkyl.

$R^3$ is preferably $(C_1-C_8)$-alkyl, optionally substituted $(C_6-C_{14})$-aryl, $(C_6-C_{14})$-aryl-$(C_1-C_8)$-alkyl optionally substituted in the aryl radical, $(C_3-C_8)$-cycloalkyl, $(C_2-C_8)$-alkenyl, $(C_2-C_8)$-alkynyl, pyridyl, $R^{11}NH$, $R^4CO$, $COOR^4$, $CON(CH_3)R^4$, $CONHR^4$, $CSNHR^4$, $COOR^{15}$, $CON(CH_3)R^{15}$ or $CONHR^{15}$, particularly preferably optionally substituted $(C_6-C_{14})$-aryl, $R^{11}NH$, $CON(CH_3)R^4$ or $CONHR^4$.

$R^4$ is preferably $(C_1-C_8)$-alkyl which can optionally be substituted as indicated in the definition of $R^4$.

$R^{11}$ is preferably hydrogen, $(C_1-C_{18})$-alkyl, $R^{12}CO$, optionally substituted $(C_6-C_{14})$-aryl—$S(O)_2$, $(C_1-C_{18})$-alkyl—$S(O)_2$, $(C_6-C_{14})$-aryl-$(C_1-C_8)$-alkyl optionally substituted in the aryl radical, $R^9NHS(O)_2$ or the radical $R^{15}$, where $R^{12}$ here is hydrogen, $(C_1-C_{18})$-alkyl, $(C_2-C_8)$-alkenyl, $(C_2-C_8)$-alkynyl, optionally substituted $(C_6-C_{14})$-aryl, $(C_1-C_{18})$-alkoxy, $(C_6-C_{14})$-aryl-$(C_1-C_8)$-alkoxy which can also be substituted in the aryl radical, optionally substituted $(C_6-C_{14})$-aryloxy, amino or mono- or di-$((C_1-C_{18})$-alkyl)amino, the radical $R^{15}$ or the radical $R^{15}$—O—.

$R^{13}$ is preferably hydrogen and in particular $(C_1-C_6)$-alkyl, $(C_3-C_8)$-cycloalkyl or benzyl, where a very particularly preferred alkyl radical representing $R^{13}$ is the methyl radical.

$R^{15}$ is preferably $R^{16}$-$(C_1-C_3)$-alkyl or $R^{16}$, particularly preferably $R^{16}$-$(C_1)$-alkyl or $R^{16}$. Moreover, when $R^3$ is $COOR^{15}$, $R^{15}$ is preferably the exo-2-norbornyl radical, the endo-2-norbornyl radical or the bicyclo[3.2.1]octyl radical, and when $R^3$ is $CONHR^{15}$, $R^{15}$ is the exo-2-norbornyl radical, the endo-2-norbornyl radical, the 3-noradamantyl radical and in particular the 1-adamantyl radical, the 2-adamantyl radical, the 1-adamantylmethyl radical or the 2-adamantylmethyl radical.

$R^{16}$ is preferably a 7- to 12-membered bridged bicyclic or tricyclic radical, which is saturated or partially unsaturated and which can also contain one to four identical or different heteroatoms from the group consisting of nitrogen, oxygen and sulfur and which can also be substituted by one or more identical or different substitutents from the group consisting of $(C_1-C_4)$-alkyl and oxo.

b, c and d independently of one another are 1.

e, g and h preferably independently of one another are the numbers 0, 1, 2 or 3.

Compounds preferred for the use according to the invention are those in which, in the formula I simultaneously W is $R^1$—A—$C(R^{13})$ or $R^1$—A—CH=C;

Y is a carbonyl thiocarbonyl or methylene group;

Z is $N(R^0)$, oxygen, sulfur or a methylene group;

A is a bivalent radical from the group consisting of $(C_1-C_6)$-alkylene, $(C_3-C_{12})$-cycloalkylene, $(C_1-C_6)$-alkylene-$(C_3-C_{12})$-cycloalkyl, phenylene, phenylene-$(C_1-C_6)$-alkyl, $(C_1-C_6)$-alkylenephenyl, $(C_1-C_6)$-alkylenephenyl-$(C_1-C_6)$-alkyl, phenylene-$(C_2-C_6)$-alkenyl or a bivalent radical of a 5- or 6-membered saturated or unsaturated ring which can contain 1 or 2 nitrogen atoms and can be mono- or disubstituted by $(C_1-C_6)$-alkyl or doubly bonded oxygen or sulfur;

B is a bivalent radical from the group consisting of $(C_1-C_6)$-alkylene, $(C_2-C_6)$-alkenylene, phenylene, phenylene-$(C_1-C_3)$-alkyl, $(C_1-C_3)$-alkylenephenyl;

D is $C(R^2)(R^3)$, $N(R^3)$ or CH=$C(R^3)$;

E is tetrazolyl, $(R^8O)_2P(O)$, $HOS(O)_2$, $R^9NHS(O)_2$ or $R^{10}CO$;

R and $R^0$ independently of one another are hydrogen, $(C_1-C_8)$-alkyl; $(C_3-C_{12})$-cycloalkyl, $(C_3-C_{12})$-cycloalkyl-$(C_1-C_8)$-alkyl, optionally substituted $(C_6-C_{14})$-aryl, $(C_6-C_{14})$-aryl-$(C_1-C_8)$-alkyl optionally substituted in the aryl radical, optionally substituted heteroaryl or heteroaryl-$(C_1-C_8)$-alkyl optionally substituted in the heteroaryl radical, where alkyl radicals can be mono- or polysubstituted by fluorine;

$R^1$ is hydrogen, $(C_1-C_{10})$-alkyl, which can optionally be monosubstituted or polysubstituted by fluorine, $(C_3-C_{12})$-cycloalkyl, $(C_3-C_{12})$-cycloalkyl-$(C_1-C_8)$-alkyl, optionally substituted $R^{21}$-$((C_6-C_{14})$-aryl), $(R^{21}$-$((C_6-C_{14})$-aryl))-$(C_1-C_8)$-alkyl optionally substituted in the aryl radical, the radical Het-, Het-$(C_1-C_8)$-alkyl or one of the radicals $R^{21}O$—, $R^{22}O$—NH—, $R^{21}O$—$N(R^{23})$—, $R^{24}NH$—, $R^{25}N(R^{25})$—, HO—$((C_1-C_8)$-alkyl)—N$(R^{26})$—, $R^{27}CO)$—NH—, $R^{21}C(O)$—$N(R^{23})$—, $R^{21}C(O)$—, $R^{21}O$—$C(O)$—, $R^{28}N(R^{21})$—$C(O)$—, $R^{21}O$—N=, O= and S=;

$R^2$ is hydrogen, $(C_1-C_8)$-alkyl, optionally substituted $(C_6-C_{14})$-aryl, $(C_6-C_{14})$-aryl-$(C_1-C_8)$-alkyl optionally substituted in the aryl radical or $(C_3-C_8)$-cycloalkyl;

$R^3$ is hydrogen, $(C_1-C_8)$-alkyl, optionally substituted $(C_6-C_{14})$-aryl, $(C_6-C_{14})$-aryl-$(C_1-C_8)$-alkyl optionally substituted in the aryl radical, $(C_3-C_8)$-cycloalkyl, $(C_2-C_8)$-alkenyl, $(C_2-C_8)$-alkynyl, $(C_2-C_8)$-alkenylcarbonyl, $(C_2-C_8)$-alkynylcarbonyl, pyridyl, $R^{11}NH$, $R^4CO$, $COOR^4$, $CON(CH_3)R^4$, $CONHR^4$, $CSNHR^4$, $COOR^{15}$, $CON(CH_3)R^{15}$ or $CONHR^{15}$;

$R^4$ is hydrogen or $(C_1-C_{28})$-alkyl which can optionally be mono- or polysubstituted by identical or different radicals from the group consisting of hydroxyl, hydroxycarbonyl, aminocarbonyl, mono- or di-$((C_1-C_{18})$-alkyl)aminocarbonyl, amino-$(C_2-C_{18})$-alkylaminocarbonyl, amino-$(C_1-C_3)$-alkylphenyl-$(C_1-C_3)$-alkylaminocarbonyl, $(C_1-C_{18})$-alkylcarbonylamino-$(C_1-C_3)$-alkylphenyl-$(C_1-C_3)$-alkylaminocarbonyl, $(C_1-C_{18})$-alkylcarbonylamino-$(C_2-C_{18})$-alkylaminocarbonyl, $(C_6-C_{14})$-aryl-$(C_1-C_8)$-alkoxycarbonyl which can also be substituted in the aryl radical, amino, mercapto, $(C_1-C_{18})$-alkoxy, $(C_1-C_{18})$-alkoxycarbonyl, optionally substituted $(C_3-C_8)$-cycloalkyl, $HOS(O)_2$—$(C_1-C_3)$-alkyl, $R^9NHS(O)_2$-$(C_1-C_3)$-alkyl, $(R^8O)_2P(O)$—$(C_1-C_3)$-alkyl, tetrazolyl-$(C_1-C_3)$-alkyl, halogen, nitro, trifluoromethyl or the radical $R^5$;

$R^5$ is optionally substituted $(C_6-C_{14})$-aryl, $(C_6-C_{14})$-aryl-$(C_1-C_8)$-alkyl optionally substituted in the aryl radical, a mono- or bicyclic 5- to 12-membered heterocyclic ring which can be aromatic, partially hydrogenated or completely hydrogenated and which can contain one, two or three identical or different heteroatoms from the group consisting of nitrogen, oxygen and sulfur, a radical $R^6$ or a radical $R^6CO$—, where the aryl radical and, independently thereof, the heterocyclic radical can be mono- or polysubstituted by identical or different radicals from the group consisting of $(C_1-C_{18})$-alkyl, $(C_1-C_{18})$-alkoxy, halogen, nitro, amino or trifluoromethyl;

$R^6$ is $R^7R^8N$, $R^7O$ or $R^7S$ or an amino acid side chain, a natural or unnatural amino acid, imino acid, optionally N—$(C_1-C_8)$-alkylated or N—$((C_6-C_{14})$-aryl-$(C_1-C_8)$-alkylated) azaamino acid or a dipeptide radical which can also be substituted in the aryl radical and/or in which the peptide bond can be reduced to —NH—$CH_2$—, and their esters and amides, where hydrogen or hydroxymethyl can optionally stand in place of free functional groups and/or where free functional groups can be protected by protective groups customary in peptide chemistry;

$R^7$ is hydrogen, $(C_1-C_{18})$-alkyl, $(C_6-C_{14})$-aryl-$(C_1-C_8)$-alkyl, $(C_1-C_{18})$-alkylcarbonyl, $(C_1-C_{18})$-alkoxycarbonyl, $(C_6-C_{14})$-arylcarbonyl, $(C_6-C_{14})$-aryl-$(C_1-C_8)$-alkylcarbonyl or $(C_6-C_{14})$-aryl-$(C_1-C_{18})$-alkyloxycarbonyl, where the alkyl groups can optionally be substituted by an amino group and/or where the aryl radicals can be mono- or polysubstituted, preferably monosubstituted, by identical or different radicals from the group consisting of $(C_1-C_8)$-alkyl, $(C_1-C_8)$-alkoxy, halogen, nitro, amino and trifluoromethyl, or is a natural or unnatural amino acid, imino acid, optionally N—$(C_1-C_8)$-alkylated or N—$((C_6-C_{14})$-aryl-$(C_1-C_8)$-alkylated) azaamino acid or a dipeptide radical which can also be substituted in the aryl radical and/or in which the peptide bond can be reduced to —NH—$CH_2$—;

$R^8$ is hydrogen $(C_1-C_{18})$-alkyl, optionally substituted $(C_6-C_{14})$-aryl or $(C_6-C_{14})$-aryl-$(C_1-C_8)$-alkyl which can also be substituted in the aryl radical;

$R^9$ is hydrogen, aminocarbonyl, $(C_1-C_{18})$-alkylaminocarbonyl, $(C_3-C_8)$-cycloalkylaminocarbonyl, optionally substituted $(C_6-C_{14})$-arylaminocarbonyl, $(C_1-C_{18})$-alkyl, optionally substituted $(C_6-C_{14})$-aryl or $C_3-C_8)0$cycloalkyl;

$R^{10}$ is hydroxyl, $(C_1-C_{18})$-alkoxy, $(C_6-C_{14})$-aryl-$(C_1-C_8)$-alkoxy which can also be substituted in the aryl radical, optionally substituted $(C_6-C_{14})$-aryloxy, amino or mono- or di-$((C_1-C_{18})$-alkyl)amino;

$R^{11}$ is hydrogen, $(C_1-C_{18})$-alkyl, $R^{12}CO$, optionally substituted $(C_6-C_{14})$-aryl-$S(O)_2$, $(C_1-C_{18})$-alkyl-$S(O)_2$, $(C_6-C_{14})$-aryl-$(C_1-C_8)$-alkyl optionally substituted in the aryl radical, $R^9NHS(O)_2$ or the radical $R^{15}$;

$R^{12}$ is hydrogen $(C_1-C_{18})$-alkyl, $(C_2-C_8)$-alkenyl, $(C_2-C_8)$-alkynyl, optionally substituted $(C_6-C_{14})$-aryl, $(C_1-C_{18})$-alkoxy, $(C_6-C_{14})$-aryl-$(C_1-C_8)$-alkoxy which can also be substituted in the aryl radical, optionally substituted $(C_6-C_{14})$-aryloxy, amino or mono- or di-$((C_1-C_{18})$-alkyl)amino, the radical $R^{15}$ or the radical $R_{15}$—O—;

$R^{13}$ is hydrogen, $(C_1-C_6)$-alkyl, $(C_6-C_{14})$-aryl-$(C_1-C_8)$-alkyl optionally substituted in the aryl radical or $(C_3-C_8)$-cycloalkyl $R^{15}$ is $R^{16}$-$(C_1-C_6)$-alkyl or $R^{16}$;

$R^{16}$ is a 6- to 25-membered bicyclic or tricyclic radical which is saturated or partially unsaturated and which can also contain one to four identical or different heteroatoms from the group consisting of nitrogen, oxygen and sulfur and which can also be substituted by one or more identical or different substituents from the group consisting of $(C_1-C_4)$-alkyl and oxo;

$R^{21}$ is hydrogen, $(C_1-C_8)$-alkyl, $(C_3-C_{12})$-cycloalkyl, $(C_3-C_{12})$-cycloalkyl-$(C_1-C_8)$-alkyl, $(C_6-C_{14})$-aryl, $(C_6-C_{14})$-aryl-$(C_1-C_8)$-alkyl, the radical Het- or Het-$(C_1-C_8)$-alkyl, where alkyl radicals can be monosubstituted or polysubstituted by fluorine and the radicals $R^{21}$ can be identical or different if they occur several times;

$R^{22}$ is $(C_3-C_{12})$-cycloalkyl, $(C_3-C_{12})$-cycloalkyl-$(C_1-C_8)$-alkyl, $(C_6-C_{14})$-aryl, the radical Het- or Het-$(C_1-C_8)$-alkyl, where alkyl radicals can be monosubstituted or polysubstituted by fluorine;

$R^{23}$ is $(C_1-C_8)$-alkyl, $(C_3-C_{12})$-cycloalkyl, $(C_3-C_{12})$-cycloalkyl-$(C_1-C_8)$-alkyl, $(C_6-C_{14})$-aryl, $(C_6-C_{14})$-aryl-$(C_1-C_8)$-alkyl, the radical Het- or Het-$(C_1-C_8)$-alkyl, where alkyl radicals can be monosubstituted or polysubstituted by fluorine;

$R^{24}$ is $(C_3-C_{12})$-cycloalkyl, $(C_3-C_{12})$-cycloalkyl-$(C_1-C_8)$-alkyl, $(C_6-C_{14})$-aryl, $(C_6-C_{14})$-aryl-$(C_1-C_8)$-alkyl, the radical Het- or Het-$(C_1-C_8)$-alkyl, where alkyl radicals can be monosubstituted or polysubstituted by fluorine;

$R^{25}$ has the meanings of $R^{23}$, where the radicals $R^{25}$ can be identical or different;

$R^{26}$ has the meanings of $R^{21}$ or $HO-((C_1-C_8)$-alkyl), where alkyl radicals can be monosubstituted or polysubstituted by fluorine;

$R^{27}$ is $(C_3-C_{12})$-cycloalkyl, $(C_3-C_{12})$-cycloalkyl-$(C_1-C_8)$-alkyl, $(C_6-C_{14})$-aryl-$(C_1-C_8)$-alkyl, the radical Het- or Het-$(C_1-C_8)$-alkyl, where alkyl radicals can be monosubstituted or polysubstituted by fluorine;

$R^{28}$ is one of the radicals $R^{21}-$, $R^{21}O-$, $R^{26}N(R^{26})-$, $R^{21}C(O)-$, $R^{21}O-C(O)-((C_1-C_{18})$-alkyl-$O-C(O)-((C_1-C_6)$-alkyl)$-O-C(O)-$, $R^{21}N(R^{21})-C(O)-$, $R^{21}N(R^{21})-C(=N(R^{21}))-$ or $R^{21}C(O)-N(R^{21})-$;

Het is a mono- or polycyclic, 4- to 14-membered aromatic or nonaromatic ring which contains 1, 2, 3 or 4 identical or different hereoatoms from the group consisting of N, O and S as ring members and can optionally be substituted by one or more, identical or different substituents;

b, c, d and f independently of one another are 0 or 1, but cannot all simultaneously be 0; e, g and h independently of one another are 0, 1, 2, 3, 4, 5 or 6;

in all their stereoisomeric forms and mixtures thereof in any ratio, and their physiologically tolerable salts.

Particularly preferred compounds of formula I are those in which simultaneously

W is $R^1$—A—CH=C and therein A is a phenylene radical or a methylenephenyl radical, or W is $R^1$—A—C($R^{13}$) and therein A is a bivalent radical from the group consisting of methylene, phenylenemethyl, methylenephenyl, methylenephenylmethyl;

B is a bivalent radical from the group consisting of methylene, ethylene, trimethylene, tetramethylene, vinylene, phenylene, or substituted methylene or ethylene;

E is $R^{10}CO$;

R is hydrogen, $(C_1-C_6)$-alkyl or benzyl;

$R^0$ is $(C_1-C_8)$-alkyl, $(C_3-C_8)$-cycloalkyl, optionally substituted $(C_6-C_{14})$-aryl or $(C_6-C_{14})$-aryl-$(C_1-C_8)$-alkyl optionally substituted in the aryl radical;

$R^1$ is one of the radicals $R^{21}O-$, $R^{24}NH-$, $R^{25}N(R^{25})-$, $HO-((C_1-C_8)$-alkyl)-$N(R^{26})-$, $R^{21}O-C(O)-$ and $R^{28}N(R^{21})-C(O)-$;

$R^2$ is hydrogen or $(C_1-C_8)$-alkyl;

$R^3$ is $(C_1-C_8)$-alkyl, optionally substituted $(C_6-C_{14})$-aryl, $(C_6-C_{14})$-aryl-$(C_1-C_8)$-alkyl, $(C_3-C_8)$-cycloalkyl, $(C_2-C_8)$-alkenyl, $(C_2-C_8)$-alkynyl, pyridyl, $R^{11}NH$, $R^4CO$, $COOR^4$, $CONHR^4$, $CSNHR^4$, $COOR^{15}$ and $CONHR^{15}$;

and e, g and h independently of one another are the numbers 0, 1, 2 or 3; in all their steroisomeric forms and mixtures thereof in any ratio, and their physiologically tolerable salts.

Very particularly preferred compounds of the formula I are those in which W is $R^1$—A—C($R^{13}$) and $R^{13}$ is $(C_1-C_6)$-alkyl, $(C_6-C_{14})$-aryl-$(C_1-C_8)$-alkyl optionally substituted in the aryl radical or $(C_3-C_8)$-cycloalkyl, in all their steroisomeric forms and mixtures thereof in any ratio, and their physiologically tolerable salts.

A series of specifically preferred compounds of the formula I are those in which $R^3$ is optionally substituted $(C_6-C_{14})$-aryl, $COOR^4$, $R^{11}NH$ or $CONHR^4$, where $-NHR^4$ is the radical of an α-amino acid, its ω-amino-$(C_2-C_8)$-alkylamide, its $(C_1-C_8)$-alkyl ester or its $(C_6-C_{14})$-aryl-$(C_1-C_4)$-alkyl ester, in all their stereoisomeric forms and mixtures thereof in any ratio, and their physiologically tolerable salts. The radical of an α-amino acid $-NHR^4$ is formally obtained by abstraction of a hydrogen atom from the amino group of the amino acid. It is specifically preferred in this series if $R^3$ is $CONHR^4$, where $-NHR^4$ is the radical of the α-amino acids valine, lysine, phenylglycine, phenylalanine or tryptophan or their $(C_1-C_8)$-alkyl esters or $(C_6-C_{14})$-aryl-$(C_1-C_4)$-alkyl esters.

Moreover preferred compounds of the formula I in this series are those in which simultaneously W is $R^1$—A—C($R^{13}$);

Y is a carbonyl group;

Z is $N(R^0)$;

A is ethylene, trimethylene, tetramethylene, pentamethylene, cyclohexylene, phenylene, phenylenemethyl, methylenephenyl or methylenephenylmethyl;

B is an unsubstituted or substituted methylene radical;

D is $C(R^2)(R^3)$;

E is $R^{10}CO$;

R is hydrogen or $(C_1-C_4)$-alkyl, in particular hydrogen, methyl or ethyl;

$R^0$ is $(C_1-C_8)$-alkyl, $(C_3-C_8)$-cycloalkyl, optionally substituted $(C_6-C_{14})$-aryl or $(C_6-C_{14})$-aryl-$(C_1-C_8)$-alkyl optionally substituted in the aryl radical;

$R^1$ is the radical $R^{28}N(R^{21})-C(O)-$;

$R^2$ is hydrogen;

$R^3$ is the radical $CONHR^4$;

$R^4$ is methyl which is substituted by hydroxycarbonyl and a radical from the group consisting of $(C_1-C_4)$-alkyl, phenyl and benzyl, or is methyl which is substituted by $(C_1-C_8)$-alkoxycarbonyl, preferably $(C_1-C_4)$-alkoxycarbonyl, and a radical from the group consisting of $(C_1-C_4)$-alkyl, phenyl and benzyl;

$R^{10}$ is hydroxyl or $(C_1-C_8)$-alkoxy, preferably $(C_1-C_4)$-alkoxy;

$R^{13}$ is $(C_1-C_6)$-alkyl, $(C_3-C_7)$-cycloalkyl or benzyl, in particular methyl;

b, c and d are 1 and e, f and g are 0;

h is 1 or 2, preferably 1;

in all their stereoisomeric forms and mixtures thereof in any ratio, and their physiologically tolerable salts.

If $-NHR^4$ is a $(C_1-C_8)$-alkyl ester of an α-amino acid or $R^4$ contains an alkoxycarbonyl radical, the methyl, ethyl, isopropyl, isobutyl or tert-butyl ester is preferred, if $-NHR^4$ is a $(C_6-C_{14})$-aryl-$(C_1-C_4)$-alkyl ester of an α-amino acid, the benzyl ester is preferred.

A further series of specifically preferred compounds of the formula I are those compounds in which simultaneously W is $R^1$—A—CH=C and therein A is a phenylene radical or a methylenephenyl radical, or W is $R^1$—A—C($R^{13}$) and therein A is a bivalent radical from the group consisting of methylene, ethylene, trimethylene, tetramethylene, pentamethylene, cyclohexylene, phenylene, phenylenemethyl, methylenephenyl, methylenephenylmethyl;

B is a bivalent radical from the group consisting of methylene, ethylene, trimethylene, tetramethylene, vinylene, phenylene or substituted methylene or ethylene;

E is $R^{10}$ CO;

R is hydrogen or $(C_1-C_6)$-alkyl;

$R^0$ is $(C_1-C_8)$-alkyl, $(C_3-C_8)$-cycloalkyl, optionally substituted $(C_6-C_{14})$-aryl or $(C_6-C_{14})$-aryl-$(C_1-C_8)$-alkyl optionally substituted in the aryl radical;

$R^1$ is $R^{21}O$—, $R^{21}O$—$N(R^{23})$—, $R^{24}NH$—, $R^{25}N(R^{25})$—, HO—$((C_1-C_8)$-alkyl)—$N(R^{26})$—, $R^{21}O$—$C(O)$— and $R^{28}N(R^{21})$—$C(O)$—;

$R^2$ is hydrogen or $(C_1-C_8)$-alkyl;

$R^3$ is $CONHR^{15}$ or $CONHR^4$ where $R^4$ herein is a $(C_1-C_8)$-alkyl radical which is unsubstituted or substituted by one or more $(C_6-C_{14})$-aryl radicals;

$R^{15}$ is $R^{16}$-$(C_1-C_6)$-alkyl or $R^{16}$, where $R^{16}$ is a 7- to 12-membered bridged bicyclic or tricyclic radical which is saturated or partially unsaturated and which can also contain one to four identical or different heteroatoms from the group consisting of nitrogen, oxygen and sulfur and which can also be substituted by one or more identical or different substituents from the group consisting of $(C_1-C_4)$-alkyl and oxo, and in particular $R^{15}$ is an adamantyl radical or an adamantylmethyl radical;

and e, g and h independently of one another are the numbers 0, 1, 2 or 3 and b, c and d are 1;

in all their stereoisomeric forms and mixtures thereof in any ratio, and their physiologically tolerable salts.

Moreover preferred compounds of the formula I in this series are those in which simultaneously W is $R^1$—A—$C(R^{13})$;

Y is a carbonyl group;

Z is $N(R^0)$;

A is ethylene, trimethylene, tetramethylene, pentamethylene, cyclohexylene, phenylene, phenylenemethyl, methylenephenyl or methylenephenylmethyl;

B is an unsubstituted or substituted methylene radical;

D is $C(R^2)(R^3)$;

E is $R^{10}CO$;

R is hydrogen or $(C_1-C_4)$-alkyl, in particular hydrogen, ethyl or ethyl;

$R^0$ is $(C_1-C_8)$-alkyl, $(C_3-C_8)$-cycloalkyl, optionally substituted $(C_6-C_{14})$-aryl or $(C_6-C_{14})$-aryl-$(C_1-C_8)$-alkyl optionally substituted in the aryl radical;

$R^1$ is the radical $R^{28}N(R^{21})$—$C(O)$—;

$R^2$ is hydrogen;

$R^3$ is $CONHR^{15}$ or $CONHR^4$ where $R^4$ herein is a $(C_1-C_6)$-alkyl radical which is unsubstituted or substituted by one or more $(C_6-C_{10})$-aryl radicals;

$R^{10}$ is hydroxyl or $(C_1-C_8)$-alkoxy, preferably $(C_1-C_4)$-alkoxy;

$R^{13}$ is $(C_1-C_6)$-alkyl, $(C_3-C_7)$-cycloalkyl or benzyl, in particular methyl;

$R^{15}$ is an adamantyl radical or an adamantylmethyl radical;

b, c and d are 1 and e, f and g are 0;

h is 1 or 2, preferably 1;

in all their stereoisomeric forms and mixtures thereof in any ratio, and their physiologically tolerable salts.

Furthermore, a series of specifically preferred compounds of the formula I are those in which simultaneously W is $R^1$—A—$C(R^{13})$;

Y is a carbonyl group;

Z is $N(R^0)$;

A is ethylene, trimethylene, tetramethylene, pentamethylene, cyclohexylene, phenylene, phenylenemethyl, methylenephenyl, methylenephenylmethyl;

B is an unsubstituted or substituted methylene radical or ethylene radical;

D is $C(R^2)(R^3)$;

E is $R^{10}CO$;

R is hydrogen or $(C_1-C_4)$-alkyl, in particular hydrogen, methyl or ethyl;

$R^0$ is $C_1-C_8$)-alkyl, $(C_3-C_8)$-cycloalkyl, optionally substituted $(C_6-C_{14})$-aryl or $(C_6-C_{14})$-aryl-$(C_1-C_8)$-alkyl which is optionally substituted in the aryl radical;

$R^1$ is one of the radicals $R^{21}O$—, $R^{24}NH$—, $R^{25}N(R^{25})$—, HO—$((C_1-C_8)$-alkyl)—$N(R^{26})$—, $R^{21}O$—$C(O)$—and $R^{28}N(R^{21})$—$C(O)$—;

$R^2$ is hydrogen;

$R^3$ is an unsubstituted phenyl radical or naphthyl radical, a phenyl radical or naphthyl radical substituted by one, two or three identical or different radicals from the group consisting of $(C_1-C_4)$-alkyl, $(C_1-C_4)$-alkoxy, hydroxyl, halogen, trifluoromethyl, nitro, methylenedioxy, ethylenedioxy, hydroxycarbonyl, $(C_1-C_4)$-alkoxycarbonyl, aminocarbonyl, cyano, phenyl, phenoxy and benzyloxy, a pyridyl radical, a $(C_1-C_4)$-alkyl radical, a $(C_2-C_4)$-alkenyl radical, a $(C_2-C_4)$-alkynyl radical or a $(C_5-C_6)$-cycloalkyl radical, and in particular $R^3$ is an unsubstituted or substituted phenyl radical or naphthyl radical;

$R^{10}$ is hydroxyl or $(C_1-C_8)$-alkoxy, in particular $(C_1-C_4)$-alkoxy, and preferably $R^{10}$ is a radical from the group consisting of hydroxyl, methoxy, ethoxy, propoxy and isopropoxy;

$R^{13}$ is $(C_1-C_6)$-alkyl, $(C_3-C_7)$-cycloalkyl or benzyl, in particular methyl;

b, c and d are 1 and e, f and g are 0;

h is 1 or 2, preferably 1;

in all their stereoisomeric forms and mixtures thereof in any ratio, and their physiologically tolerable salts.

Finally, a series of specifically preferred compounds of the formula I are those in which simultaneously W is $R^1$—A—$C(R^{13})$;

Y is a carbonyl group;

Z is $N(R^0)$;

A is ethylene, trimethylene, tetramethylene, pentamethylene, cyclohexylene, phenylene, phenylenemethyl, methylenephenyl, methylenephenylmethyl;

B is an unsubstituted or substituted methylene radical or ethylene radical;

D is $C(R^2)(R^3)$;

E is $R^{10}CO$;

R is hydrogen or $(C_1-C_4)$-alkyl, in particular hydrogen, methyl or ethyl;

$R^0$ is $(C_1-C_8)$-alkyl, $(C_3-C_8)$-cycloalkyl, optionally substituted $(C_6-C_{14})$-aryl or $(C_6-C_{14})$-aryl-$(C_1-C_8)$-alkyl optionally substituted in the aryl radical;

$R^1$ is one of the radicals $R^{21}O$—, $R^{24}NH$—, $R^{25}N(R^{25})$—, HO—$((C_1-C_8)$-alkyl)-$N(R^{26})$—, $R^{21}O$—$C(O)$— and $R^{28}N(R^{21})$—$C(O)$—;

$R^2$ is hydrogen;

$R^3$ is $R^{11}NH$;

$R^{10}$ is hydroxyl or $(C_1-C_8)$-alkoxy, in particular $(C_1-C_4)$-alkoxy, and preferably $R^{10}$ is a radical from the group consisting of hydroxyl, methoxy, ethoxy, propoxy and isopropoxy;

$R^{13}$ is $(C_1-C_6)$-alkyl, $(C_3-C_7)$-cycloalkyl or benzyl, in particular methyl;

b, c, d and e are 1 and f and g are 0;

h is 0;

in all their stereoisomeric forms and mixtures thereof in any ratio, and their physiologically tolerable salts.

Very specifically preferred compounds of the formula I are those in which a substituted methylene radical or substituted ethylene radical representing the group B carries as a substitutent a radical from the group consisting of $(C_1-C_8)$-alkyl, $(C_2-C_6)$-alkenyl, $(C_2-C_6)$-alkynyl, $(C_3-C_8)$-cycloalkyl, in particular $(C_5-C_6)$-cycloalkyl, $(C_3-C_8)$-cycloalkyl-$(C_1-C_4)$-alkyl, in particular $(C_5-C_6)$-cycloalkyl-$(C_1-C_4)$, optionally substituted $(C_6-C_{10})$-aryl, $(C_6-C_{10})$-aryl-$(C_1-C_4)$-alkyl optionally substituted in the aryl radical, optionally substituted heteroaryl and heteroaryl-$(C_1-C_4)$-alkyl optionally substituted in the heteroaryl radical, in all their stereoisomeric forms and mixtures thereof in any ratio, and their physiologically tolerable salts. Even more specifically preferred compounds of the formula I are those in which B is an unsubstituted methylene radical or a methylene radical which is substituted by a $(C_1-C_8)$-alkyl radical, in particular by a $(C_1-C_6)$-alkyl radical, in all their stereoisomeric forms and mixtures thereof in any ratio, and their physiologically tolerable salts.

Generally, compounds of the formula I are preferred which have a uniform configuration at chiral centers, e.g. at the chiral carbon atom representing D and at the center W in the 5-membered ring heterocycle in the formula I.

The compounds of the formula I can be prepared, for example, by fragment condensation of a

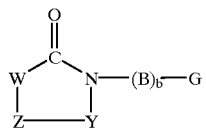

with a compounds of the formula III,

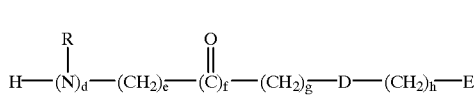

where W, Y, Z, B, D, E, R and b, d, e, f, g, and h are defined as indicated above and G is hydroxycarbonyl, $(C_1-C_6)$-alkoxycarbonyl, activated carboxylic acid derivatives, such as acid chloride or active esters, or isocyanato.

For the condensation of the compounds of the formula II with those of the formula III, the coupling methods of peptide chemistry known per se (see, for example, Houben-Weyl, Methoden der Organischen Chemie [Methods of organic chemistry], Volume 15/1 and 15/2, Georg Thieme Verlag, Stuttgart, 1974) are advantageously used. To do this, as a rule it is necessary that nonreacting amino groups present are protected by reversible protective groups during the condensation. The same applies to carboxyl groups not participating in the reaction, which are preferably present as $(C_1-C_6)$-alkyl, benzyl or tert-butyl esters. Amino group protection is unnecessary if the amino groups to be generated are still present as nitro or cyano groups and are formed, for example, by hydrogenation only after the coupling. After the coupling, the protective groups present are removed in a suitable manner. For example $NO_2$ groups (guanidino protection), benzyloxycarbonyl groups and benzyl esters can be removed by hydrogenation. The protective groups of the tert-butyl type are removed under acidic conditions, while the 9-fluorenylmethyloxycarbonyl radical is removed by secondary amines. The compounds of the formula I can also be prepared, for example, by synthesizing the compounds stepwise on a solid phase according to customary methods, as is illustrated by way of example below.

Compounds of the formula II in which W is $R^1$—A—C($R^{13}$), Y is a carbonyl group and Z is $NR^0$ can be prepared, for example, by first reacting compounds of the formula IV

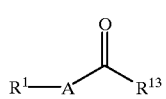

in a Bucherer reaction to give compounds of the formula V,

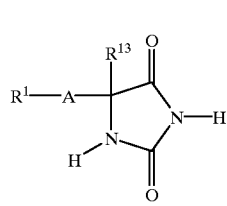

in which just as in the formula IV $R^1$, $R^{13}$ and A are defined as indicated above (H. T. Bucherer, V. A. Lieb, J. Prakt. Chem. 141(1934), 5). Compounds of the formula VI,

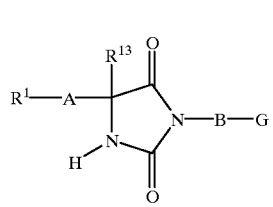

in which $R^1$, $R^{13}$, A, B and G are defined as indicated above can then be obtained by first reacting the compounds of the formula V, for example, with an alkylating reagent which introduces the radical -B-G into the molecule. The reaction of compounds of the formula VI with a second reagent of the formula $R^0$-LG, in which $R^0$ has the meanings indicated above and LG is a nucleophically substitutable leaving group, for example halogen, in particular chlorine or bromine, $(C_1-C_4)$-alkoxy, optionally substituted phenoxy or a heterocyclic leaving group such as, for example, imidazolyl, leads to the corresponding compounds of the formula II. these reactions can be carried out analogously to known methods familiar to the person skilled in the art. Depending on the individual case, it may be appropriate here, as in all steps in the synthesis of the compounds of the formula I, temporarily to block functional groups which could lead to side reactions or undesired reactions by means of a protective group strategy adapted to the synthesis problem, what is known to the person skilled in the art.

If W is $R^1$-A-CH=C, this structural element can be introduced, for example, by condensing an aldehyde with a 5-membered ring heterocycle which contains a methylene group in the position corresponding to the group W analogously to known methods.

Compounds of the formula I in which the 5-membered ring heterocycle in a dioxo- or thioxo-oxo-substituted imidazolidine ring in which W is $R^1$-A-C($R^{13}$) can also be obtained as follows:

By reaction of α-amino acids or N-substituted α-amino acids or preferably their esters, for example the methyl, ethyl, tert-butyl or benzyl esters, for example of a compound of the formula VII,

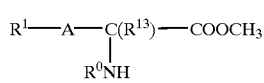
(VII)

in which $R^0$, $R^1$, $R^{13}$ and A are defined as indicated above, with an isocyanate or isothiocyanate, for example, of the formula VIII,

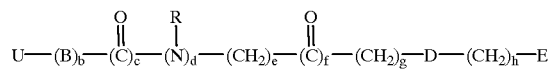
(VIII)

in which B, D, E and R and also b, c, d, e, f, g and h are defined as indicated above and U is isocyanato or isothiocyanato, there are obtained urea or thiourea derivatives, for example of the formula IX

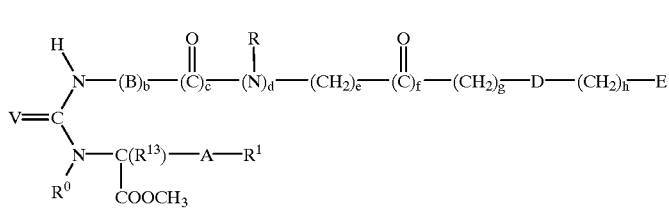
(IX)

for which the definitions indicated above apply and in which V is oxygen or sulfur, and which by heating with acid are cyclized with hydrolysis of the ester functions to give compounds of the formula Ia

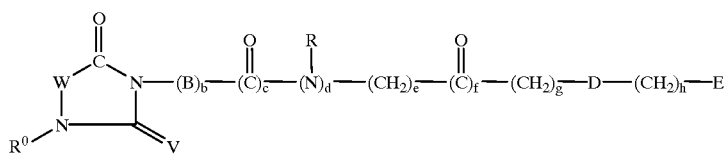
(Ia)

in which V is oxygen or sulfur, W is $R^1$-A-C($R^{13}$) and for which otherwise the meanings indicated above apply. The cyclization of the compounds of the formula IX to the compounds of the formula Ia can also be carried out by treatment with bases in inert solvents, for example by treatment with sodium hydride in an protic solvent such as dimethylformamide.

During the cyclization, guanidino groups can be blocked by protective groups, for example $NO_2$. Amino groups can be present in protected form or still as an $NO_2$ or cyano function which can later be reduced to the amino group or, in the case of the cyano group, also be converted into the formamidino group.

Compounds of the formula I in which the 5-membered ring heterocycle is a dioxo- or thioxo-oxo-substituted imidazolidine ring in which W is $R^1$-A-C($R^{13}$) and c is 1 can also be obtained by reacting a compound of the formula VII with an isocyanate or isothiocyanate of the formula X

(X)

in which B, U and b are defined as indicated above for the formula VIII and Q is an alkoxy group, for example a $(C_1-C_4)$-alkoxy group such as methoxy, ethoxy or tert-butoxy, a $(C_6-C_{14})$-aryloxy group, for example phenoxy, or a $(C_6-C_{14})$-aryl-$(C_1-C_4)$-alkoxy group, for example benzyloxy. In this case, a compound of the formula XI

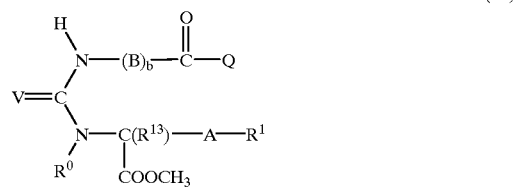
(XI)

is obtained in which A, B, V, Q, $R^0$, $R^1$, $R^{13}$ and b are defined as indicated above for the formulae IX and X, which is then cyclized under the influence of an acid or of a base, such as described above for the cyclization of the compounds of the formula IX, to a compound of the formula XII

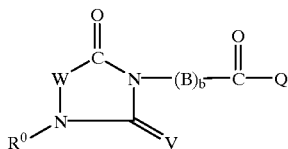

(XII)

in which B, Q, V, W, $R^0$ and b are defined as indicated bove for the formulae Ia and X. From the compound of the formula XII, a compound of the formula Ia is then obtained by hydrolysis of the group CO-Q to give the carboxylic acid COOH and subsequent coupling with a compound of the formula III, as described above for the coupling of the compounds of the formulae II and III. Here too, during the cyclization functional groups can be present in protected form or in the form of precursors, for example guanidino groups can be blocked by $NO_2$ or amino groups can be present in protected form or still as an $NO_2$ or cyano function which can later be reduced to the amino group or, in the case of the cyano group, also be converted into the formamidino group.

A further method for the preparation of compounds of the formula Ia is, for example, the reaction of compounds of the formula XIII, known from the literature, for example by partial hydrolysis under acidic or basic conditions.

With respect to the preparation of the compounds of the formula I, the disclosure of the following documents is fully incorporated by reference: WO-A-95/14008, German Patent Application 19635522.2 and the Patent Applications corresponding to it, for example European Patent Application 97103712.2 and U.S. patent application Ser. No. 08/821,253, as well as WO-A-96/33976.

The compounds of the formula I are antagonists of the adhesion receptor VLA-4. They have the ability to inhibit cell-cell and cell-matrix interaction processes in which interactions between VLA-4 and its ligands play a part. The activity of the compounds of the formula I can be demonstrated, for example, in an assay in which the binding of cells which contain the VLA-4 receptor, for example leucocytes, to ligands of this receptor is measured, for example to VCAM-1, which for this purpose can advantageously also be prepared by genetic engineering. Details of such an assay are described below. In particular, the compounds of the formula I are able to inhibit the adhesion and the migration of leucocytes, for example the adhesion of leucycytes to endothelial cells which—as explained above—is controlled via the VCAM-1/VLA-4-adhesion mechanism.

The compounds of the formula I and their physiologically tolerable salts are therefore suitable for the treatment and prophylaxis of diseases which are based on the interaction between the VLA-4 receptor and its ligands or can be influenced by inhibition of this interaction, and in particular (XIII)

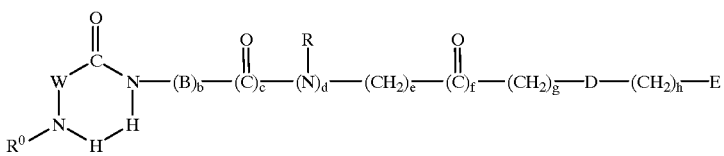

in which W is $R^1$-A-C($R^{13}$) and for which otherwise the definitions indicated above apply, with phosgene, thiophosgene or corresponding equivalents (analogously to S. Goldschmidt and M. Wick, Liebigs Ann. Chem. 575 (1952), 217–231 and C. Tropp, Chem. Ber. 61 (1928), 1431–1439).

A conversion of an amino function into a guanidino function can be carried out using the following reagents:

1. O-Methylisourea (S. Weiss and H. Krommer, Chemiker Zeitung 98 (1974), 617–618)
2. S-Methylisothiourea (R. F. Borne, M. I. Forrester and I. W. Waters, J. Med. Chem. 20 (1977), 771–776).
3. Nitro-S-methylisothiourea (L. S. Hafner and R. E. Evans, J. Org. Chem, 24 (1959) 57)
4. Formamidinosulfonic acid (K. Kim, Y. -T. Lin and H. S. Mosher, Tetrah. Lett. 29 (1988), 3183–3186)
5. 3,5-Dimethyl-1-pyrazolylformamidinium nitrate (F. L. Scott, D. G. O'Donovan and J. Reilly, J. Amer. Chem. Soc. 75 (1953), 4053–4054)
6. N,N'-Di-tert-butyloxycarbonyl-S-methylisothiourea (R. J. Bergeron and J. S. McManis, J. Org. Chem. 52 (1987), 1700–1703)
7. N-Alkoxycarbonyl-,N,N'-dialkoxycarbonyl-,N-alkylcarbonyl- and N,N'-dialkylcarbonyl-S-methylisothiourea (H. Wollweber, H. Kölling, E. Niemers, A. Widdig, P. Andrews, H. -P. Schultz and H. Thomas, Arzneim. Forsch./Drug Res. 34 (1984), 531–542).

Amides can be obtained, for example, from the corresponding nitriles (cyano compounds) according to methods they are suitable for the treatment and prophylaxis of diseases which are caused at least partially by an undesired extent of leucocyte adhesion and/or leucocyte migration or are associated therewith, and for whose prevention, alleviation or cure the adhesion and/or migration of leucocytes should be decreased. They can thus be employed, for example, as antiinflammatory agents in the case of inflammatory symptoms having very different causes. The compounds of the formula I according to the present invention are used, for example, for the treatment or prophylaxis of rheumatoid arthritis, inflammatory bowel disease (ulcerative colitis), systemic lupus erythematosus or for the treatment or prophylaxis of inflammatory disorders of the central nervous system, such as, for example, multiple schlerosis, for the treatment or prophylaxis of asthma or of allergies, for example allergies of the delayed type (type IV allergy), furthermore for the treatment or prophylaxis of cardiovascular disorders, arteriosclerosis, restenosis, for the treatment or prophylaxis of diabetes, for the prevention of damage to organ transplants, for the inhibition of tumor growth or tumor metastasis in various malignancies, for the therapy of malaria, and also of other diseases in which blocking of the integrin VLA-4 and/or influencing of the leucocyte activity appears appropriate for prevention, alleviation or cure. The compounds of the formula I and their salts can furthermore be employed for diagnostic purposes, e.g. in in vitro diagnoses, and as tools in biochemical investigations in which VLA-4 blocking or influencing of cell-cell or cell-matrix interactions is intended.

The compounds of formula I and their physiologically tolerable salts can be administered according to the invention, as pharmaceuticals for therapy or prophylaxis, to animals, preferably to mammals, and in particular to man. They can be administered per se, in mixtures with one another or in the form of pharmaceutical preparations which permit enteral or parenteral use and which as active constituent contain an efficacious dose of at least one compound of the formula I and/or its physiologically tolerable salts in addition to customary, pharmaceutically innocuous excipients and/or additives. The present invention also relates to the use of pharmaceutical preparations which contain one or more compounds of the formula I and/or their physiologically tolerable salts for the abovementioned inventive uses of the compounds of the formula I. The pharmaceutical preparations normally contain approximately 0.5 to 90% by weight of the therapeutically active compounds of the formula I and/or their physiologically tolerable salts.

The pharmaceuticals can be administered orally, for example in the form of pills, tablets, film-coated tablets, sugar-coated tablets, granules, hard and soft gelatin capsules, solutions, syrups, emulsions or suspensions. However, administration can also take place rectally, for example in the form of suppositories, or parenterally, for example in the form of injection or infusion solutions, microcapsules or rods, or percutaneously, for example in the form of ointments, or tinctures, or by other routes, for example in the form of nasal sprays or aerosol mixtures.

The pharmaceutical preparations to be employed according to the invention are prepared in a manner known per se, pharmaceutically inert inorganic and/or organic excipients being used in addition to the compound(s) of the formula I and/or its/their physiologically tolerable salts. For the production of pills, tablets, sugar-coated tablets and hard gelatin capsules, it is possible to use, for example, lactose, corn starch or derivatives thereof, talc, stearic acid or its salts, etc. Excipients for soft gelatin capsules and suppositories are, for example, fats, waxes, semisolid and liquid polyols, natural or hardened oils, etc. Suitable excipients for the preparation of solutions, for example injection solutions, or of emulsions or syrups are, for example, water, alcohols, glycerol, polyols, sucrose, invert sugar, glucose, vegetable oils, etc. Suitable excipients for microcapsules, implants or rods are, for example, copolymers of glycolic acid and lactic acid.

In addition to the active compounds and excipients the pharmaceutical preparations can additionally contain additives, such as, for example, fillers, disintegrants, binders, lubricants, wetting agents, stabilizers, emulsifiers, preservatives, sweeteners, colorants, flavorings or aromatizers, thickeners, diluents, buffer substances, and also solvents or solubilizers or agents for achieving a depot effect, as well as salts for changing the osmotic pressure, coatings or antioxidants. They can also contain two or more compounds of the formula I and/or their physiologically tolerable salts. In addition to at least one compound of the formula I and/or its physiologically tolerable salts, they can further contain one or more other therapeutically or prophylactically active substances, for example substances having antiinflammatory action.

The dose can vary within wide limits and is to be adapted to the individual conditions in each individual case. In general, in the case of oral administration a daily dose of approximately 0.01 to 100 mg/kg, preferably 0.1 to 10 mg/kg, in particular 0.3 to 2 mg/kg of body weight is adequate to achieve effective results. In the case of intravenous administration, the daily dose is in general approximately 0.01 to 50 mg/kg, preferably 0.01 to 10 mg/kg of body weight. The daily dose can be subdivided, in particular in the case of administration of relatively large amounts, into a number of, for example 2, 3 or 4, part administrations. Where appropriate, it may be necessary, depending on individual behavior, to deviate upwards or downwards from the indicated daily dose. Pharmaceutical preparations normally contain 0.2 to 500 mg, preferably 1 to 100 mg, of active compound of the formula I and/or its physiologically tolerable salts per dose.

Certain compounds of the formula I have not been explicitly disclosed in the prior art and represent a selection of the variety of compounds covered by the German Patent Application 19635522.2 and the Patent Applications corresponding to it. The present invention also relates to these novel compounds per se. The present invention thus also relates to compounds of the formula Ib per se,

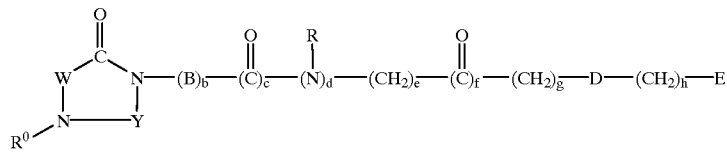

(Ib)

in which
W is $R^1$-A-C($R^{13}$) or $R^1$-A-CH=C;
Y is a carbonyl, thiocarbonyl or methylene group;
A is a bivalent radical from the group consisting of ($C_1$–$C_6$)-alkylene, ($C_3$–$C_{12}$)-cycloalkylene, ($C_1$–$C_6$)-alkylene-($C_3$–$C_{12}$)-cycloalkyl, phenylene, phenylene-($C_1$–$C_6$)-alkyl, ($C_1$–$C_6$)-alkylenephenyl, ($C_1$–$C_6$)-alkylenephenyl-($C_1$–$C_6$)-alkyl, phenylene-($C_2$–$C_6$)-alkenyl or a bivalent radical of a 5- or 6-membered saturated or unsaturated ring which can contain 1 or 2 nitrogen atoms and can be mono- or disubstituted by ($C_1$–$C_6$)-alkyl or doubly bonded oxygen or sulfur;
B is a bivalent radical from the group consisting of ($C_1$–$C_6$)-alkylene, ($C_2$–$C_6$)-alkenylene, phenylene, phenylene-($C_1$–$C_3$)-alkyl, ($C_1$–$C_3$)-alkylenephenyl;
D is C($R^2$)($R^3$), N($R^3$) or CH=C($R^3$);
E is tetrazolyl, ($R^8$O)$_2$P(O), HOS(O)$_2$, $R^9$NHS(O)$_2$ or $R^{10}$CO;
R and $R^0$ independently of one another are hydrogen, ($C_1$–$C_8$)-alkyl, ($C_3$–$C_{12}$)-cycloalkyl, ($C_3$–$C_{12}$)-cycloalkyl-($C_1$–$C_8$)-alkyl, optionally substituted ($C_6$–$C_{14}$)-aryl or ($C_6$–$C_{14}$)-aryl-($C_1$–$C_8$)-alkyl optionally substituted in the aryl radical, optionally substituted heteroaryl or heteroaryl-($C_1$–$C_8$)-alkyl optionally substituted in the heteroaryl radical, where alkyl radicals can be mono- or polysubstituted by fluorine;

$R^1$ is the radical $R^{28}N(R^{21})$—C(O)—;

$R^2$ is hydrogen, $(C_1-C_8)$-alkyl, optionally substituted $(C_6-C_{14})$-aryl, $(C_6-C_{14})$-aryl-$(C_1-C_8)$-alkyl optionally substituted in the aryl radical or $(C_3-C_8)$-cycloalkyl;

$R^3$ is hydrogen $(C_1-C_8)$-alkyl, optionally substituted $(C_6-C_{14})$-aryl, $(C_6-C_{14})$-aryl-$(C_1-C_8)$-alkyl optionally substituted in the aryl radical, $(C_3-C_8)$-cycloalkyl, $(C_2-C_8)$-alkenyl, $(C_2-C_8)$-alkynyl, $(C_2-C_8)$-alkenylcarbonyl, $(C_2-C_8)$-alkynylcarbonyl, pyridyl, $R^{11}NH$, $R^4CO$, $COOR^4$, $CON(CH_3)R^4$, $CONHR^4$, $CSNHR^4$, $COOR^{15}$, $CON(CH_3)R^{15}$ or $CONHR^{15}$;

$R^4$ is hydrogen or $(C_1-C_{28})$-alkyl which can optionally be mono- or polysubstituted by identical or different radicals from the group consisting of hydroxyl, hydroxycarbonyl, aminocarbonyl, mono- or di-$((C_1-C_{18})$-alkyl)aminocarbonyl, amino-$(C_2-C_{18})$-alkylaminocarbonyl, amino-$(C_1-C_3)$-alkylphenyl-$(C_1-C_3)$-alkylaminocarbonyl, $(C_1-C_{18})$-alkylcarbonylamino-$(C_1-C_3)$-alkylphenyl-$(C_1-C_3)$-alkylaminocarbonyl, $(C_1-C_{18})$-alkylcarbonylamino-$(C_2-C_{18})$-alkylaminocarbonyl, $(C_6-C_{14})$-aryl-$(C_1-C_8)$-alkoxycarbonyl which can also be substituted in the aryl radical, amino, mercapto, $(C_1-C_{18})$-alkoxy, $(C_1-C_{18})$-alkoxycarbonyl, optionally substituted $(C_3-C_8)$-cycloalkyl, $HOS(O)_2$-$(C_1-C_3)$-alkyl, $R^9NHS(O)_2$—$(C_1-C_3)$-alkyl, $(R^8O)_2P(O)$—$(C_1-C_3)$-alkyl, tetrazolyl-$(C_1-C_3)$-alkyl, halogen, nitro, trifluoromethyl or the radical $R^5$;

$R^5$ is optionally substituted $(C_6-C_{14})$-aryl, $(C_6-C_{14})$-aryl-$(C_1-C_8)$-alkyl optionally substituted in the aryl radical, a mono- or bicyclic 5- to 12-membered heterocyclic ring which can be aromatic, partially hydrogenated or completely hydrogenated and which can contain one, two or three identical or different heteroatoms from the group consisting of nitrogen, oxygen and sulfur, a radical $R^6$ or a radical $R^6CO$—, where the radical aryl and, independently thereof, the heterocyclic radical can be mono- or polysubstituted by identical or different radicals from the group consisting of $(C_1-C_{18})$-alkyl, $(C_1-C_{18})$-alkoxy, halogen, nitro, amino and trifluoromethyl;

$R^6$ is $R^7R^8N$, $R^7O$ or $R^7S$ or an amino acid side chain, a natural or unnatural amino acid, imino acid, optionally N—$(C_1-C_8)$-alkylated or N—$(C_6-C_{14})$-aryl-$(C_1-C_8)$-alkylated) azaamino acid or a dipeptide radical which can also be substituted in the aryl radical and/or in which the peptide bond can be reduced to —NH—CH$_2$—, and their esters and amides, where hydrogen or hydroxymethyl can optionally stand in place of free functional groups and/or where free functional groups can be protected by protective groups customary in peptide chemistry;

$R^7$ is hydrogen, $(C_1-C_{18})$-alkyl, $(C_6-C_{14})$-aryl-$(C_1-C_8)$-alkyl, $(C_1-C_{18})$-alkylcarbonyl, $(C_1-C_{18})$-alkoxycarbonyl, $(C_6-C_{14})$-arylcarbonyl, $(C_6-C_{14})$-aryl-$(C_1-C_8)$-alkylcarbonyl or $(C_6-C_{14})$-aryl-$(C_1-C_{18})$-alkyloxycarbonyl, where the alkyl groups can optionally be substituted by an amino group and/or where the aryl radicals can be mono- or polysubstituted, preferably monosubstituted, by identical or different radicals from the group consisting of $(C_1-C_8)$-alkyl, $(C_1-C_8)$-alkoxy, halogen, nitro, amino and trifluoromethyl, or is a natural or unnatural amino acid, imino acid, optionally N—$(C_1-C_8)$-alkylated or N—$(C_6-C_{14})$-aryl-$(C_1-C_8)$-alkylated) azaamino acid or a dipeptide radical which can also be substituted in the aryl radical and/or in which the peptide bond can be reduced to —NH—CH$_2$—;

$R^8$ is hydrogen, $(C_1-C_{18})$-alkyl, optionally substituted $(C_6-C_{14})$-aryl or $(C_6-C_{14})$-aryl-$(C_1-C_8)$-alkyl which can also be substituted in the aryl radical;

$R^9$ is hydrogen, aminocarbonyl, $(C_1-C_{18})$-alkylaminocarbonyl, $(C_3-C_8)$-cycloalkylaminocarbonyl, optionally substituted $(C_6-C_{14})$-arylaminocarbonyl, $(C_1-C_{18})$-alkyl, optionally substituted $(C_6-C_{14})$-aryl or $(C_3-C_8)$-cycloalkyl;

$R^{10}$ is hydroxy, $(C_1-C_{18})$-alkoxy, $(C_6-C_{14})$-aryl-$(C_1-C_8)$-alkoxy which can also be substituted in the aryl radical, optionally substituted $(C_6-C_{14})$-aryloxy, amino or mono- or di-$((C_1-C_{18})$-alkyl)amino;

$R^{11}$ is hydrogen, $(C_1-C_{18})$-alkyl, $R^{12}CO$, $R^{12a}CS$, optionally substituted $(C_6-C_{14})$-aryl-$S(O)_2$, $(C_1-C_{18})$-alkyl-S$(O)_2$, $(C_6-C_{14})$-aryl-$(C_1-C_8)$-alkyl optionally substituted in the aryl radical, $R^9NHS(O)_2$ or the radical $R^{15}$;

$R^{12}$ is hydrogen, $(C_1-C_{18})$-alkyl, $(C_2-C_8)$-alkenyl, $(C_2-C_8)$-alkynyl, optionally substituted $(C_6-C_{14})$-aryl, $(C_1-C_{18})$-alkoxy, $(C_6-C_{14})$-aryl-$(C_1-C_8)$-alkoxy, which can also be substituted in the aryl radical, optionally substituted $(C_6-C_{14})$-aryloxy, the radical $R^{15}$, the radical $R^{15}$—O—, amino, mono- or di-$((C_1-C_{18})$-alkyl)amino, $(C_2-C_8)$-alkenylamino, $(C_2-C_8)$-alkynylamino, $(C_3-C_{12})$-cycloalkylamino, $(C_3-C_{12})$-cycloalkyl-$(C_1-C_8)$-alkylamino, the radical $R^{15}$—NH—, optionally substituted $(C_6-C_{14})$-aryl-NH, $(C_6-C_{14})$-aryl-$(C_1-C_8)$-alkyl-NH, which can also be substituted in the aryl radical, optionally substituted heteroaryl-NH or heteroaryl-$(C_1-C_8)$-alkyl-NH optionally substituted in the heteroaryl radical;

$R^{12a}$ is amino, mono- or di-$((C_1-C_8)$-alkyl)amino, $(C_2-C_8)$-alkenylamino, $(C_2-C_8)$-alkynylamino, $(C_3-C_{12})$-cycloalkylamino, $(C_3-C_{12})$-cycloalkyl-$(C_1-C_8)$-alkylamino, the radical $R^{15}$—NH—, optionally substituted $(C_6-C_{14})$-aryl-NH, $(C_6-C_{14})$-aryl-$(C_1-C_8)$-alkyl-NH, which can also be substituted in the aryl radical, optionally substituted heteroaryl-NH or heteroaryl-$(C_1-C_8)$-alkyl-NH optionally substituted in the heteroaryl radical;

$R^{13}$ is hydrogen, $(C_1-C_6)$-alkyl, $(C_6-C_{14})$-aryl-$(C_1-C_8)$-alkyl optionally substituted in the aryl radical or $(C_3-C_8)$-cycloalkyl;

$R^{15}$ is $R^{16}$—$(C_1-C_6)$-alkyl or $R^{16}$;

$R^{16}$ is a 6- to 24-membered bicyclic or tricyclic radical which is saturated or partially unsaturated and which can also contain one to four identical or different heteroatoms from the group consisting of nitrogen, oxygen and sulfur and which can also be substituted by one or more identical or different substituents from the group consisting of $(C_1-C_4)$-alkyl and oxo;

$R^{21}$ is hydrogen, $(C_1-C_8)$-alkyl, $(C_3-C_{12})$-cycloalkyl, $(C_3-C_{12})$-cycloalkyl-$(C_1-C_8)$-alkyl, $(C_6-C_{14})$-aryl, $(C_6-C_{14})$-aryl-$(C_1-C_8)$-alkyl, the radical Het- or Het-$(C_1-C_8)$-alkyl, where alkyl radicals can be monosubstituted or polysubstituted by fluorine and the radicals $R^{21}$ can be identical or different if they occur several times;

$R^{26}$ has the meanings of $R^{21}$ or HO—$((C_1-C_8)$-alkyl), where alkyl radicals can be monosubstituted or polysubstituted by fluorine;

$R^{28}$ is one of the radicals $R^{21}$—, $R^{21}O$—, $R^{26}N(R^{26})$—, $R^{21}C(O)$—, $R^{21}O$—C(O)—, $((C_1-C_{18})$-alkyl-O—C(O)—$((C_1-C_6)$-alkyl)-O—C(O)—, $R^{21}N(R^{21})$—C(O)—, $R^{21}N(R^{21})$—C(=N($R^{21}$))— or $R^{21}C(O)$—N($R^{21}$)—;

Het is a mono- or polycyclic, 4- to 14-membered, aromatic or nonaromatic ring which contains, 1, 2, 3 or 4 identical or different heteroatoms from the group consisting of N, O and S as ring members and can optionally be substituted by one or more, identical or different substituents;

b, c, d and f independently of one another are 0 or 1, but cannot all simultaneously be 0;

e, g and h independently of one another are 0, 1, 2, 3, 4, 5 or 6;

in all their stereoisomeric forms and mixtures thereof in any ratio, and their physiologically tolerable salts.

All the above explanations for formula I, for example with respect to alkyl radicals, aryl radicals, etc., apply to the compounds of the formula Ib correspondingly. The above preferred meanings apply here correspondingly. In addition, particularly preferably, in the compounds of the formula Ib, independently of one another, b is 1, c is 1, d is 1, f is 0 and g is 0. e and h are particularly preferably independently of one another 0 or 1. It is also particularly preferred if Y is a carbonyl group. $R^{11}$ is particularly preferably hydrogen, $(C_1-C_{18})$-alkyl, $R^{12}CO$, optionally substituted $(C_6-C_{14})$-aryl-$S(O)_2$, $(C_1-C_{18})$-alkyl-$S(O)_2$, $(C_6-C_{14})$-aryl-$(C_1-C_8)$-alkyl optionally substituted in the aryl radical, $R^9NHS(O)_2$ or the radical $R^{15}$, where $R^{12}$ here is hydrogen, $(C_1-C_{18})$-alkyl, $(C_2-C_8)$-alkenyl, $(C_2-C_8)$-alkynyl, optionally substituted $(C_6-C_{14})$-aryl, $(C_1-C_{18})$-alkoxy, $(C_6-C_{14})$-aryl-$(C_1-C_8)$-alkoxy, which also be substituted in the aryl radical, optionally substituted $(C_6-C_{14})$-aryloxy, amino or mono- or di-$((C_1-C_{18})$-alkyl)amino, the radical $R^{15}$ or the radical $R^{15}$—O—.

The above explanations for the preparation of the compounds of the formula I and their use likewise also apply to the compounds of the formula Ib. These compounds, of course, are also inhibitors of leucocyte adhesion and/or antagonists of the VLA-4 receptor and are suitable for the treatment and prophylaxis of diseases which are caused by an undesired extent of leucocyte adhesion and/or leucocyte migration or which are associated therewith or in which cell-cell or cell-matrix interactions which are based on interactions of VLA-4 receptors with their ligands play a part, for example of inflammatory processes. The present invention furthermore relates to the compounds of the formula Ib for use as pharmaceuticals and to pharmaceutical preparations which contain one or more compounds of the formula Ib and/or their physiologically tolerable salts in addition to pharmaceutically innocuous excipients and/or additives.

Certain compounds of the formula I in which the group $R^1$-A contained in the group W contains no ring, but only acyclic structural elements, are not disclosed in the prior art. The present inventon also relates to these novel compounds per se. The present invention thus relates to compounds of the formula Ic per se, in which
W is $R^1$-A-$C(R^{13})$ or $R^1$-A-CH=C;
Y is a carbonyl, thiocarbonyl or methylene group;
Z is $N(R^0)$, oxygen, sulfur or a methylene group;
A is a bivalent $(C_1-C_6)$-alkylene radical;
B is a bivalent radical from the group consisting of $(C_1-C_6)$-alkylene, $(C_2-C_6)$-alkenylene, phenylene, phenylene-$(C_1-C_3)$-alkyl, $(C_1-C_3)$-alkylenephenyl;
D is $C(R^2)(R^3)$, $N(R^3)$ or CH=$C(R^3)$;
E is tetrazolyl, $(R^8O)_2$, $HOS(O)_2P(O)$, $R^9NHS(O)_2$ or $R^{10}CO$;

R and $R^0$ independently of one another are hydrogen $(C_1-C_8)$-alkyl, $(C_3-C_{12})$-cycloalkyl, $(C_3-C_{12})$-cycloalkyl-$(C_1-C_8)$-alkyl, optionally substituted $(C_6-C_{14})$-aryl, $(C_6-C_{14})$-aryl-$(C_1-C_8)$-alkyl optionally substituted in the aryl radical, optionally substituted heteroaryl or heteroaryl-$(C_1-C_8)$-alkyl optionally substituted in the heteroaryl radical, where alkyl radicals can be mono- or polysubstituted by fluorine;

$R^1$ is hydrogen, $(C_1-C_{10})$-alkyl, which can optionally be monosubstituted or polysubstituted by fluorine, or one of the radicals $R^{41}O$—, $R^{41}O$—$N(R^{42})$—, $R^{42}N(R^{42})$—, HO—$((C_1-C_8)$-alkyl)-$N(R^{43})$, HC(O)—NH—, $R^{41}C(O)$—$N(R^{42})$—, $R^{41}C(O)$—, $R^{41}O$—C(O)—, $R^{44}N(R^{41})$—C(O)—, $R^{41}O$—N=, O= and S=;

$R^2$ is hydrogen, $(C_1-C_8)$-alkyl, optionally substituted $(C_6-C_{14})$-aryl, $(C_6-C_{14})$-aryl-$(C_1-C_8)$-alkyl optionally substituted in the aryl radical or $(C_3-C_8)$-cycloalkyl;

$R^3$ is hydrogen, $(C_1-C_8)$-alkyl, optionally substituted $(C_6-C_{14})$-aryl, $(C_6-C_{14})$-aryl-$(C_1-C_8)$-alkyl optionally substituted in the aryl radical, $(C_3-C_8)$-cycloalkyl, $(C_2-C_8)$-alkenyl, $(C_2-C_8)$-alkynyl, $(C_2-C_8)$-alkenylcarbonyl, $(C_2-C_8)$-alkynylcarbonyl, pyridyl, $R^{11}NH$, $R^4CO$, $COOR^4$, $CON(CH_3)R^4$, $CONHR^4$, $CSNHR^4$, $COOR^{15}$, $CON(CH_3)R^{15}$ or $CONHR^{15}$;

$R^4$ is hydrogen or $(C_1-C_{28})$-alkyl which can optionally be mono- or polysubstituted by identical or different radicals from the group consisting of hydroxyl, hydroxycarbonyl, aminocarbonyl, mono- or di-$((C_1-C_{18})$-alkyl)aminocarbonyl, amino-$(C_2-C_{18})$-alkylaminocarbonyl, amino-$(C_1-C_3)$-alkylphenyl-$(C_1-C_3)$-alkylaminocarbonyl, $(C_1-C_{18})$-alkylcarbonylamino-$(C_1-C_3)$-alkylphenyl$(C_1-C_3)$-alkylaminocarbonyl, $(C_1-C_{18})$-alkylcarbonylamino-$(C_2-C_{18})$-alkylaminocarbonyl, $(C_6-C_{14})$-aryl-$(C_1-C_8)$-alkoxycarbonyl which can also be substituted in the aryl radical, amino, mercapto, $(C_1-C_{18})$-alkoxy, $(C_1-C_{18})$-alkoxycarbonyl, optionally substituted $(C_3-C_8)$-cycloalkyl, $HOS(O)_2$—$(C_1-C_3)$-alkyl, $R^9NHS(O)_2$—$(C_1-C_3)$-alkyl, $(R^8O)_2P(O)$—$(C_1-C_3)$-alkyl, tetrazolyl-$(C_1-C_3)$-alkyl, halogen, nitro, trifluoromethyl and the radical $R^5$;

$R^5$ is optionally substituted $(C_6-C_{14})$-aryl, $(C_6-C_{14})$-aryl-$(C_1-C_8)$-alkyl optionally substituted in the aryl radical,

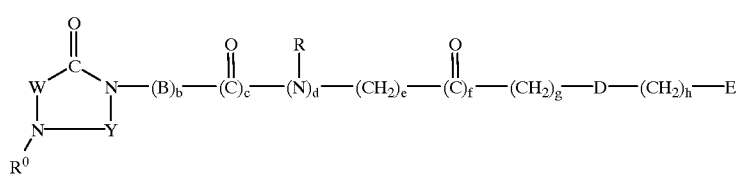

(Ic)

a mono- or bicyclic 5- to 12-membered heterocyclic ring which can be aromatic, partially hydrogenated or completely hydrogenated and which can contain one, two or three identical or different heteroatoms from the group consisting of nitrogen, oxygen and sulfur, a radical $R^6$ or a radical $R^6CO$—, where the aryl radical and, independently thereof, the heterocyclic radical can be mono- or polysubstituted by identical or different radicals from the group consisting of $(C_1-C_{18})$-alkyl, $(C_1-C_{18})$-alkoxy, halogen, nitro, amino or trifluoromethyl;

$R^6$ is $R^7R^8N$, $R^7O$ or $R^7S$ or an amino acid side chain, a natural or unnatural amino acid, imino acid, optionally N—$(C_1-C_8)$-alkylated or N—$(C_6-C_{14})$-aryl-$(C_1-C_8)$-alkylated) azaamino acid or a dipeptide radical which can also be substituted in the aryl radical and/or in which the peptide bond can be reduced to —NH—CH$_2$—, and their esters and amides, where hydrogen or hydroxymethyl can optionally stand in place of free functional groups and/or where free functional groups can be protected by protective groups customary in peptide chemistry;

$R^7$ is hydrogen, $(C_1-C_{18})$-alkyl, $(C_6-C_{14})$-aryl-$(C_1-C_8)$-alkyl, $(C_1-C_{18})$-alkylcarbonyl, $(C_1-C_{18})$-alkoxycarbonyl, $(C_6-C_{14})$-arylcarbonyl, $(C_6-C_{14})$-aryl-$(C_1-C_8)$-alkylcarbonyl or $(C_6-C_{14})$-aryl-$(C_1-C_{18})$-alkyloxycarbonyl, where the alkyl groups can optionally be substituted by an amino group and/or where the aryl radicals can be mono- or polysubstituted, preferably monosubstituted, by identical or different radicals from the group consisting of $(C_1-C_8)$-alkyl, $(C_1-C_8)$-alkoxy, halogen, nitro, amino and trifluoromethyl, or is a natural or unnatural amino acid, imino acid, optionally N—$(C_1-C_8)$-alkylated or N—$((C_6-C_{14})$-aryl-$(C_1-C_8)$-alkylated) azaamino acid or a dipeptide radical which can also be substituted in the aryl radical and/or in which the peptide bond can be reduced to —NH—CH$_2$—;

$R^8$ is hydrogen, $(C_1-C_{18})$-alkyl, optionally substituted $(C_6-C_{14})$-aryl or $(C_6-C_{14})$-aryl-$(C_1-C_8)$-alkyl which can also be substituted in the aryl radical;

$R^9$ is hydrogen, aminocarbonyl, $(C_1-C_{18})$-alkylaminocarbonyl, $(C_3-C_8)$-cycloalkylaminocarbonyl, optionally substituted $(C_6-C_{14})$-arylaminocarbonyl, $(C_1-C_{18})$-alkyl, optionally substituted $(C_6-C_{14})$-aryl or $(C_3-C_8)$-cycloalkyl;

$R^{10}$ is hydroxyl, $(C_1-C_{18})$-alkoxy, $(C_6-C_{14})$-aryl-$(C_1-C_8)$-alkoxy which can also be substituted in the aryl radical, optionally substituted $(C_6-C_{14})$-aryloxy, amino or mono- or di-$((C_1-C_{18})$-alkyl)amino;

$R^{11}$ is hydrogen, $(C_1-C_{18})$-alkyl, $R^{12}CO$, $R^{12a}CS$, optionally substituted $(C_6-C_{14})$-aryl-S(O)$_2$, $(C_1-C_{18})$-alkyl-S(O)$_2$, $(C_6-C_{14})$-aryl-$(C_1-C_8)$-alkyl optionally substituted in the aryl radical, $R^9NHS(O)_2$ or the radical $R^{15}$;

$R^{12}$ is hydrogen, $(C_1-C_{18})$-alkyl, $(C_2-C_8)$-alkenyl, $(C_2-C_8)$-alkynyl, optionally substituted $(C_6-C_{14})$-aryl, $(C_1-C_{18})$-alkoxy, $(C_6-C_{14})$-aryl-$(C_1-C_8)$-alkoxy which can also be substituted in the aryl radical, optionally substituted $(C_6-C_{14})$-aryloxy, the radical $R^{15}$, the radical $R^{15}$—O—, amino, mono- or di-$((C_1-C_{18})$-alkyl) amino, $(C_2-C_8)$-alkenylamino, $(C_2-C_8)$-alkynylamino, $(C_3-C_{12})$-cycloalkylamino, $(C_3-C_{12})$-cycloalkyl-$(C_1-C_8)$-alkylamino, the radical $R^{15}$—NH—, optionally substituted $(C_6-C_{14})$-aryl-NH, $(C_6-C_{14})$-aryl-$(C_1-C_8)$-alkyl-NH which can also be substituted in the aryl radical, optionally substituted heteroaryl-NH which can also be substituted in the aryl radical, optionally substituted heteroaryl-NH or heteroaryl-$(C_1-C_8)$-alkyl-NH optionally substituted in the heteroaryl radical;

$R^{12a}$ is amino, mono- or di-$((C_1-C_{18})$-alkyl)amino, $(C_2-C_8)$-alkenylamino, $(C_2-C_8)$-alkynylamino, $(C_3-C_{12})$-cycloalkylamino, $(C_3-C_{12})$-cycloalkyl-$(C_1-C_8)$-alkylamino, the radical $R^{15}$—NH—, optionally substituted $(C_6-C_{14})$-aryl-NH, $(C_6-C_{14})$-aryl-$(C_1-C_8)$-alkyl-NH, which can also be substituted in the aryl radical, optionally substituted heteroaryl-NH or heteroaryl-$(C_1-C_8)$-alkyl-NH optionally substituted in the heteroaryl radical;

$R^{13}$ is hydrogen, $(C_1-C_6)$-alkyl, $(C_6-C_{14})$-aryl-$(C_1-C_8)$-alkyl optionally substituted in the aryl radical or $(C_3-C_8)$-cycloalkyl;

$R^{15}$ is $R^{16}$—$(C_1-C_6)$-alkyl or $R^{16}$;

$R^{16}$ is a 6- to 24-membered bicyclic or tricyclic radical which is saturated or partially unsaturated and which can also contain one to four identical or different heteroatoms from the group consisting of nitrogen, oxygen and sulfur and which can also be substituted by one or more identical or different substituents from the group consisting of $(C_1-C_4)$-alkyl and oxo;

$R^{41}$ is hydrogen or $(C_1-C_8)$-alkyl, where alkyl radicals can be monosubstituted or polysubstituted by fluorine and the radicals $R^{41}$ can be identical or different if they occur several times;

$R^{42}$ is $(C_1-C_8)$-alkyl, where alkyl radicals can be monosubstituted or polysubstituted by fluorine and the radicals $R^{42}$ can be identical or different if they occur several times;

$R^{43}$ has the meanings of $R^{41}$ or is HO—$((C_1-C_8)$-alkyl), where alkyl radicals can be monosubstituted or polysubstituted by fluorine;

$R^{44}$ is one of the radicals $R^{41}$—, $R^{41}O$—, $R^{43}N(R^{43})$—, $R^{41}C(O)$—, $R^{41}O$—C(O)—, $((C_1-C_8)$-alkyl-O—C(O)—$((C_1-C_6)$-alkyl)-O—C(O)—, $R^{41}N(R^{41})$—C(O)—, $R^{41}N(R^{41})$—C(=N(R^{41}))— or $R^{41}C(O)$—N(R^{41})—;

b, c, d and f independently of one another are 0 or 1, but cannot all simultaneously be 0;

e, g and h independently of one another are 0, 1, 2, 3, 4, 5 or 6;

in all their stereoisomeric forms and mixtures thereof in any ratio, and their physiologically tolerable salts.

All the above explanations for the formula I, for example with respect to alkyl radicals, aryl radicals, etc., also apply to the compounds of the formula Ic correspondingly. The above preferred meanings also apply here correspondingly, In addition, particularly preferably, in the compounds of the formula Ic, independently of one another, b is 1, c is 1, d is 1, f is 0 and g is 0. e and h are particularly preferably independently of one another 0 or 1. It is also particularly preferred if Y is a carbonyl group, $R^{11}$ is preferably hydrogen, $(C_1-C_{18})$-alkyl, $R^{12}CO$, optionally substituted $(C_6-C_{14})$-aryl-S(O)$_2$, $(C_1-C_{18})$-alkyl-S(O)$_2$, $(C_6-C_{14})$-aryl-$(C_1-C_8)$-alkyl optionally substituted in the aryl radical, $R^9NHS(O)_2$ or the radical $R^{15}$, where $R^{12}$ here is hydrogen, $(C_1-C_{18})$-alkyl, $(C_2-C_8)$-alkenyl, $(C_2-C_8)$-alkynyl, optionally substituted $(C_6-C_{14})$-aryl, $(C_1-C_{18})$-alkoxy, $(C_6-C_{14})$-aryl-$(C_1-C_8)$-alkoxy, which can also be substituted in the aryl radical, optionally substituted $(C_6-C_{14})$-aryloxy, amino or mono- or di-$((C_1-C_{18})$-alkyl)amino, the radical $R^{15}$ or the radical $R^{15}$—O—.

The above explanations for the preparation of the compounds of the formula I and their use likewise also apply to the compounds of the formula Ic. These compounds, of course, are also inhibitors of leucocyte adhesion and/or antagonists of the VLA-4 receptor and are suitable for the treatment and prophylaxis of diseases which are caused by an undesired extent of leucocyte adhesion and/or leucocyte migration or which are associated therewith or in which cell-cell or cell-matrix interactions which are based on interactions of VLA-4 receptors with their ligands play a part, for example of inflammatory processes. The present invention furthermore relates to the compounds of the formula Ic for use as pharmaceuticals and to pharmaceutical preparations which contain one or more compounds of the formula Ic and/or their physiologically tolerable salts in addition to pharmaceutically innocuous excipients and/or additives.

Furthermore, in the prior art still no compounds of the formula I are disclosed in which b is 1 and B is a substituted alkylene radical. The present invention thus also relates to these compounds of the formula Id per se,

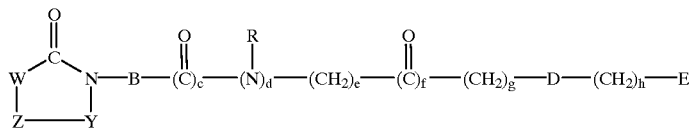

(Id)

in which

W is $R^1$-A-C($R^{13}$) or $R^1$-A-CH=C;

Y is a carbonyl, thiocarbonyl or methylene group;

Z is N($R^0$), oxygen, sulfur or a methylene group;

A is a bivalent radical from the group consnsting of ($C_1$–$C_6$)-alkylene, ($C_3$–$C_{12}$)-cycloalkylene, ($C_1$–$C_6$)-alkylene-($C_3$–$C_{12}$)-cycloalkyl, phenylene, phenylene-($C_1$–$C_6$)-alkyl, ($C_1$–$C_6$)-alkylenephenyl, ($C_1$–$C_6$)-alkylenephenyl-($C_1$–$C_6$)-alkyl, phenylene-($C_2$–$C_6$)-alkenyl or a bivalent radical of a 5- or 6-membered saturated or unsaturated ring which can contain 1 or 2 nitrogen atoms and can be mono-or disubstituted by ($C_1$–$C_6$)-alkyl or doubly bonded oxygen or sulfur;

B is a bivalent ($C_1$–$C_6$)-alkylene radical which is substituted by a radical from the group consisting of ($C_1$–$C_8$)-alkyl, ($C_2$–$C_8$)-alkenyl, ($C_2$–$C_8$)-alkynyl, ($C_3$–$C_{10}$)-cycloalkyl, ($C_3$–$C_{10}$)-cycloalkyl-($C_1$–$C_6$)-alkyl, optionally substituted ($C_6$–$C_{14}$)-aryl, ($C_6$–$C_{14}$)-aryl-($C_1$–$C_6$)-alkyl optionally substituted in the aryl radical, optionally substituted heteroaryl and heteroaryl-($C_1$–$C_6$)-alkyl optionally substituted in the heteroaryl radical;

D is C($R^2$)($R^3$), N($R^3$) or CH=C($R^3$);

E is tetrazolyl, ($R^8$O)$_2$P(O), HOS(O)$_2$, $R^9$NHS(O)$_2$ or $R^{10}$CO;

R is hydrogen, ($C_1$–$C_8$)-alkyl, ($C_3$–$C_{12}$)-cycloalkyl, ($C_3$–$C_{12}$)-cycloalkyl-($C_1$–$C_8$)-alkyl, optionally substituted ($C_6$–$C_{14}$)-aryl, ($C_6$–$C_{14}$)-aryl-($C_1$–$C_8$)-alkyl optionally substituted in the aryl radical, optionally substituted heteroaryl or heteroaryl-($C_1$–$C_8$)-alkyl optionally substituted in the heteroaryl radical, where alkyl radicals can be mono- or polysubstituted by fluorine;

$R^0$ is hydrogen, ($C_1$–$C_8$)-alkyl, ($C_3$–$C_{12}$)-cycloalkyl, ($C_3$–$C_{12}$)-cycloalkyl-($C_1$–$C_8$)-alkyl, ($C_6$–$C_{12}$)-bicycloalkyl, ($C_6$–$C_{12}$)-bicycloalkyl-($C_1$–$C_8$)-alkyl, ($C_6$–$C_{12}$)-tricycloalkyl, ($C_6$–$C_{12}$)-tricycloalkyl-($C_1$–$C_8$)-alkyl, optionally substituted ($C_6$–$C_{14}$)-aryl, ($C_6$–$C_{14}$)-aryl-($C_1$–$C_8$)-alkyl optionally substituted in the aryl radical, optionally substituted heteroaryl, heteroaryl-($C_1$–$C_8$)-alkyl optionally substituted in the heteroaryl radical, CHO, ($C_1$–$C_8$)-alkyl-CO, ($C_3$–$C_{12}$)-cycloalkyl-CO, ($C_3$–$C_{12}$)-cycloalkyl-($C_1$–$C_8$)-alkyl-CO, ($C_6$–$C_{12}$)-bicycloalkyl-CO, ($C_6$–$C_{12}$)-bicycloalkyl-($C_1$–$C_8$)-alkyl-CO, ($C_6$–$C_{12}$)-tricycloalkyl-CO, ($C_6$–$C_{12}$)-tricycloalkyl-($C_1$–$C_8$)-alkyl-CO, optionally substituted ($C_6$–$C_{14}$)-aryl-CO, ($C_6$–$C_{14}$)-aryl-($C_1$–$C_8$)-alkyl-CO optionally substituted in the aryl radical, optionally substituted heteroaryl-CO, heteroaryl-($C_1$–$C_8$)-alkyl-CO optionally substituted in the heteroaryl radical, ($C_1$–$C_8$)-alkyl-S(O)$_n$, ($C_3$–$C_{12}$)-cycloalkyl-S(O)$_n$, ($C_3$–$C_{12}$)-cycloalkyl-($C_1$–$C_8$)-alkyl-S(O)$_n$, ($C_6$–$C_{12}$)-bicycloalkyl-S(O)$_n$, ($C_6$–$C_{12}$)-bicycloalkyl-($C_1$–$C_8$)-alkyl-S(O)$_n$, ($C_6$–$C_{12}$)-tricycloalkyl-S(O)$_n$, ($C_6$–$C_{12}$)-tricycloalkyl-($C_1$–$C_8$)-alkyl-S(O)$_n$, optionally substituted ($C_6$–$C_{14}$)-aryl-S(O)$_n$, ($C_6$–$C_{14}$)-aryl-($C_1$–$C_8$)-alkyl-S(O)$_n$ optionally substituted in the aryl radical, optionally substituted heteroaryl —S(O)$_n$ or heteroaryl-($C_1$–$C_8$)-alkyl-S(O)$_n$ optionally substituted in the heteroaryl radical, where n is 1 or 2;

$R^1$ is hydrogen, ($C_1$–$C_{10}$)-alkyl, which can optionally be monosubstituted or polysubstituted by fluorine, ($C_3$–$C_{12}$)-cycloalkyl, ($C_3$–$C_{12}$)-cycloalkyl-($C_1$–$C_8$)-alkyl, optionally substituted $R^{21}$—(($C_6$–$C_{14}$)-aryl, ($R^{21}$—(($C_6$–$C_{14}$)-aryl))-($C_1$–$C_8$)-alkyl, optionally substituted in the aryl radical, the radical Het-, Het-($C_1$–$C_8$)-alkyl or one of the radicals $R^{21}$O—, $R^{22}$O—NH—, $R^{21}$O—N($R^{23}$)—, $R^{24}$NH—, $R^{25}$N($R^{25}$)—, HO—(($C_1$–$C_8$)-alkyl)—N($R^{26}$)—, $R^{27}$C(O)—NH—, $R^{21}$C(O)—N($R^{23}$)—, $R^{21}$C(O)—, $R^{21}$O—C(O)—, $R^{28}$N($R^{21}$)—C(O)—, $R^{21}$O—N=, O= and S=;

$R^2$ is hydrogen, ($C_1$–$C_8$)-alkyl, optionally substituted ($C_6$–$C_{14}$)-aryl, ($C_6$–$C_{14}$)-aryl-($C_1$–$C_8$)-alkyl optionally substituted in the aryl radical or ($C_3$–$C_8$)-cycloalkyl;

$R^3$ is hydrogen, ($C_1$–$C_8$)-alkyl, optionally substituted ($C_6$–$C_{14}$)-aryl, ($C_6$–$C_{14}$)-aryl-($C_1$–$C_8$)-alkyl optionally substituted in the aryl radical, ($C_3$–$C_8$)-cycloalkyl, ($C_2$–$C_8$)-alkenyl, ($C_2$–$C_8$)-alkynyl, ($C_2$–$C_8$)-alkenylcarbonyl, ($C_2$–$C_8$)-alkynylcarbonyl, pyridyl, $R^{11}$NH, $R^4$CO, COOR$^4$, CON(CH$_3$)R$^4$, CONHR$^4$, CSNHR$^4$, COOR$^{15}$, CON(CH$_3$)R$^{15}$ or CONHR$^{15}$;

$R^4$ is hydrogen or ($C_1$–$C_{28}$)-alkyl which can optionally be mono- or polysubstituted by identical or different radicals from the group consisting of hydroxyl, hydroxycarbonyl, aminocarbonyl, mono- or di-(($C_1$–$C_{18}$)-alkyl)aminocarbonyl, amino-($C_2$–$C_{18}$)-alkylaminocarbonyl, amino-($C_1$–$C_3$)-alkylphenyl-($C_1$–$C_3$)-alkylaminocarbonyl, ($C_1$–$C_{18}$)-alkylcarbonylamino-($C_1$–$C_3$)-alkylphenyl-($C_1$–$C_3$)-alkylaminocarbonyl, ($C_1$–$C_{18}$)-alkylcarbonylamino-($C_2$–$C_{18}$)-alkylaminocarbonyl, ($C_6$–$C_{14}$)-aryl-($C_1$–$C_8$)-alkoxycarbonyl which can also be substituted in the aryl radical, amino, mercapto, ($C_1$–$C_{18}$)-alkoxy, $(C_1-C_{18})$-alkoxycarbonyl, optionally substituted $(C_3-C_8)$-cycloalkyl, $HOS(O)_2$—$(C_1-C_3)$-alkyl, $R^9NHS(O)_2$—$(C_1-C_3)$-alkyl, $(R^8O)_2P(O)$—$(C_1-C_3)$-alkyl, tetrazolyl-$(C_1-C_3)$-alkyl, halogen, nitro, trifluoromethyl and the radical $R^5$;

$R^5$ is optionally substituted $(C_6-C_{14})$-aryl, $(C_6-C_{14})$-aryl-$(C_1-C_8)$-alkyl optionally substituted in the aryl radical, a mono- or bicyclic 5- to 12-membered heterocyclic ring which can be aromatic, partially hydrogenated or completely hydrogenated and which can contain one, two or three identical or different heteroatoms from the group consisting of nitrogen, oxygen and sulfur, a radical $R^6$ or a radical $R^6CO$—, where the aryl radical and, independently thereof, the heterocyclic radical can be mono- or polysubstituted by identical or different radicals from the group consisting of $(C_1-C_{18})$-alkyl, $(C_1-C_{18})$-alkoxy, halogen, nitro, amino and trifluoromethyl;

$R^6$ is $R^7R^8N$, $R^7O$ or $R^7S$ or an amino acid side chain, a natural or unnatural amino acid, imino acid, optionally N—$(C_1-C_8)$-alkylated or N—$((C_6-C_{14})$-aryl-$(C_1-C_8)$-alkylated) azaamino acid or a dipeptide radical which can also be substituted in the aryl radical and/or in which the peptide bond can be reduced to —NH—$CH_2$—, and their esters and amides, where hydrogen or hydroxymethyl can optionally stand in place of free functional groups and/or where free functional groups can be protected by protective groups customary in peptide chemistry;

$R^7$ is hydrogen, $(C_1-C_{18})$-alkyl, $(C_6-C_{14})$-aryl-$(C_1-C_8)$-alkyl, $(C_1-C_{18})$-alkylcarbonyl, $(C_1-C_{18})$-alkoxycarbonyl, $(C_6-C_{14})$-arylcarbonyl, $(C_6-C_{14})$-aryl-$(C_1-C_8)$-alkylcarbonyl or $(C_6-C_{14})$-aryl-$(C_1-C_{18})$-alkyloxycarbonyl, where the alkyl groups can optionally be substituted by an amino group snd/or where the aryl radicals can be mono- or polysubstituted, preferably monosubstituted, by identical or different radicals from the group consisting of $(C_1-C_8)$-alkyl, $(C_1-C_8)$-alkoxy, halogen, nitro, amino and trifluoromethyl, or is a natural or unnatural amino acid, imino acid, optionally N—$(C_1-C_8)$-alkylated or N—$((C_6-C_{14})$-aryl-$(C_1-C_8)$-alkylated) azaamino acid or a dipeptide radical which can also be substituted in the aryl radical and/or in which the peptide bond can be reduced to —NH—$CH_2$—;

$R^8$ is hydrogen, $(C_1-C_{18})$-alkyl, optionally substituted $(C_6-C_{14})$-aryl or $(C_6-C_{14})$-aryl-$(C_1-C_8)$-alkyl which can also be substituted in the aryl radical;

$R^9$ is hydrogen, aminocarbonyl, $(C_1-C_{18})$-alkylaminocarbonyl, $(C_3-C_8)$-cycloalkylaminocarbonyl, optionally substituted $(C_6-C_{14})$-arylaminocarbonyl, $(C_1-C_{18})$-alkyl, optionally substituted $(C_6-C_{14})$-aryl or $(C_3-C_8)$-cycloalkyl;

$R^{10}$ is hydroxyl, $(C_1-C_{18})$-alkoxy, $(C_6-C_{14})$-aryl-$(C_1-C_8)$-alkoxy which can also be substituted in the aryl radical, optionally substituted $(C_6-C_{14})$-aryloxy, amino or mono- or di-$((C_1-C_{18})$-alkyl)amino;

$R^{11}$ is hydrogen, $(C_1-C_{18})$-alkyl, $R^{12}CO$, $R^{12a}CS$, optionally substituted $(C_6-C_{14})$-aryl-$S(O)_2$, $(C_1-C_{18})$-alkyl-$S(O)_2$, $(C_6-C_{14})$-aryl-$(C_1-C_8)$-alkyl optionally substituted in the aryl radical, $R^9NHS(O)_2$ or the radical $R^{15}$;

$R^{12}$ is hydrogen, $(C_1-C_{18})$-alkyl, $(C_2-C_8)$-alkenyl, $(C_2-C_8)$-alkynyl, optionally substituted $(C_6-C_{14})$-aryl, $(C_1-C_{18})$-alkoxy, $(C_6-C_{14})$-aryl-$(C_1-C_8)$-alkoxy which can also be substituted in the aryl radical, optionally substituted $(C_6-C_{14})$-aryloxy, the radical $R^{15}$, the radical $R^{15}$—O—, amino, mono- or di-$((C_1-C_{18})$-alkyl)amino, $(C_2-C_8)$-alkenylamino, $(C_2-C_8)$-alkynylamino, $(C_3-C_{12})$-cycloalkylamino, $(C_3-C_{12})$-cycloalkyl-$(C_1-C_8)$-alkylamino, the radical $R^{15}$—NH—, optionally substituted $(C_6-C_{14})$-aryl-NH, $(C_6-C_{14})$-aryl-$(C_1-C_8)$-alkyl-NH, which can also be substituted in the aryl radical, optionally substituted heteroaryl-NH or heteroaryl-$(C_1-C_8)$-alkyl-NH optionally substituted in the heteroaryl radical;

$R^{12a}$ is amino, mono- or di-$((C_1-C_8)$-alkyl)amino, $(C_2-C_8)$-alkenylamino, $(C_2-C_8)$-alkynylamino, $(C_3-C_{12})$-cycloalkylamino, $(C_3-C_{12})$-cycloalkyl-$(C_1-C_8)$-alkylamino, the radical $R^{15}$—NH—, optionally substituted $(C_6-C_{14})$-aryl-NH, $(C_6-C_{14})$-aryl-$(C_1-C_8)$-alkyl-NH, which can also be substituted in the aryl radical, optionally substituted heteroaryl-NH or heteroaryl-$(C_1-C_8)$-alkyl-NH optionally substituted in the heteroaryl radical;

$R^{13}$ is hydrogen, $(C_1-C_6)$-alkyl, $(C_6-C_{14})$-aryl-$(C_1-C_8)$-alkyl optionally substituted in the aryl radical or $(C_3-C_8)$-cycloalkyl;

$R^{15}$ is $R^{16}$—$(C_1-C_6)$-alkyl or $R^{16}$;

$R^{16}$ is a 6- to 24-membered bicyclic or tricyclic radical which is saturated or partially unsaturated and which can also contain one to four identical or different heteroatoms from the group consisting of nitrogen, oxygen and sulfur and which can also be substituted by one or more identical or different substituents from the group consisting of $(C_1-C_4)$-alkyl and oxo;

$R^{21}$ is hydrogen, $(C_1-C_8)$-alkyl, $(C_3-C_{12})$-cycloalkyl, $(C_3-C_{12})$-cycloalkyl-$(C_1-C_8)$-alkyl, $(C_6-C_{14})$-aryl, $(C_6-C_{14})$-aryl-$(C_1-C_8)$-alkyl, the radical Het- or Het-$(C_1-C_8)$-alkyl, where alkyl radicals can be monosubstituted or polysubstituted by fluorine and the radicals $R^{21}$ can be identical or different if they occur several times;

$R^{22}$ is $(C_3-C_{12})$-cycloalkyl, $(C_3-C_{12})$-cycloalkyl-$(C_1-C_8)$-alkyl, $(C_6-C_{14})$-aryl, the radical Het- or Het-$(C_1-C_8)$-alkyl, where alkyl radicals can be monosubstituted or polysubstituted by fluorine;

$R^{23}$ is $(C_1-C_8)$-alkyl, $(C_3-C_{12})$-cycloalkyl, $(C_3-C_{12})$-cycloalkyl-$(C_1-C_8)$-alkyl, $(C_6-C_{14})$-aryl, $(C_6-C_{14})$-aryl-$(C_1-C_8)$-alkyl, the radical Het- or Het-$(C_1-C_8)$-alkyl, where alkyl radicals can be monosubstituted or polysubstituted by fluorine;

$R^{24}$ is $(C_3-C_{12})$-cycloalkyl, $(C_3-C_{12})$-cycloalkyl-$(C_1-C_8)$-alkyl, $(C_6-C_{14})$-aryl, $(C_6-C_{14})$-aryl-$(C_1-C_8)$-alkyl, the radical Het- or Het-$(C_1-C_8)$-alkyl, where alkyl radicals can be monosubstituted or polysubstituted by fluorine;

$R^{25}$ has the meanings of $R^{23}$, where the radicals $R^{25}$ can be identical or different;

$R^{26}$ has the meanings of $R^{21}$ or HO—$((C_1-C_8)$-alkyl), where alkyl radicals can be monosubstituted or polysubstituted by fluorine;

$R^{27}$ is hydrogen, $(C_3-C_{12})$-cycloalkyl, $(C_3-C_{12})$-cycloalkyl-$(C_1-C_8)$-alkyl, $(C_6-C_{14})$-aryl-$(C_1-C_8)$-alkyl, the radical Het- or Het-$(C_1-C_8)$-alkyl, where alkyl radicals can be monosubstituted or polysubstituted by fluorine;

$R^{28}$ is one of the radicals $R^{21}$—, $R^{21}O$—, $R^{26}N(R^{26})$—, $R^{21}C(O)$—, $R^{21}O$—$C(O)$—, $((C_1-C_{18})$-alkyl-O—C(O)—$((C_1-C_6)$-alkyl)-O—C(O)—, $R^{21}N(R^{21})$—C(O)—, $R^{21}N(R^{21})$—C(=N$(R^{21})$)— or $R^{21}C(O)$—N$(R^{21})$—;

Het is a mono- or polycyclic, 4- to 14-membered, aromatic or nonaromatic ring which contains 1, 2, 3 or 4 identical or different heteroatoms from the group consisting of N, O and S as ring members and can optionally be substituted by one or more, identical or different substituents;

c, d and f independently of one another are 0 or 1, but cannot all simultaneously be 0;

e, g and h independently of one another are 0, 1, 2, 3, 4, 5 or 6;

in all their stereoisomeric forms and mixtures thereof in any ratio, and their physiologically tolerable salts.

All above explanations for the formula I, for example with respect to alkyl radicals, aryl radicals, etc. also apply to the compounds of the formula Id correspondingly. The above preferred meanings also apply here correspondingly. In addition, particularly preferably, in the compounds of the formula Id, independently of one another, c is 1, d is 1, f is 0 and g is 0. e and h are particularly preferably independently of one another 0 or 1. It is also particularly preferred if Y is a carbonyl group. With respect to the group B, in addition the following applies to the compounds of the formula Id.

The $(C_1-C_6)$-alkylene radical representing the group B in the compounds of the formula Id is preferably a $(C_1-C_4)$-alkylene radical, particularly preferably a methylene radical or an ethylene radical )=1,2-ethylene), very particularly preferably a methylene radical. The substituent on the group B can on the one hand contain a cyclic system when it is a substituent from the group consisting of $(C_3-C_{10})$-cycloalkyl, $(C_3-C_{10})$-cycloalkyl-$(C_1-C_6)$-alkyl, optionally substituted $(C_6-C_{14})$-aryl, $(C_6-C_{14})$-aryl-$(C_1-C_6)$-alkyl optionally substituted in the aryl radical, optionally substituted heteroaryl and heteroaryl-$(C_1-C_6)$-alkyl optionally substituted in the heteroaryl radical, and can on the other hand be acyclic when it is a substituent from the group consisting of $(C_1-C_8)$-alkyl, $(C_2-C_8)$-alkenyl and $(C_2-C_8)$-alkynyl. These acyclic substituents can each contain 2, 3, 4, 5, 6, 7 or 8 carbon atoms or, in the case of the saturated alkyl radical, also 1 carbon atom. In the case of the alkenyl radicals and alkynyl radicals, the double bond or triple bond can be located in any desired position and in the case of the double bond can have the cis configuration or trans configuration. As explained above, these alkyl radicals, alkenyl radicals and alkynyl radicals can be straight-chain or branched.

As examples of substituenst which the $(C_1-C_6)$-alkylene radical representing B can carry the following are mentioned: methyl, ethyl, n-proply, n-butyl, n-pentyl, n-hexyl, n-heptyl, n-octyl, isopropyl, isobutyl, isopentyl, isohexyl, sec-butyl, tert-butyl, tert-pentyl, neopentyl, neohexyl, 3-methylpentyl, 2-ethylbutyl, vinyl, allyl, 1-propenyl, 2-butenyl, 3-butenyl, 3-methyl-2-butenyl, ethynyl, 1-propynyl, 2-propynyl, 6-hexynyl, phenyl, benzyl, 1-phenylethyl, 2-phenylethyl, 3-phenylpropyl, 4-biphenylylmethyl, cyclopropyl, cyclopropylmethyl, cyclopentyl, cyclohexyl, cyclohexylmethyl, 2-cyclohexylethyl, 3-cyclooctylpropyl, 2-pyridyl, 3-pyridyl, 4-pyridyl, 4-pyridylmethyl, 2-(4-pyridyl)ethyl, 2-furylmethyl, 2-thienylmethyl, 3-thienylmethyl or 2-(3-Indolyl)ethyl. Preferably, the substituent which the $(C_1-C_6)$-alkylene radical representing B can carry, is a $(C_1-C_8)$-alkyl radical.

Preferred compounds of the formula Id are those in which simultaneously

W is $R^1A-C(R^{13})$;

Y is a carbonyl group;

Z is $N(R^0)$;

A is a bivalent radical from the group consisting of $(C_3-C_7)$-cycloalkylene, phenylene, phenylene-$(C_1-C_6)$-alkyl, $(C_1-C_6)$-alkylenephenyl or a bivalent radical of a 5- or 6-membered saturated or unsaturated ring which can contain 1 or 2 nitrogen atoms and can be mono- or disubstituted by $(C_1-C_6)$-alkyl or doubly bonded oxygen or sulfur;

B is a bivalent methylene radical or ethylene radical which is substituted by a radical from the group consisting of $(C_1-C_8)$-alkyl, $(C_2-C_8)$-alkenyl, $(C_2-C_8)$-alkynyl, $(C_3-C_{10})$-cycloalkyl, $(C_3-C_{10})$-cycloalkyl-$(C_1-C_6)$-alkyl, optionally substituted $(C_6-C_{14})$-aryl, $(C_6-C_{14})$-aryl-$(C_1-C_6)$-alkyl optionally substituted in the aryl radical, optionally substituted heteroaryl and heteroaryl-$(C_1-C_6)$-alkyl optionally substituted in the heteroaryl radical;

D is $C(R^2)(R^3)$;

E is tetrazolyl or $R^{10}CO$;

R is hydrogen or $(C_1-C_8)$-alkyl;

$R^0$ is hydrogen, $(C_1-C_8)$-alkyl, $(C_3-C_{12})$-cycloalkyl, $(C_3-C_{12})$-cycloalkyl-$(C_1-C_8)$-alkyl, $(C_6-C_{12})$-bicycloalkyl, $(C_6-C_{12})$-bicycloalkyl-$(C_1-C_8)$-alkyl, $(C_6-C_{12})$-tricycloalkyl, $(C_6-C_{12})$-tricycloalkyl-$(C_1-C_8)$-alkyl, optionally substituted $(C_6-C_{14})$-aryl, $(C_6-C_{14})$-aryl-$(C_1-C_8)$-alkyl optionally substituted in the aryl radical, optionally substituted heteroaryl, heteroaryl-$(C_1-C_8)$-alkyl, optionally substituted in the heteroaryl radical, CHO, $(C_1-C_8)$-alkyl-CO, $(C_3-C_{12})$-cycloalkyl-CO, $(C_3-C_{12})$-cycloalkyl-$(C_1-C_8)$-alkyl-CO, $(C_6-C_{12})$-bicycloalkyl-CO, $(C_6-C_{12})$-bicycloalkyl-$(C_1-C_8)$-alkyl-CO, $(C_6-C_{12})$-tricycloalkyl-CO, $(C_6-C_{12})$-tricycloalkyl-$(C_1-C_8)$-alkyl-CO, optionally substituted $(C_6-C_{14})$-aryl-CO, $(C_6-C_{14})$-aryl-$(C_1-C_8)$-alkyl-CO optionally substituted in the aryl radical, optionally substituted heteroaryl-CO, heteroaryl-$(C_1-C_8)$-alkyl-CO optionally substituted in the heteroaryl radical, $(C_1-C_8)$-alkyl-$S(O)_n$, $(C_3-C_{12})$-cycloalkyl-$S(O)_n$, $(C_3-C_{12})$-cycloalkyl-$(C_1-C_8)$-alkyl-$S(O)_n$, $(C_6-C_{12})$-bicycloalkyl-$S(O)_n$, $(C_6-C_{12})$-bicycloalkyl-$(C_1-C_8)$-alkyl-$S(O)_n$, $(C_6-C_{12})$-tricycloalkyl-$S(O)_n$, $(C_6-C_{12})$-tricycloalkyl-$(C_1-C_8)$-alkyl-$S(O)_n$ optionally substituted in the aryl radical, optionally substituted heteroaryl $S(O)_n$ or heteroaryl-$(C_1-C_8)$-alkyl-$S(O)_n$ optionally substituted in the heteroaryl radical, where n is 1 or 2;

$R^1$ is one of the radicals $R^{21}O-$, $R^{24}HN-$, $R^{25}N(R^{25})-$, $HO-((C_1-C_8)$-alkyl)-$N(R^{26})-$, $R^{21}O-C(O)-$ and $R^{28}N(R^{21})-C(O)-$;

$R^2$ is hydrogen or $(C_1-C_8)$-alkyl;

$R^3$ is hydrogen, $(C_1-C_8)$-alkyl, optionally substituted $(C_6-C_{14})$-aryl, $(C_6-C_{14})$-aryl-$(C_1-C_8)$-alkyl optionally substituted in the aryl radical, $(C_3-C_8)$-cycloalkyl, $(C_2-C_8)$-alkenyl, $(C_2-C_8)$-alkynyl, $(C_2-C_8)$-alkenylcarbonyl, $(C_2-C_8)$-alkynylcarbonyl, pyridyl, $R^{11}NH$, $CON(CH_3)R^4$, $CONHR^4$, $CON(CH_3)R^{15}$ or $CONHR^{15}$;

$R^4$ is $(C_1-C_{10})$-alkyl, which can optionally be mono- or polysubstituted by identical or different radicals from the group consisting of hydroxyl, hydroxylcarbonyl, aminocarbonyl, mono- or di-$((C_1-C_{18})$-alkyl) aminocarbonyl, $(C_6-C_{14})$-aryl-$(C_1-C_8)$-alkoxycarbonyl, which can also be substituted in the aryl radical, $(C_1-C_8)$-alkoxy, $(C_1-C_8)$-alkoxycarbonyl, optionally substituted ($C_3$–$C_8$)-cycloalkyl, tetrazolyl-($C_1$–$C_3$)-alkyl, trifluoromethyl and $R^5$;

$R^5$ is optionally substituted ($C_6$–$C_{14}$)-aryl, ($C_6$–$C_{14}$)-aryl-($C_1$–$C_8$)-alkyl optionally substituted in the aryl radical, a mono- or bicyclic 5- to 12-membered heterocyclic ring which can be aromatic, partially hydrogenated or completely hydrogenated and which can contain one, two or three identical or different heteroatoms from the group consisting of nitrogen, oxygen and sulfur, or a radical $R^6$CO—, where the aryl radical and, independently thereof, the heterocyclic radical, can be mono- or polysubstituted by identical or different radicals from the group consisting of ($C_1$–$C_8$)-alkyl, ($C_1$–$C_8$)-alkoxy, halogen, nitro, amino or trifluoromethyl;

$R^6$ is a natural or unnatural amino acid, imino acid, optionally N—($C_1$–$C_8$)-alkylated or N—(($C_6$–$C_{14}$)-aryl-($C_1$–$C_8$)-alkylated) azaamino acid or a dipeptide radical which can also be substituted in the aryl radical, and their esters and amides, where free functional groups can be protected by protective groups customary in peptide chemistry;

$R^{10}$ is hydroxyl, ($C_1$–$C_{18}$)-alkoxy, ($C_6$–$C_{14}$)-aryl-($C_1$–$C_8$)-alkoxy which can also be substituted in the aryl radical, optionally substituted ($C_6$–$C_{14}$)-aryloxy, amino or mono- or di-(($C_1$–$C_{18}$)-alkyl)amino;

$R^{11}$ is $R^{12}$CO, optionally substituted ($C_6$–$C_{14}$)-aryl-S(O)$_2$ or ($C_1$–$C_{18}$)-alkyl-S(O)$_2$;

$R^{12}$ is hydrogen, ($C_1$–$C_{18}$)-alkyl, ($C_2$–$C_8$)-alkenyl, ($C_2$–$C_8$)-alkynyl, optionally substituted ($C_6$–$C_{14}$)-aryl, ($C_1$–$C_{18}$)-alkoxy, ($C_6$–$C_{14}$)-aryl-($C_1$–$C_8$)-alkoxy which can also be substituted in the aryl radical or optionally substituted ($C_6$–$C_{14}$)-aryloxy, the radical $R^{15}$ or the radical $R^{15}$—O—;

$R^{13}$ is hydrogen or ($C_1$–$C_4$)-alkyl;

$R^{15}$ is $R^{16}$—($C_1$–$C_6$)-alkyl or $R^{16}$;

$R^{16}$ is a 6- to 24-membered bicyclic or tricyclic radical which is saturated or partially unsaturated and which can also contain one to four indentical or different heteroatoms from the group consisting of nitrogen, oxygen and sulfur and which can also be substituted by one or more identical or different substituents from the group consisting of ($C_1$–$C_4$)-alkyl and oxo;

c and d are 1 and f is 0;

e and h independently of one another are 0 and 1 and g is 0;

in all their stereoisomeric forms and mixtures thereof in any ratio, and their physiologically tolerable salts.

Particularly preferred compounds of the formula Id are, on the one hand, those in which the radical by which the group B is substituted is a ($C_1$–$C_8$)-alkyl radical, in all their stereoisomeric forms and mixtures thereof in any ratio, and their physiologically tolerable salts. On the other hand, particularly preferred compounds of the formula Id are those in which the radical $R^1$ is $R^{28}$N($R^{21}$)—C(O)—, in all their stereoisomeric forms and mixtures thereof in any ratio, and their physiologically tolerable salts.

The above explanations for the preparation of the compounds of the formula I and their use likewise also apply to the compounds of the formula Id. These compounds, of course, are also inhibitors of leucocyte adhesion and/or antagonists of the VLA-4 receptor and are suitable for the treatment and prophylaxis of diseases which are caused by an undesired extent of leucocyte adhesion and/or leucocyte migration or which are associated therewith or in which cell-cell or cell-matrix interactions which are based on interactions of VLA-4 receptors with their ligands play a part, for example of inflammatory processes. The present invention furthermore relates to the compounds of the formula Id for use as pharmaceuticals and to pharmaceutical preparations which contain one or more compounds of the formula Id and/or their physiologically tolerable salts in addition to pharmaceutically innocuous excipients and/or additives, the above explanations also applying in turn to these pharmaceutical preparations.

In the prior art, no compounds of the formula I are disclosed in which $R^0$ is a sulfonyl radical or sulfinyl radical, or in which $R^0$ is an acyl radical which contains heteroaryl radical. The present invention thus furthermore also relates to compounds of the formula Ie per se,

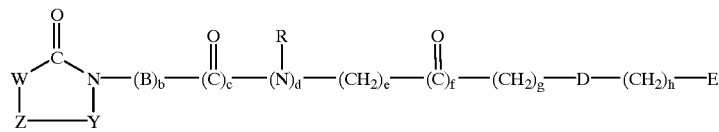

(Ie)

in which

W is $R^1$-A-C($R^{13}$) or $R^1$-A-CH=C;

Y is a carbonyl, thiocarbonyl or methylene group;

Z is N($R^0$), oxygen, sulfur or a methylene group;

A is a bivalent radical from the group consisting of ($C_1$–$C_6$)-alkylene, ($C_3$–$C_{12}$)-cycloalkylene, ($C_1$–$C_6$)-alkylene-($C_3$–$C_{12}$)-cycloalkyl, phenylene, phenylene-($C_1$–$C_6$)-alkyl, ($C_1$–$C_6$)-alkylenephenyl, ($C_1$–$C_6$)-alkylenephenyl-($C_1$–$C_6$)-alkyl, phenylene-($C_2$–$C_6$)-alkenyl or a bivalent radical of a 5- or 6-membered saturated or unsaturated ring which can contain 1 or 2 nitrogen atoms and can be mono- or disubstituted by ($C_1$–$C_6$)-alkyl or doubly bonded oxygen or sulfur;

B is a bivalent radical from the group consisting of ($C_1$–$C_6$)-alkylene, ($C_2$–$C_6$)-alkenylene, phenylene, phenylene-($C_1$–$C_3$)-alkyl, ($C_1$–$C_3$)-alkylenephenyl;

D is C($R^2$)($R^3$), N($R^3$) or CH=C($R^3$);

E is tetrazolyl, ($R^8$O)$_2$P(O), HOS(O)$_2$, $R^9$NHS(O)$_2$ or $R^{10}$CO;

R is hydrogen, ($C_1$–$C_8$)-alkyl, ($C_3$–$C_{12}$)-cycloalkyl, ($C_3$–$C_{12}$)-cycloalkyl-($C_1$–$C_8$)-alkyl, optionally substituted ($C_6$–$C_{14}$)-aryl, ($C_6$–$C_{14}$)-aryl-($C_1$–$C_8$)-alkyl optionally substituted in the aryl radical, optionally substituted heteroaryl or heteroaryl-($C_1$–$C_8$)-alkyl optionally substituted in the heteroaryl radical, where alkyl radicals can be mono- or polysubstituted by fluorine;

$R^0$ is optionally substituted heteroaryl-CO, heteroaryl-($C_1$–$C_8$)-alkyl-CO optionally substituted in the heteroaryl radical, ($C_1$–$C_8$)-alkyl-S(O)$_n$, ($C_3$–$C_{12}$)-cycloalkyl-S(O)$_n$, ($C_3$–$C_{12}$)-cycloalkyl-($C_1$–$C_8$)-alkyl-S(O)$_n$, ($C_6$–$C_{12}$)-bicycloalkyl-S(O)$_n$, ($C_6$–$C_{12}$)- bicycloalkyl-$(C_1-C_8)$-alkyl-S(O)$_n$, $(C_6-C_{12})$-tricycloalkyl-S(O)$_n$, $(C_6-C_{12})$-tricycloalkyl-$(C_1-C_8)$-alkyl-S(O)$_n$, optionally substituted $(C_6-C_{14})$-aryl-S(O)$_n$, $(C_6-C_{14})$-aryl-$(C_1-C_8)$-alkyl-S(O)$_n$ optionally substituted in the aryl radical, optionally substituted heteroaryl-S(O)$_n$ or heteroaryl-$(C_1-C_8)$-alkyl-S(O)$_n$ optionally substituted in the heteroaryl radical, where n is 1 or 2;

$R^1$ is hydrogen, $(C_1-C_{10})$-alkyl, which can optionally be monosubstituted or polysubstituted by fluorine, $(C_3-C_{12})$-cycloalkyl, $(C_3-C_{12})$-cycloalkyl-$(C_1-C_8)$-alkyl, optionally substituted $R^{21}$—$((C_6-C_{14})$-aryl), $(R^{21}$—$((C_6-C_{14})$-aryl))-$(C_1-C_8)$-alkyl optionally substituted in the aryl radical, the radical Het-, Het-$(C_1-C_8)$-alkyl or one of the radicals $R^{21}O$—, $R^{22}O$—NH—, $R^{21}O$—N($R^{23}$)—, $R^{24}$NH—, $R^{25}$N($R^{25}$)—, HO—$((C_1-C_8)$-alkyl)-N($R^{26}$)—, $R^{27}$C(O)—NH—, $R^{21}$C(O)—N($R^{23}$)—, $R^{21}$C(O)—, $R^{21}$O—C(O)—, $R^{28}$N($R^{21}$)—C(O)—, $R^{21}$O—N=, O= and S=;

$R^2$ is hydrogen, $(C_1-C_8)$-alkyl, optionally substituted $(C_6-C_{14})$-aryl, $(C_6-C_{14})$-aryl-$(C_1-C_8)$-alkyl optionally substituted in the aryl radical or $(C_3-C_8)$-cycloalkyl;

$R^3$ is hydrogen, $(C_1-C_8)$-alkyl, optionally substituted $(C_6-C_{14})$-aryl, $(C_6-C_{14})$-aryl-$(C_1-C_8)$-alkyl optionally substituted in the aryl radical, $(C_3-C_8)$-cycloalkyl, $(C_2-C_8)$-alkenyl, $(C_2-C_8)$-alkynyl, $(C_2-C_8)$-alkenylcarbonyl, $(C_2-C_8)$-alkynylcarbonyl, pyridyl, $R^{11}$NH, $R^4$CO, COOR$^4$, CON(CH$_3$)R$^4$, CONHR$^4$, CSNHR$^4$, COOR$^{15}$, CON(CH$_3$)R$^{15}$ or CONHR$^{15}$;

$R^4$ is hydrogen or $(C_1-C_{28})$-alkyl which can optionally be mono- or polysubstituted by identical or different radicals from the group consisting of hydroxyl, hydroxycarbonyl, aminocarbonyl, mono- or di-$((C_1-C_{18})$-alkyl)aminocarbonyl, amino-$(C_2-C_{18})$-alkylaminocarbonyl, amino-$(C_1-C_3)$-alkylphenyl-$(C_1-C_3)$-alkylaminocarbonyl, $(C_1-C_{18})$-alkylcarbonylamino-$(C_1-C_3)$-alkylphenyl-$(C_1-C_3)$-alkylaminocarbonyl, $(C_1-C_{18})$-alkylcarbonylamino-$(C_2-C_{18})$-alkylaminocarbonyl, $(C_6-C_{14})$-aryl-$(C_1-C_8)$-alkoxycarbonyl which can also be substituted in the aryl radical, amino, mercapto, $(C_1-C_{18})$-alkoxy, $(C_1-C_{18})$-alkoxycarbonyl, optionally substituted $(C_3-C_8)$-cycloalkyl, HOS(O)$_2$—$(C_1-C_3)$-alkyl, $R^9$NHS(O)$_2$—$(C_1-C_3)$-alkyl, $(R^8$O)$_2$P(O)—$(C_1-C_3)$-alkyl, tetrazolyl-$(C_1-C_3)$-alkyl, halogen, nitro, trifluoromethyl or the radical $R^5$;

$R^5$ is optionally substituted $(C_6-C_{14})$-aryl, $(C_6-C_{14})$-aryl-$(C_1-C_8)$-alkyl optionally substituted in the aryl radical, a mono- or bicyclic 5- to 12-membered heterocyclic ring which can be aromatic, partially hydrogenated or completely hydrogenated and which can contain 1, 2 or 3 identical or different heteroatoms from the group consisting of nitrogen, oxygen and sulfur, a radical $R^6$ or a radical $R^6$CO—, where the aryl radical and, independently thereof, the heterocyclic radical can be mono- or polysubstituted by identical or different radicals from the group consisting of $(C_1-C_{18})$-alkyl, $(C_1-C_{18})$-alkoxy, halogen, nitro, amino or trifluoromethyl;

$R^6$ is $R^7R^8$N, $R^7$O or $R^7$S or an amino acid side chain, a natural or unnatural amino acid, imino acid, optionally N—$(C_1-C_8)$-alkylated or N—$((C_6-C_{14})$-aryl-$(C_1-C_8)$-alkylated) azaamino acid or a dipeptide radical which can also be substituted in the aryl radical and/or in which the peptide bond can be reduced to —NH—CH$_2$—, and their esters and amides, where hydrogen or hydroxymethyl can optionally stand in place of free functional groups and/or where free functional groups can be protected by protective groups customary in peptide chemistry;

$R^7$ is hydrogen, $(C_1-C_{18})$-alkyl, $(C_6-C_{14})$-aryl-$(C_1-C_8)$-alkyl, $(C_1-C_{18})$-alkylcarbonyl, $(C_1-C_{18})$-alkoxycarbonyl, $(C_6-C_{14})$-arylcarbonyl, $(C_6-C_{14})$-aryl-$(C_1-C_8)$-alkylcarbonyl or $(C_6-C_{14})$-aryl-$(C_1-C_{18})$-alkyloxycarbonyl, where the alkyl groups can optionally be substituted by an amino group and/or where the aryl radicals can be mono- or polysubstituted, preferably monosubstituted, by identical or different radicals from the group consisting of $(C_1-C_8)$-alkyl, $(C_1-C_8)$-alkoxy, halogen, nitro, amino and trifluoromethyl, or is a natural or unnatural amino acid, imino acid, optionally N—$(C_1-C_8)$-alkylated or N—$((C_6-C_{14})$-aryl-$(C_1-C_8)$-alkylated) azaamino acid or a dipeptide radical which can also be substituted in the aryl radical and/or in which the peptide bond can be reduced to —NH—CH$_2$—;

$R^8$ is hydrogen, $(C_1-C_{18})$-alkyl, optionally substituted $(C_6-C_{14})$-aryl or $(C_6-C_{14})$-aryl-$(C_1-C_8)$-alkyl which can also be substituted in the aryl radical;

$R^9$ is hydrogen, aminocarbonyl, $(C_1-C_{18})$-alkylaminocarbonyl, $(C_3-C_8)$-cycloalkylaminocarbonyl, optionally substituted $(C_6-C_{14})$-arylaminocarbonyl, $(C_1-C_{18})$-alkyl, optionally substituted $(C_6-C_{14})$-aryl or $(C_3-C_8)$-cycloalkyl;

$R^{10}$ is hydroxyl, $(C_1-C_{18})$-alkoxy, $(C_6-C_{14})$-aryl-$(C_1-C_8)$-alkoxy which can also be substituted in the aryl radical, optionally substituted $(C_6-C_{14})$-aryloxy, amino or mono- or di-$((C_1-C_{18})$-alkyl)amino;

$R^{11}$ is hydrogen, $(C_1-C_{18})$-alkyl, $R^{12}$CO, $R^{12a}$CS, optionally substituted $(C_6-C_{14})$-aryl-S(O)$_2$, $(C_1-C_{18})$-alkyl-S(O)$_2$, $(C_6-C_{14})$-aryl-$(C_1-C_8)$-alkyl optionally substituted in the aryl radical, $R^9$NHS(O)$_2$ or the radical $R^{15}$;

$R^{12}$ is hydrogen, $(C_1-C_{18})$-alkyl, $(C_2-C_8)$-alkenyl, $(C_2-C_8)$-alkynyl, optionally substituted $(C_6-C_{14})$-aryl, $(C_1-C_{18})$-alkoxy, $(C_6-C_{14})$-aryl-$(C_1-C_8)$-alkoxy which can also be substituted in the aryl radical, optionally substituted $(C_6-C_{14})$-aryloxy, the radical $R^{15}$, the radical $R^{15}$—O—, amino, mono- or di-$((C_1-C_{18})$-alkyl)amino, $(C_2-C_8)$-alkenylamino, $(C_2-C_8)$-alkynylamino, $(C_3-C_{12})$-cycloalkylamino, $(C_3-C_{12})$-cycloalkyl-$(C_1-C_8)$-alkylamino, the radical $R^{15}$—NH—, optionally substituted $(C_6-C_{14})$-aryl-NH, $(C_6-C_{14})$-aryl-$(C_1-C_8)$-alkyl-NH, which can also be substituted in the aryl radical, optionally substituted heteroaryl-NH or heteroaryl-$(C_1-C_8)$-alkyl-NH optionally substituted in the heteroaryl radical;

$R^{12a}$ is amino, mono- or di-$((C_1-C_{18})$-alkyl)amino, $(C_2-C_8)$-alkenylamino, $(C_2-C_8)$-alkynylamino, $(C_3-C_{12})$-cycloalkylamino, $(C_3-C_{12})$-cycloalkyl-$(C_1-C_8)$-alkylamino, the radical $R^{15}$—NH—, optionally substituted $(C_6-C_{14})$-aryl-NH, $(C_6-C_{14})$-aryl-$(C_1-C_8)$-alkyl-NH, which can also be substituted in the aryl radical, optionally substituted heteroaryl-NH or heteroaryl-$(C_1-C_8)$-alkyl-NH optionally substituted in the heteroaryl radical;

$R^{13}$ is hydrogen, $(C_1-C_6)$-alkyl, $(C_6-C_{14})$-aryl-$(C_1-C_8)$-alkyl optionally substituted in the aryl radical or $(C_3-C_8)$-cycloalkyl;

$R^{15}$ is $R^{16}$—$(C_1-C_6)$-alkyl or $R^{16}$;

$R^{16}$ is a 6- to 24-membered bicyclic or tricyclic radical which is partially or completely unsaturated and which can also contain 1 to 4 identical or different heteroatoms from the group consisting of nitrogen, oxygen and sulfur and which can also be substituted by one or more identical or different substituents from the group consisting of $(C_1-C_4)$-alkyl and oxo;

$R^{21}$ is hydrogen, $(C_1-C_8)$-alkyl, $(C_3-C_{12})$-cycloalkyl, $(C_3-C_{12})$-cycloalkyl-$(C_1-C_8)$-alkyl, $(C_6-C_{14})$-aryl, $(C_6-C_{14})$-aryl-$(C_1-C_8)$-alkyl, the radical Het- or Het-$(C_1-C_8)$-alkyl, where alkyl radicals can be monosubstituted or polysubstituted by fluorine and the radicals $R^{21}$ can be identical or different if they occur several times;

$R^{22}$ is $(C_3-C_{12})$-cycloalkyl, $(C_3-C_{12})$-cycloalkyl-$(C_1-C_8)$-alkyl, $(C_6-C_{14})$-aryl, the radical Het- or Het-$(C_1-C_8)$-alkyl, where alkyl radicals can be monosubstituted or polysubstituted by fluorine;

$R^{23}$ is $(C_1-C_8)$-alkyl, $(C_3-C_{12})$-cycloalkyl, $(C_3-C_{12})$-cycloalkyl-$(C_1-C_8)$-alkyl, $(C_6-C_{14})$-aryl, $(C_6-C_{14})$-aryl-$(C_1-C_8)$-alkyl, the radical Het- or Het-$(C_1-C_8)$-alkyl, where alkyl radicals can be monosubstituted or polysubstituted by fluorine;

$R^{24}$ is $(C_3-C_{12})$-cycloalkyl, $(C_3-C_{12})$-cycloalkyl-$(C_1-C_8)$-alkyl, $(C_6-C_{14})$-aryl, $(C_6-C_{14})$-aryl-$(C_1-C_8)$-alkyl, the radical Het- or Het-$(C_1-C_8)$-alkyl, where alkyl radicals can be monosubstituted or polysubstituted by fluorine;

$R^{25}$ has the meanings of $R^{23}$, where the radicals $R^{25}$ can be identical or different;

$R^{26}$ has the meanings of $R^{21}$ or HO—$((C_1-C_8)$-alkyl), where alkyl radicals can be monosubstituted or polysubstituted by fluorine;

$R^{27}$ is hydrogen, $(C_3-C_{12})$-cycloalkyl, $(C_3-C_{12})$-cycloalkyl-$(C_1-C_8)$-alkyl, $(C_6-C_{14})$-aryl-$(C_1-C_8)$-alkyl, the radical Het- or Het-$(C_1-C_8)$-alkyl, where alkyl radicals can be monosubstituted or polysubstituted by fluorine;

$R^{28}$ is one of the radicals $R^{21}$—, $R^{21}O$—, $R^{26}N(R^{26})$—, $R^{21}C(O)$—, $R^{21}O$—C(O)—, $((C_1-C_{18})$-alkyl-O—C(O)—$((C_1-C_6)$-alkyl)-O—C(O)—, $R^{21}N(R^{21})$—C(O)—, $R^{21}N(R^{21})$—C(=N(R^{21}))— or $R^{21}C(O)$—N$(R^{21})$—;

Het is a mono- or polycyclic, 4- to 14-membered, aromatic or nonaromatic ring which contains 1, 2, 3 or 4 identical or different heteroatoms from the group consisting of N, O and S as ring members and can optionally be substituted by one or more, identical or different substituents;

b, c, d and f independently of one another are 0 or 1, but cannot all simultaneously be 0;

e, g and h independently of one another are 0, 1, 2, 3, 4, 5 or 6;

in all their stereoisomeric forms and mixtures thereof in any ratio, and their physiologically tolerable salts.

All above explanations for the formula I, for example with respect to alkyl radicals, aryl radicals, etc., also apply to the compounds of the formula Ie accordingly. The above preferred meanings also apply here correspondingly.

The above explanations for the preparation of the compounds of the formula I and their use likewise also apply to the compounds of the formula Ie. These compounds, of course, are also inhibitors of leucocyte adhesion and/or antagonists of the VLA-4 receptor and are suitable for the treatment and prophylaxis of diseases which are caused by an undesired extent of leucocyte adhesion and/or leucocyte migration or which are associated therewith or in which cell-cell or cell-matrix interactions which are based on interactions of VLA-4 receptors with their ligands play a part, for example of inflammatory processes. The present invention furthermore relates to the compounds of the formula Ie for use as pharmaceuticals and to pharmaceutical preparations which contain one or more compounds of the formula Ie and/or their physiologically tolerable salts in addition to pharmaceutically innocuous excipients and/or additives, the above explanations in turn also applying to these pharmaceutical preparations.

EXAMPLES

The products were identified by means of mass spectra (MS) and/or NMR spectra. Compounds which were purified by chromatography using an eluent which contained, for example, acetic acid or trifluoroacetic acid and were then freeze-dried partly still contained, depending on the freeze-drying procedure, the acid contained in the eluent, and were thus partially or completely obtained in the form of a salt of the acid used, for example in the form of the acetic acid salt or trifluoroacetic acid salt.

The abbreviations have the following meanings:

| | |
|---|---|
| DMF | N,N-Dimethylformamide |
| THF | Tetrahydrofuran |
| DCC | N,N'-Dicyclohexylcarbodiimide |
| HOBt | 1-Hydroxybenzotriazole |

EXAMPLE 1

((R,S)-4-(4-Aminocarbonylphenyl)-3-benzyl-4-methyl-2,5-dioxoimidazolidin-1-yl)acetyl-L-aspartyl-L-phenylglycine

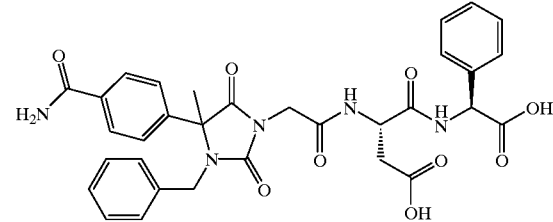

1a) (R,S)-4-(4-Cyanophenyl)-4-methyl-2,5-dioxoimidazolidine 20 g (138 mmol) of p-acetylbenzonitrile, 115.6 g of ammonium carbonate (1.21 mol) and 11.6 g of potassium cyanide (178 mmol) were dissolved in 600 ml of a mixture of 50% ethanol and 50% water. The mixture was stirred at 55° C. for 5 fours and allowed to stand at room temperature overnight. The solution was adjusted to a pH of 6.3 using 6N HCl and then stirred at room temperature for 2 hours. The precipitate was filtered off with suction, washed with water and dried over phosphorus pentoxide in a high vacuum. Yield: 22.33 g (75%). FAB-MS: 216.1 (M+H)$^+$ 1b) Methyl((R,S)-4-(4-cyanophenyl)-4-methyl-2,5-dioxoimidazolidin-1-yl)acetate 1.068 g of sodium (46.47 mmol) were dissolved in 110 ml of abs. methanol under nitrogen. The clear solution was treated with 10 g of (R,S)-4-(4-cyanophenyl)-4-methyl-2,5-dioxoimidazolidine (46.47 mmol) and the mixture was boiled under reflux for 2 h. 7.75 g (46.68 mmol) of potassium iodide were added and a solution of 4.53 ml of methyl chloroacetate (51.3 mmol) in 5 ml of methanol was added dropwise in the course of 1 hour.

The mixture was heated to boiling for 6 hours, allowed to stand at room temperature overnight and concentrated. The oily residue was chromatographed on silica gel using methylene chloride/ethyl acetate (9/1). Yield: 8.81 g (66%). FAB-MS: 288 (M+H)$^+$ 1c) Methyl ((R,S)-4-(4-cyanophenyl)-3-benzyl-4-methyl-2,5-dioxoimidazolidin-1-yl)acetate 5 g of methyl ((R,S)-4-(4-cyanophenyl)-4-methyl-2,5-dioxoimidazolidin-1-yl)acetate (17.4 mmol) were dissolved in 20 ml of anhydrous DMF under argon. 920 mg of a sodium hydride dispersion in mineral oil (19.14 mmol) were added in an argon countercurrent. The reaction mixture was stirred at room temperature for 15 minutes. A solution of 3.27 g of benzyl bromide (19.14 mmol) in 10 ml of anhydrous DMF was then added. The mixture was stirred at room temperature for 4 hours and then allowed to stand at room temperature overnight. The solution was concentrated. For purification, the substance was chromatographed on silica gel using methylene chloride/ethyl acetate (9.75/0.25). The fractions containing the pure substance were concentrated. Yield: 4.28 g (72%). FAB-MS: 378 (M+H)$^+$ 1d) ((R,S)-4-(4-Aminocarbonylphenyl)-3-benzyl-4-methyl-2,5-dioxoimidazolidin-1-yl)acetic acid 2.77 g of methyl ((R,S)-4-(4-cyanophenyl)-3-benzyl-4-methyl-2,5-dioxoimidazolidin-1-yl)acetate (7.34 mmol) were stirred at 40° C. for 5 hours in 50 ml of conc. HCl. The reaction mixture was diluted with water and extracted with methylene chloride. The organic phase was dried over sodium sulfate and, after filtration, concentrated in vacuo. The residue was chromatographed on silica gel using methylene chloride, then methylene chloride/ethyl acetate (9.9/0.2), then using methylene chloride/ethyl acetate (9/1). 460 mg of a mixture of ((R,S)-4-(4-aminocarbonylphenyl)-3-benzyl-4-methyl-2,5-dioxoimidazolidin-1yl)acetic acid and methyl ((R,S)-4-(4-aminocarbonylphenyl)-3-benzyl-4-methyl-2,5-dioxoimidazolidin-1-yl)acetate were obtained, which was treated with 120 ml of a triethylamine/water/dioxane mixture (1/1/1) and stirred at room temperature overnight. The solvent was removed in vacuo and the residue was freeze-dried several times with dilute acetic acid. Yield: 407 mg (16.8%. ESI-MS: 382.1 (M+H)$^+$ 1e) ((R,S)-4-)4-Aminocarbonylphenyl)-3-benzyl-4-methyl-2,5-dioxoimidazolidin-1yl)acetyl-L-aspartyl-L-phenylglycine di-tert-butyl ester 114 mg of DCC (0.52 mmol) were added at 0° C. to a solution of 200 mg of ((R,S)-4-(4-aminocarbonylphenyl)-3-benzyl-4-methyl-2,5-dioxoimidazoldin-1-yl)acetic acid (0.52 mmol), 215.8 mg of H-Asp(OBu$^t$)-Phg-OBu$^t$hydrochloride (0.52 mmol) and 71 mg of HOBt (0.52 mmol) in 5 ml of DMF. The mixture was stirred at 0° C. for one hour and at room temperature for 3 hours. The batch was then allowed to stand at room temperature overnight, the precipitate was filtered off with suction and the filtrate was concentrated. For purification, the substance was chromatographed on silica gel using methylene chloride/methanol/glacial acetic acid/water (9/1/0.1). Yield: 90 mg (23.3%). ESI-MS: 742.4 (M+H)$^+$ 1f) ((R,S)-4-(4-Aminocarbonylphenyl)-3-benzyl-4-methyl-2,5-dioxoimidazolidin-1-yl)acetyl-L-aspartyl-L-phenylglycine 90 mg of (R,S)-4-(4-aminocarbonylphenyl)-3-benzyl-4-methyl-2,5-dioxoimidazolidin-1-yl)acetyl-L-aspartyl-L-phenylglycine di-tert-butyl ester (0.12 mmol) were dissolved in a mixture of 2.25 ml of trifluoroacetic acid and 0.25 ml of water. The mixture was allowed to stand at room temperature for one hour and was concentrated in a water-jet vacuum. For purification, the substance was chromatographed on silica gel using methylene chloride/methanol/glacial acetic acid/water (7/3/0.3/0.3) and then using methylene chloride/methanol/glacial acetic acid/water (8.5/1.5/0.15/0.15). The residue obtained was freeze-dried. Yield: 17 mg of a colorless solid (22.5%). FAB-MS: 630.2 (M+H)$^+$

EXAMPLE 2

((R,S)-4-(4-(4,5-Dihydro-2-imidazolyl)phenyl)-3-(2-naphthylmethyl)-4-methyl-2,5-dioxoimidazolidin-1-yl)acetyl-L-aspartyl-L-phenylglycine

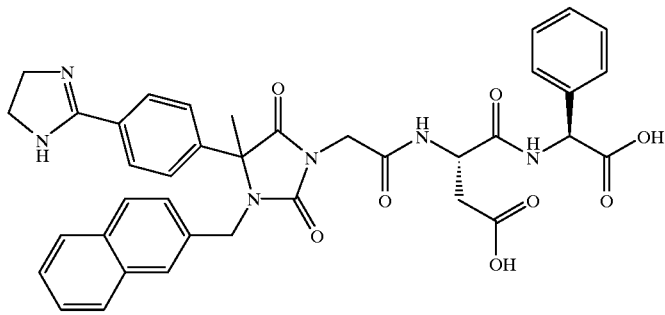

2a) ((R,S)-4-(4-(ethoxy-imino-methyl)phenyl)-3-(2-naphthylmethyl)-4-methyl-2,5-dioxoimidazolidin-1-yl)acetate hydrochloride A suspension of 4 g (9.37 mmol) of methyl ((R,S)-4-(4-cyano-phenyl)-3-(2-naphthylmethyl)-4-methyl-2,5-dioxoimidazolidin-1-yl)acetate (prepared by reaction of methyl ((R,S)-4-(4-cyanophenyl)-4-methyl-2,5-dioxo-imidazolidin-1yl)acetate with 2-bromomethylnaphthalene analogously to Example 1c) in 40 ml of absolute ethanol was cooled to 0° C. Dry HCl gas was passed into the suspension, the temperature always being kept below 10° C. until the nitrile band was no longer present in the IR spectrum. The ethanolic solution was treated with diethyl ether until it became turbid and allowed to stand at 4° C. overnight. The precipitate was filtered off with suction. 4.2 g (88%) of the title compound were obtained as a colorless solid.

2b) ((R,S)-4-(4-(4,5-Dihydro-2-imidazolyl)phenyl)-3-(2-naphthylmethyl)-4-methyl-2,5-dioxoimidazolidin-1-yl)

acetic acid hydrochloride 4.75 ml of ethylenediamine were added to a suspension of 2.2 g (4.3 mmol) of methyl ((R,S)-4-(4-(ethoxy-imino-methyl)phenyl)-3-(2-naphthylmethyl)-4-methyl-2,5-dioxoimidazolidin-1-yl) acetate hydrochloride in 20 ml of isopropanol and the mixture was stirred at room temperature overnight. The solvent was removed in vacuo and the residue was triturated with diethyl ether. The diethyl ether was decanted off, and the residue was dried in vacuo and then refluxed for 2 h with 6N hydrochloric acid. The precipitate was filtered off with suction and washed with water. 1.5 g (71%) of the title compound were obtained as a colorless solid.

2c) ((R,S)-4-(4-(4,5-Dihydro-2-imidazolyl)phenyl)-3-(2-naphthylmethyl)-4-methyl-2,5-dioxoimidazolidin-1-yl) acetyl-L-aspartyl-L-phenylglycine di-tert-butyl ester hydrochloride A solution of 493 mg (1 mmol) of ((R,S)-4-(4-(4,5-dihydro-2-imidazolyl)phenyl)-3-(2-naphthylmethyl)-4-methyl-2,5-dioxoimidazolidin-1-yl)acetate acid hydrochloride in 10 ml of absolute DMF was treated with 135 mg (1 mmol) of HOBt and then with 220 mg (1 mmol) of DCC at 0° C. After stirring at 0° C. for 60 minutes and at room temperature for 60 minutes, 414 mg (1 mmol) of H-Asp (O′Bu)-Phg-(O′Bu)×HCl and then 0.1 ml of N-ethylmorpholine were added and the mixture was allowed to stand at room temperature overnight. The solvent was removed in vacuo and the residue was partitioned between ethyl acetate and water. The phases were separated and the organic phase was washed in succession with saturated NaHCO₃ solution, KHSO₄/K₂SO₄ solution and water and dried over sodium sulfate. The sodium sulfate was filtered off, the filtrate was concentrated in vacuo and the residue was chromatographed on silica gel using dichloromethane/methanol/acetic acid/water (9/1/0.1/0.1). After concentrating the product fraction, 430 mg (50%) of the title compound were obtained.

2d) ((R,S)-4-(4-(4,5-Dihydro-2-imidazolyl)phenyl)-3-(2-naphthylmethyl)-4-methyl-2,5-dioxoimidazolidin-1-yl) acetyl-L-aspartyl-L-phenylglycine 430 mg (0.5 mmol) of ((R,S)-4-(4-(4,5-dihydro-2-imidazolyl)phenyl)-3-(2-naphthylmethyl)-4-methyl-2,5-dioxoimidazolidin-1-yl)acetyl-L-aspartyl-L-phenylglycine di-tert-butyl ester hydrochloride were treated with 5 ml of 90% strength trifluoroacetic acid. After 1 h at room temperature, the reaction mixture was concentrated and the residue was chromatographed on Sephadex LH20 using water/butanol/acetic acid (43/4.3/3.5). After freeze-drying of the production fraction, 92 mg (26%) of the title compound were obtained. ES(+)-MS: 705.2 (M+H)⁺

EXAMPLE 3

(S)-3-(((R,S)-4-(4-(4,5-Dihydro-2-imidazolyl) phenyl)-3-(2-naphthylmethyl)-4-methyl-2,5-dioxoimidazolidin-1-yl)acetylamino)-2-(1-adamantyl-methyloxycarbonylamino)propionic acid

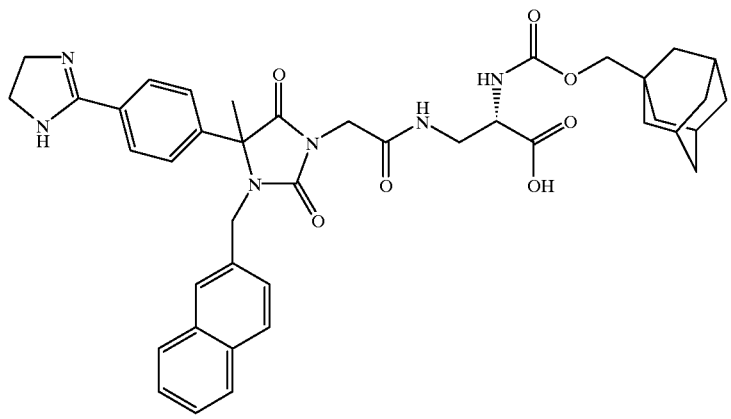

3a) tert-Butyl (S)-3-amino-2-benzyloxycarbonylaminopropionate 10 g (42 mmol) of (S)-3-amino-2-benzyloxycarbonylaminopropionic acid were shaken in an autoclave at an N₂ pressure of 20 atm for 3 days in a mixture of 100 ml of dioxane, 100 ml of isobutylene and 8 ml of conc. H₂SO₄. Excess isobutylene was blown out and 150 ml of diethyl ether and 150 ml of saturated NaHCO₃ solution were added to the remaining solution. The phases were separated and the aqueous phase was extracted 2× with 100 ml of diethyl ether each time. The combined organic phases were washed with 2×100 ml of water and dried over Na₂SO₄. After removing the solvent in vacuo, 9.58 g (78%) of the title compound were obtained as a pale yellow oil.

3b) tert-Butyl (S)-2-amino-3-tert-butoxycarbonylaminopropionate hydrochloride 8.9 g (40.8 mmol) of di-tert-butyl dicarbonate and then, in portions, 1N NaOH were added at 0° C. to a solution of 10 g (34 mmol) of tert-butyl (S)-3-amino-2-benzyloxycarbonylaminopropionate in 600 ml of THF/water (2/1) such that the pH of the solution was between 9 and 10 (consumption of 1N NaOH:32 ml). After stirring at room temperature for 3 h, 1 l of water was added and the mixture was extracted three times with diethyl ether. After drying over sodium sulfate, filtering and removing the solvent in vacuo, the residue was chromatographed on silica gel using dichloromethane/methanol (20/1). 13.19 g (98%) of tert-butyl (S)-2-benzyloxycarbonylamino-3-tert-butoxycarbonylaminopropionate were obtained. 13.1 g of the tert-butyl (S)-2-benzyloxycarbonylamino-3-tertbutoxycarbonylamino-propionate were hydrogenated over 10% Pd/C in methanol/HCl. After 1.5 h, the mixture was filtered and the filtrate was concentrated in vacuo. 9.77 g (99%) of the title compound were obtained as a colorless solid.

3c) tert-Butyl-(S)-2-(1-adamantylmethyloxycarbonylamino)-3-tert-butoxycarbonylaminopropionate A solution of 10.9 g (65.4 mmol) of (1-hydroxymethyl) adamantane and 10.6 g (65.4 mmol) of carbonyldiimidazole in 60 ml of THF were stirred at 50° C. for 1.5 h. 9.7 g (32.7 mmol) of tert-butyl (S)-2-amino-3-tert-butoxycarbonylaminopropionate hydrochloride in 25 ml of THF and 5.6 ml (32.7 mmol) of diisopropylethylamine were added, and the mixture was stirred at 60° C. for 4 h and allowed to stand at room temperature overnight. The solvent was removed in vacuo and the residue was chromatographed on silica gel using heptane/ethyl acetate (7/3). 8.7 g (59%) of the title compound were obtained as a colorless oil.

3d) tert-Butyl (S)-2-(1-adamantylmethyloxycarbonylamino)-3-aminopropionate

A solution of 8.7 g (19.22 mmol) of tert-butyl (S)-2-(1-adamantyl-methyloxycarbonylamino)-3-tert-butoxycarbonylamino-propionate in 180 ml of trifluoroacetic acid/dichloromethane (1/1) were added after 1 min to 1.5 l of ice-cold NaHCO$_3$ solution, the mixture was extracted three times with dichloromethane and the dichloromethane phase was then dried over sodium sulfate. After filtration and removal of the solvent in vacuo, 6.35 g (94%) of the title compound were obtained as a colorless solid.

3e) (S)-3-(((R,S)-4-(4-(4,5-Dihydro-2-imidazolyl)phenyl)-3-(2-naphthylmethyl)-4-methyl-2,5-dioxoimidazolidin-1-yl)acetylamino)-2-(1-adamantylmethyloxycarbonylamino) propionic acid The synthesis was carried out analogously to Example 2 using tert-butyl (S)-2-(1-adamantylmethyloxycarbonylamino)-3-aminopropionate instead of H-Asp(O$^t$Bu)-Phg-(O$^t$Bu)×HCl. After cleavage of the tert-butyl ester using 90% strength trifluoroacetic acid, the crude product was purified by chromatography on silica gel using dichloromethane/methanol/acetic acid/water (9/1/0.1/0.1). ES(+)-MS: 735.3 (M+H)$^+$ The compounds of Examples 5 to 17 were prepared by solid-phase synthesis according to the general procedure indicated in Example 4.

EXAMPLE 4

Solid-phase synthesis (general procedure)

General

The syntheses on the polymeric support were carried out according to the synthesis sequence which is shown in Scheme 1. The radicals R$^{50}$ to R$^{55}$ in Scheme 1 have the meaning of the radicals which are located in the position in the molecule concerned in formula I, or they can contain functional groups in protected form or in the form of precursors. R$^{50}$ corresponds to the radical R. R$^{51}$ corresponds to the radicals R$^4$ and R$^{15}$, where functional groups present in these radicals can be present in protected form or in the form of precursors (the radical —NHR$^{51}$ can thus represent, for example, the radical of an amino acid which is formally obtained by removing a hydrogen atom from the amino group). R$^{52}$, together with the CH group to which this radical is bonded, corresponds to the group B (R$^{52}$ thus corresponds to the group R$^1$-A, where functional groups present therein can be present in protected form or in the form of precursors R$^{55}$ corresponds to the group R$^0$.

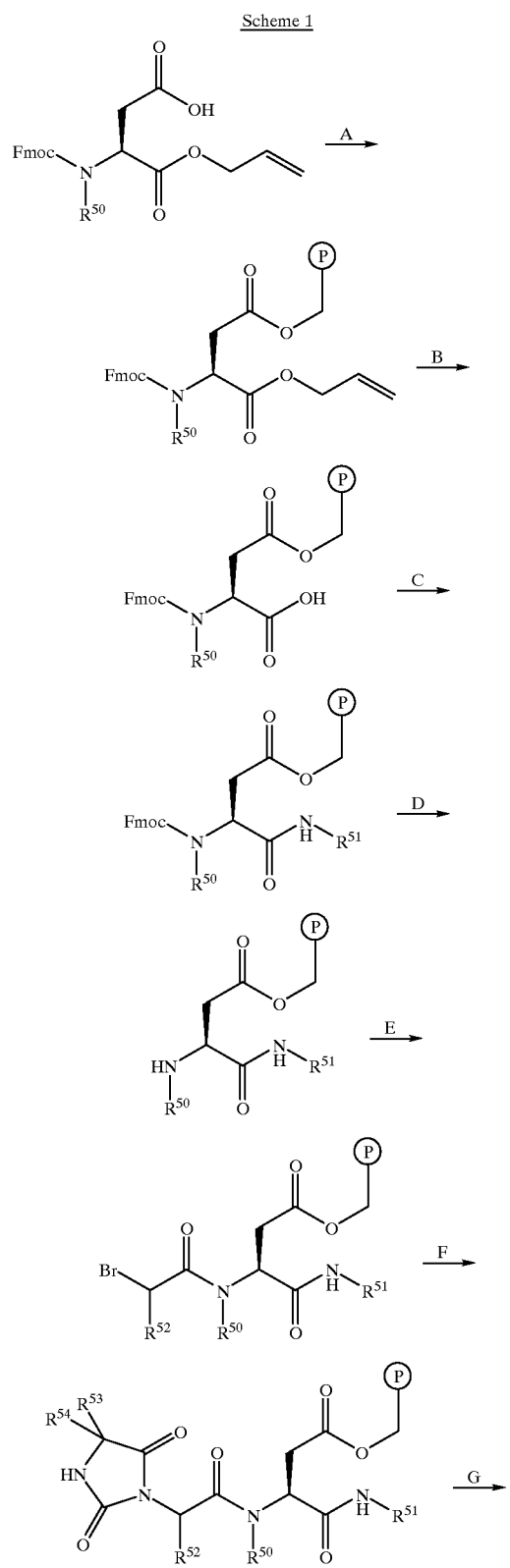

Scheme 1

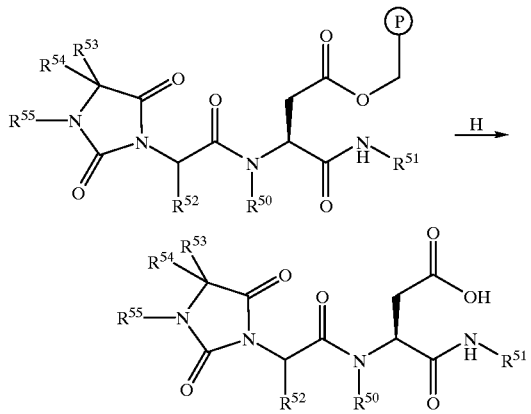

The synthesis of intermediates on a larger scale was carried out in special reaction vessels with frits inserted at the bottom of the reaction vessel; the synthesis of the compounds of the formula I was carried out in syringes or reaction blocks (Act 496, MultiSyn Tech). The syntheses on the resin were monitored by on bead analysis (FT-IR with ATR unit and MAS-NMR) and cleavage of an analytical sample from the resin (HPLC, MS, NMR).

Preparation of the aspartic acid building block FmocAsp (OH)O Allyl

FmocAsp(OtBU)O Allyl (40 g, 88.7 mmol) was treated with 25 ml of trifluoroacetic acid and the mixture was stirred at room temperature for 30 min. The solvent was stripped off on a rotary evaporator. The residue was dried in vacuo. FmocAsp(OH)O Allyl was obtained as a yellow oil (33.9 g, 97%). ES(+)-MS: 395.2 (M+H)$^+$ Linkage to the polymeric support (Step A in Scheme 1)

40 g of Wang polystyrene resin (1.1 mmol/g; Bachem) were preswollen at room temperature with 20 ml of DMF for 5 min. After addition of a solution of 26.0 g (1.5 equivalents) of FmocAsp(OH)O Allyl and 34.3 g (1.5 equivalents of 1-benzotriazolyloxytripyrrolidinophosphonium hexafluorophosphate in (PyBOP) and 9.3 ml (1.5 equivalents) of diisopropylethylamine in 120 ml of DMF, the mixture was shaken at 40° C. for 10 h. After reaction was complete, the solution was filtered off with suction and the resin was washed with DMF (5×20 ml). After addition of a solution of acetic anhydride (10 ml) and diisopropylethylamine (9.3 ml, 1.5 equivalents) in 40 ml of DMF, the mixture was again shaken at room temperature for 30 min. The solution was filtered off with suction and the resin was washed in succession three times each with 40 ml of DMF, of methanol and of dichloromethane. The resin was then dried in vacuo. Determination of the loading by the Fmoc method showed a loading of 0.6 mmol/g.

Cleavage of the allyl group on the polymeric support (Step B)

The resin was preswollen under argon for 5 min in DMF at room temperature. After addition of tetrakis (triphenylphosphine)palladium and N-methylpyrrolidine (10 equivalents), the mixture was shaken at 40° C. for 6 h under argon. After reaction was complete, the solution was filtered off with suction and the resin was washed in succession three times each with DMF, methanol, toluene and dichloromethane and then dried.

Coupling with amino compounds on the polymeric support (Step C)

The loaded resin with a free carboxyl function was preswollen at room temperature for 5 min in DMF. After addition of a solution of HOBt (1.2 equivalents), TOTU (1.2 equivalents) and diisopropylethylamine (1.2 equivalents) in DMF, the mixture was shaken at room temperature for 30 min. The amino compound (1.2 equivalents) was added dissolved in DMF. The suspension was shaken at room temperature until reaction was complete (HPLC checking). After reaction was complete, the solution was filtered off with suction and the resin was washed in succession three times each with DMF, methanol, toluene and dichloromethane and then dried.

Cleavage of the Fmoc protective group (Step D)

For cleavage of the Fmoc protective group, the resin was preswollen at room temperature for 5 min in DMF. After addition of a solution of DMF/piperidine (1/1), the mixture was shaken at room temperature for 20 min. The solution was filtered off with suction and the process was repeated. The cleavage of an analytical sample showed complete reaction according to HPLC/MS investigation. After complete reaction, the resin was washed three times with dichloromethane and employed directly in the coupling.

Coupling with α-halocarboxylic acids (Step E)

The resin was preswollen for 5 min with dichloromethane at room temperature. The α-halocarboxylic acid halides (1.5 equivalents) were added dissolved in dichloromethane. After addition of a catalytic amount of 4-dimethylaminopyridine and diisopropylethylamine (1 equivalent), the mixture was shaken at room temperature for 8 h. After reaction was complete, the solution was filtered off with suction and the resin was washed in succession three times each with DMF, toluene and dichloromethane and then immediately further reacted.

Instead of using the acid halides, the coupling can also be carried out using the acids and diisopropylcarbodiimide (DIC). For this, the symmetrical anhydrides are formed from α-halocarboxylic acids (5 equivalents) by 30-minute reaction with diisopropylcarbodiimide (2.4 equivalents) in dichloromethane. After this time, 2 equivalents of diisopropylethylamine are added. The mixture is added to the resin and shaken at room temperature for 12 h. After reaction is complete, the solution is filtered off with suction and the resin is washed in succession three times each with DMF, toluene and dichloromethane and then immediately further reacted.

Coupling of the α-haloacyl compounds with hydantoins (Step F)

The 4,4-disubstituted hydantoins (2 equivalents) were activated in DMF with diazabicyclcloundecene (DBU) (2 equivalents) at room temperature. The activated solution was added after 15 min to the resin preswollen in DMF for 5 min. The mixture was shaken at room temperature for 8 h. After reaction was complete, the solution was filtered off with suction and the resin was washed in succession three times each with DMF, methanol, toluene and dichloromethane and then dried.

N-Alkylation of the hydantoin on the polymeric support (Step G)

The resin was preswollen for 5 min in DMF at room temperature. After addition of N'''-tert-butyl-N,N,N',N',N'',N''-hexamethylphosphorimidic triamide (phosphazene base Pl-t-Bu) (3 equivalents), the mixture was shaken at room temperature for 30 min. After addition of the alkylating agent (bromide or iodide), the mixture was shaken at room temperature for 4 h. After reaction was complete, the solution was filtered off with suction and the resin was washed in succession three times each with DMF, toluene and dichloromethane and then dried.

Instead of using phosphazenes, the alkylation can also be carried out using cesium carbonate. For this, the resin is preswollen for 5 min in DMF at room temperature. After addition of cesium carbonate (3 equivalents), the mixture is shaken at room temperature for 30 min. After addition of the alkylating agent (bromide or iodide), the mixture is shaken at 50° C. for 6 h.

After reaction is complete, the solution is filtered off with suction and the resin is washed in succession three times each with DMF, methanol/water/DMF (1.5/1.5/7), DMF, toluene and dichloromethane and then dried.

Cleavage from the resin (Step H)

For cleavage of the compound from the resin, a mixture of trifluoroacetic acid/dichloromethane (1/1) was added to the resin. The suspension was shaken for 1 h. The resin was filtered off. The remaining solution was concentrated in vacuo. The residue was purified by silica gel chromatography (dichloromethane and ethyl acetate).

The compounds of Examples 5 and 17 which have the structure indicated in formula If were prepared according to the general method described in Example 4. The meanings of the radicals in the individual compounds are indicated in Table 1.

In Table 1 denote:

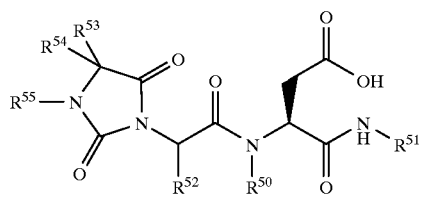

Bn = Benzyl  
3-Py = 3-Pyridylmethyl  
H = Hydrogen  
Et = Ethyl  
iBu = Isobutyl  
2-Py = 2-Pyridylmethyl  
4-Py = 4-Pyridylmethyl  
Me = Methyl  
nBu = n-Butyl Phg is the L-phenylglycyl radical, i.e. the radical of the amino acid L-phenylglycine, which stands for the radical —NH—$R^{51}$ in formula If and which is formally obtained by abstraction of a hydrogen atom from the amino group of phenylglycine.

TABLE 1

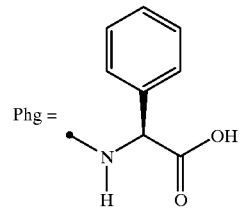

| Example | $R^{50}$ | —NH—$R^{51}$ | $R^{52}$ | $R^{53}$ | $R^{54}$ | $R^{55}$ | ES-(+)-MS |
|---|---|---|---|---|---|---|---|
| 5 | H | Phg | H | Me | Me | Bn | 525.5 |
| 6 | H | Phg | nBu | Me | Me | Bn | 581.6 |
| 7 | H | Phg | nBu | Me | Me | 2-Py | 582.6 |
| 8 | H | Phg | nBu | Me | Me | 3-Py | 582.6 |
| 9 | H | Phg | nBu | Me | Me | 4-Py | 582.6 |
| 10 | H | Phg | iBu | Me | Me | Bn | 581.6 |
| 11 | H | Phg | iBu | Me | Me | 2-Py | 582.6 |
| 12 | H | Phg | iBu | Me | Me | 3-Py | 582.6 |
| 13 | H | Phg | iBu | Me | Me | 4-Py | 582.6 |

TABLE 1-continued

| Example | $R^{50}$ | —NH—$R^{51}$ | $R^{52}$ | $R^{53}$ | $R^{54}$ | $R^{55}$ | ES-(+)-MS |
|---|---|---|---|---|---|---|---|
| 14 | H | Phg | H | Me | Me | 2-Py | 526.5 |
| 15 | H | Phg | H | Me | Me | 3-Py | 526.5 |
| 16 | H | Phg | H | Me | Me | 4-Py | 526.5 |
| 17 | H | Phg | Et | Me | Me | Bn | 553.6 |

Investigation of the biological activity

As a test method for the activity of the compounds of the formula I on the interaction between VCAM-1 and VLA-4, an assay is used which is specific for this interaction. The cellular binding components, i.e. the VLA-4-integrins, are offered in their natural form as surface molecules on human U937 cells (ATCC CRL 1593), which belong to the group of leucocytes. As specific binding components, recombinant soluble fusion proteins, prepared by genetic engineering and consisting of the extracytoplasmic domains of human VCAM-1 and the constant region of a human immunoglobulin of the subclass IgG1, are used.

Test method

Assay for the measurement of the adhesion of U937 cells (ATCC CRL 1593) to hVCAM-1(1-3)-IgG 1. Preparation of human VCAM-(1(1-3)-IgG and human CD4-IgG A genetic construct for the expression of the extracellular domains of human VCAM-1 was employed, associated with the genetic sequence of the heavy chain of human immunoglobulin IgG1 (hinge, CH2 and CH3 regions), from Dr. Brian Seed, Massachusetts General Hospital, Boston, USA. The soluble fusion protein hVCAM-1(1-3)-IgG contained the three amino-terminal extracellular immunoglobulin-like domains of human VCAM-1 (Damle and Aruffo, Proc. Natl. Acad. Sci. USA 1991, 88, 6403). CD4-IgG (Zettlmeissl et al., DNA and Cell Biology 1990, 9, 347) served as a fusion protein for negative controls. The recombinant proteins were expressed as soluble proteins after DEAE/dextran-mediated DNA-transfection in COS cells (ATCC CRL 1651) according to standard procedures (Ausubel et al., Current protocols in molecular biology, John Wiley & Sons, Inc. 1994).

2. Assay for the measurement of the adhesion of U937 cells to hVCAM-1(1-3)-IgG 2.1 96-well microtiter test plates (Nunc Maxisorb) were incubated at room temperature for 1 hour with 100 µl/well of a goat-anti-human IgG antibody solution (10 µg/ml in 50 mM Tris, pH 9.5). After removing the antibody solution, washing was carried out once with PBS.

2.2 150 µl/well of a blocking buffer (1% BSA in PBS) was incubated on the plates at room temperature for 0.5 hour. After removing the blocking buffer, washing was carried out once with PBS.

2.3 100 µl per well of a cell culture supernatant of transfected COS cells were incubated on the plates at room temperature for 1.5 hours. The COS cells were transfected with a plasmid which cods for the three N-terminal immunoglobulin-like domains of VCAM-1, coupled to the Fc part of human $IgG_1$ (hVCAM-1(1-3)-IgG). The content of hVCAM-1(1-3)-IgG was about 0.5–1 μg/ml. After removing the culture supernatant, washing was carried out once with PBS.

2.4 The plates were incubated at room temperature for 20 minutes with 100 μl/well of Fc receptor blocking buffer (1 mg/ml of γ-globulin, 100 mM NaCl, 100 μM MgCl$_2$, 100 μM MnCl$_2$, 100 μM CaCl$_2$, 1 mg/ml BSA in 50 mM HEPES, pH 7.5). After removing the Fc receptor blocking buffer, washing was carried out once with PBS.

2.5 20 μl of binding buffer (100 mM NaCl, 100 μM MgCl$_2$, 100 μM MnCl$_2$, 100 μM CaCl$_2$, 1 mg/ml BSA in 50 mM HEPES, pH 7.5), were initially introduced, the substances to be tested were added in 10 μl of binding buffer and the mixture was incubated for 20 minutes. As controls, antibodies against VCAM-1 (BBT, No. BBA6) and against VLA-4 (Immunotech, No. 0764) were used.

2.6 U937 cells were incubated in Fc receptor blocking buffer for 20 minutes and then pipetted in at a concentration of 1×10$^6$/ml and in an amount of 100 μl per well (final volume 125 μl/well).

2.7 The plates were slowly immersed at an angle of 45° in stop buffer (100 mM NaCl, 100 μM MgCl$_2$, 100 μM MnCl$_2$, 100 μM CaCl$_2$ in 25 mM Tris, pH 7.5) and shaken off. The process was repeated.

2.8 50 μl/well of a dye solution (16.7 μg/ml of Hoechst dye 33258, 4% formaldehyde, 0.5% Triton X-100 in PBS) were then incubated on the plates for 15 minutes.

2.9 The plates were shaken off and slowly immersed at an angle of 45° in stop buffer (100 mM NaCl, 100 μM MgCl$_2$, 100 μM MnCl$_2$, 100 μM CaCl$_2$ in 25 mM tris, pH7.5). The process was repeated. Then, with the liquid, measurements were made in a cytofluorimeter (Millipore) (sensitivity: 5; filter: excitation wavelength: 360 nm, emission wavelength: 460 nm).

The intensity of the light emitted by the stained U937 cells is a measure of the number of the U937 cells adhered to the hVCAM-1(1-3)-IgG and remaining on the plate and thus a measure of the ability of the added test substance to inhibit this adhesion. From the inhibition of the adhesion at various concentrations of the test substance, the concentration IC$_{50}$ which leads to an inhibition of the adhesion by 50% was calculated.

The following test results were obtained:

| Example | U937/VCAM-1 cell adhesion test IC$_{50}$ (μM) |
|---|---|
| 1 | 7.5 |
| 2 | 14.5 |
| 3 | 40 |

It will be apparent to those skilled in the art that various modifications and variations can be made to the compositions and processes of this invention. Thus, it is intended that the present invention cover such modifications and variations, provided they come within the scope of the appended claims and their equivalents.

The disclosure of all publications cited above expressly incorporated herein by reference in their entireties to the same extent as if each were incorporated by reference individually. The disclosure of German Patent Application No. 19647382.9, for which benefit under 35 USC § 119 is claimed, is expressly incorporated herein in its entirety.

What is claimed is:

1. A method for the suppression of inflammation comprising administering to a subject in need thereof a preparation comprising a VLA-4-antagonizing-effective amount of one or more compounds of the formula I

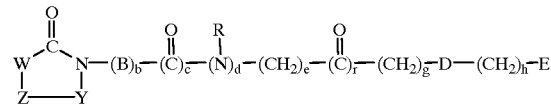

in which

W is $R^1$—A—C($R^{13}$) or $R^1$—A—CH=C;

Y is a carbonyl;

Z is N($R^0$);

A is a bivalent radical from the group consisting of (C$_1$–C$_6$) alkylene, (C$_3$–C$_{12}$)-cycloalkylene, (C$_1$–C$_6$)-alkylene-(C$_3$–C$_{12}$)-cycloalkyl, phenylene, phenylene-(C$_1$–C$_6$)-alkyl, (C$_1$–C$_6$)-alkylenephenyl, (C$_1$–C$_6$)-alkylenephenyl-(C$_1$–C$_6$)-alkyl, phenylene-(C$_2$–C$_6$)-alkenyl or a bivalent radical of a 5 or 6-membered saturated or unsaturated ring which can contain 1 or 2 nitrogen atoms and can be mono- or disubstituted by (C$_1$–C$_6$)-alkyl or doubly bonded oxygen or sulfur;

H is a bivalent radical from the group consisting of (C$_1$–C$_6$)-alkylene, (C$_2$–C$_6$)-alkenylene, phenylene, phenylene (C$_1$ C$_3$)-alkyl, (C$_1$–C$_3$)-alkylenephenyl, where the bivalent (C$_1$–C$_6$)-alkylene radical can be unsubstituted or substituted by a radical from the group consisting of (C$_1$–C$_8$)-alkyl, (C$_2$–C$_8$)-alkenyl, (C$_2$–C$_8$)-alkynyl, (C$_3$ C$_{10}$) cycloalkyl, (C$_3$–C$_{10}$)-cycloalkyl-(C$_1$–C$_6$)-alkyl, optionally substituted (C$_6$–C$_{14}$)-aryl, (C$_6$–C$_{14}$)-aryl-(C$_1$–C$_6$)-alkyl optionally substituted in the aryl radical, optionally substituted heteroaryl and heteroaryl (C$_1$ C$_6$) alkyl optionally substituted in the heteroaryl radical;

D is C($R^2$)($R^3$), N($R^3$) or CH=C($R^3$);

E is tetrazolyl, ($R^8$O)$_2$P(O), HOS(O)$_2$, $R^9$NHS(O)$_2$ or $R^{10}$CO;

R is hydrogen, (C$_1$–C$_8$)-alkyl, (C$_3$–C$_{12}$)-cycloalkyl, (C$_3$–C$_{12}$)-cycloalkyl-(C$_1$–C$_8$)-alkyl, optionally substituted (C$_6$–C$_{14}$)-aryl, (C$_6$–C$_{14}$)-aryl-(C$_1$–C$_8$)-alkyl optionally substituted in the aryl radical, optionally substituted heteroaryl or heteroaryl-(C$_1$–C$_8$)-alkyl optionally substituted in the heteroaryl radical, where alkyl radicals can be mono- or polysubstituted by fluorine;

$R^0$ is hydrogen, (C$_1$–C$_8$)-alkyl, (C$_3$–C$_{12}$)-cycloalkyl, (C$_3$–C$_{12}$)-cycloalkyl-(C$_1$–C$_8$)-alkyl, (C$_6$–C$_{12}$)-bicycloalkyl, (C$_6$–C$_{12}$)-bicycloalkyl-(C$_1$–C$_8$)-alkyl, (C$_6$–C$_{12}$)-tricycloalkyl, (C$_6$–C$_{12}$)-tricycloalkyl-(C$_1$–C$_8$)-alkyl, optionally substituted (C$_6$–C$_{14}$)-aryl, (C$_6$–C$_{14}$)-aryl-(C$_1$–C$_8$)-alkyl optionally substituted in the aryl radical, optionally substituted heteroaryl, heteroaryl-(C$_1$–C$_8$)-alkyl optionally substituted in the heteroaryl radical, CHO, (C$_1$–C$_8$)-alkyl-CO, (C$_3$–C$_{12}$)-cycloalkyl-CO, (C$_3$–C$_{12}$)-cycloalkyl-(C$_1$–C$_8$)-alkyl-CO, (C$_6$–C$_{12}$)-bicycloalkyl-CO, (C$_6$–C$_{12}$)-bicycloalkyl-(C$_1$–C$_8$)-alkyl-CO, (C$_6$–C$_{12}$)-tricycloalkyl-CO, (C$_6$ C$_{12}$)-tricycloalkyl-(C$_1$–C$_8$)-alkyl-CO, optionally substituted (C$_6$–C$_{14}$)-aryl-CO, (C$_6$–C$_{14}$)-aryl-(C$_1$–C$_8$)-alkyl-CO optionally substituted in the aryl radical, optionally substituted heteroaryl-CO, heteroaryl-(C$_1$–C$_8$)-alkyl-CO optionally substituted in the heteroaryl radical, (C$_1$–C$_8$)-alkyl-S(O)$_n$, (C$_3$–C$_{12}$) cycloalkyl-S(O)$_n$, (C$_3$–C$_{12}$)-cycloalkyl-(C$_1$–C$_8$)-alkyl-S(O)$_n$, (C$_6$–C$_{12}$)- bicycloalkyl $S(O)_n$, $(C_6-C_{12})$-bicycloalkyl-$(C_1-C_8)$-alkyl-$S(O)_n$, $(C_6-C_{12})$-tricycloalkyl $S(O)_n$, $(C_6-C_{12})$-tricycloalkyl-$(C_1-C_8)$-alkyl-$S(O)_n$, optionally substituted $(C_6\ C_{14})$-aryl-$S(O)_n$, $(C_6-C_{14})$-aryl-$(C_1-C_8)$-alkyl-$S(O)_n$ optionally substituted in the aryl radical, optionally substituted heteroaryl-$S(O)_n$ or heteroaryl-$(C_1\ C_8)$ alkyl-$S(O)_n$ optionally substituted in the heteroaryl radical, where n is 1 or 2;

$R^1$ is hydrogen, $(C_1-C_{10})$-alkyl, which can optionally be mono substituted or polysubstituted by fluorine, $(C_3-C_{12})$-cycloalkyl, $(C_3-C_{12})$-cycloalkyl-$(C_1-C_8)$-alkyl, optionally substituted $R^{21}$—$((C_6-C_{14})$-aryl), $(R^{21}$—$((C_6-C_{14})$ aryl))-$(C_1-C_8)$-alkyl optionally substituted in the aryl radical, the radical Het, Het-$(C_1-C_8)$-alkyl or one of the radicals $R^{21}O$—, $R^{22}O$—NH—, $R^{21}O$—N($R^{23}$)—, $R^{24}$NH, $R^{25}$N($R^{25}$)—, HO—$((C_1-C_8)$-alkyl)-N($R^{26}$)—, $R^{27}C(O)$—NH—, $R^{21}C(O)$—N($R^{23}$)—, $R^{21}C(O)$—, $R^{21}O$—C(O)—, $R^{38}$N($R^{31}$)—C(O)—, $R^{21}O$—N=, O= and S=;

$R^2$ is hydrogen, $(C_1-C_8)$-alkyl, optionally substituted $(C_6-C_{14})$-aryl, $(C_6-C_{14})$-aryl-$(C_1-C_8)$-alkyl optionally substituted in the aryl radical or $(C_3-C_8)$-cycloalkyl;

$R^3$ is hydrogen, $(C_1-C_8)$-alkyl, optionally substituted $(C_6-C_{14})$-aryl, $(C_6-C_{14})$-aryl-$(C_1-C_8)$-alkyl optionally substituted in the aryl radical, $(C_3-C_8)$-cycloalkyl, $(C_2-C_8)$-alkenyl, $(C_2-C_8)$-alkynyl, $(C_2-C_8)$-alkenylcarbonyl, $(C_2-C_8)$-alkynylcarbonyl, pyridyl, $R^{11}$NH, $R^4$CO, COOR$^4$, CON(CH$_3$)R$^4$, CONHR$^4$, CSNHR$^4$, COOR$^{15}$, CON(CH$_3$)R$^{15}$ or CONHR$^{15}$;

$R^4$ is hydrogen or $(C_1-C_{28})$-alkyl which can optionally be mono- or polysubstituted by identical or different radicals from the group consisting of hydroxyl, hydroxycarbonyl, aminocarbonyl, mono- or di-$((C_1-C_{18})$-alkyl)-aminocarbonyl, amino-$(C_2-C_{18})$-alkylaminocarbonyl, amino-$(C_1-C_3)$-alkylphenyl-$(C_1-C_3)$-alkylaminocarbonyl, $(C_1-C_{18})$-alkylcarbonylamino-$(C_1-C_3)$-alkylphenyl-$(C_1-C_3)$-alkylaminocarbonyl, $(C_1-C_{18})$-alkylcarbonylamino-$(C_2\ C_{18})$-alkylaminocarbonyl, $(C_6-C_{14})$-aryl-$(C_1-C_8)$-alkoxycarbonyl which can also be substituted in the aryl radical, amino, mercapto, $(C_1-C_{18})$-alkoxy, $(C_1-C_{18})$ alkoxycarbonyl, optionally substituted $(C_3-C_8)$-cycloalkyl, HOS(O)$_2$-$(C_1-C_3)$-alkyl, $R^9$NHS(O)$_2$-$(C_1-C_3)$-alkyl, $(R^8O)_2P(O)$-$(C_1-C_3)$-alkyl, tetrazolyl-$(C_1\ C_3)$ alkyl, halogen, nitro, trifluoromethyl or the radical $R^5$;

$R^5$ is optionally substituted $(C_6\ C_{14})$ aryl, $(C_6\ C_{14})$-aryl-$(C_1-C_8)$-alkyl optionally substituted in the aryl radical, a mono or bicyclic 5 to 12-membered heterocyclic ring which can be aromatic, partially hydrogenated or completely hydrogenated and which can contain one, two or three identical or different heteroatoms from the group consisting of nitrogen, oxygen and sulfur, a radical $R^6$ or a radical $R^6$CO—, where the aryl radical and, independently thereof, the heterocyclic radical can be mono- or polysubstituted by identical or different radicals from the group consisting of $(C_1-C_{18})$-alkyl, $(C_1-C_{18})$-alkoxy, halogen, nitro, amino and trifluoromethyl;

$R^6$ is $R^7R^8$N, $R^7$O or $R^7$S or an amino acid side chain, a natural or unnatural amino acid, imino acid, optionally N-$(C_1-C_8)$-alkylated or N-$((C_6-C_{14})$-aryl-$(C_1-C_8)$-alkylated) azaamino acid or a dipeptide radical which can also be substituted in the aryl radical and/or reduced in the peptide bond to —NH—CH$_2$—, and then esters and amides, where hydrogen or hydroxymethyl can optionally stand in place of free functional groups and/or where free functional groups can be protected by protective groups customary in peptide chemistry;

$R^7$ is hydrogen, $(C_1-C_{18})$-alkyl, $(C_6-C_{14})$-aryl-$(C_1-C_8)$-alkyl, $(C_1-C_{18})$-alkylcarbonyl; $(C_1-C_{18})$-alkoxycarbonyl, $(C_6-C_{14})$-arylcarbonyl, $(C_6-C_{14})$-aryl-$(C_1-C_8)$-alkylcarbonyl or $(C_6-C_{14})$-aryl-$(C_1-C_{18})$-alkyloxycarbonyl, where the alkyl groups can optionally be substituted by an amino group and/or where the aryl radicals can be mono- or polysubstituted by identical or different radicals from the group consisting of $(C_1-C_8)$-alkyl, $(C_1-C_8)$-alkoxy, halogen, nitro, amino and trifluoromethyl, or is a natural or unnatural amino acid, imino acid, optionally N-$(C_1-C_8)$-alkylated or N-$((C_6-C_{14})$-aryl $(C_1\ C_8)$-alkylated) azaamino acid or a dipeptide radical which can also be substituted in the aryl radical and/or reduced in the peptide bond to NH—CH$_2$—;

$R^8$ is hydrogen, $(C_1-C_{18})$-alkyl, optionally substituted $(C_6\ C_{14})$ aryl or $(C_6-C_{14})$-aryl-$(C_1-C_8)$-alkyl which can also be substituted in the aryl radical;

$R^9$ is hydrogen, aminocarbonyl, $(C_1-C_{18})$-alkylaminocarbonyl, $(C_3-C_8)$-cycloalkylaminocarbonyl, optionally substituted $(C_6-C_{14})$-arylaminocarbonyl, $(C_1-C_{18})$-alkyl, optionally substituted $(C_6-C_{14})$-aryl or $(C_3-C_8)$-cycloalkyl;

$R^{10}$ is hydroxyl, $(C_1-C_{18})$-alkoxy, $(C_6\ C_{14})$ aryl-$(C_1-C_8)$-alkoxy which can also be substituted in the aryl radical, optionally substituted $(C_6-C_{14})$-aryloxy, amino or mono- or di-$((C_1-C_{18})$ alkyl)amino;

$R^{11}$ is hydrogen, $(C_1-C_{18})$ alkyl, $R^{12}$CO, $R^{12a}$CS, optionally substituted $(C_6-C_{14})$-aryl-$S(O)_2$, $(C_1-C_{18})$ alkyl-$S(O)_2$, $(C_6-C_{14})$-aryl-$(C_1-C_8)$-alkyl optionally substituted in the aryl radical, $R^9$NHS(O)$_2$ or the radical $R^{15}$;

$R^{12}$ is hydrogen, $(C_1-C_{18})$ alkyl, $(C_2-C_8)$-alkenyl, $(C_2-C_8)$-alkynyl, optionally substituted $(C_6\ C_{14})$ aryl, $(C_1-C_{18})$-alkoxy, $(C_6-C_{14})$-aryl-$(C_1-C_8)$-alkoxy which can also be substituted in the aryl radical, optionally substituted $(C_6-C_{14})$-aryloxy, the radical $R^{15}$, the radical $R^{15}$—O—, amino, mono- or di-$((C_1-C_{18})$-alkyl)amino, $(C_2-C_8)$-alkenylamino, $(C_2-C_8)$-alkynylamino, $(C_3-C_{12})$-cycloalkylamino, $(C_3-C_{12})$-cycloalkyl-$(C_1-C_8)$-alkylamino, the radical $R^{15}$—NH—, optionally substituted $(C_6-C_{14})$-aryl-NH, $(C_6-C_{14})$-aryl-$(C_1-C_8)$-alkyl-NH, which can also be substituted in the aryl radical, optionally substituted heteroaryl-NH or heteroaryl-$(C_1-C_8)$-alkyl-NH optionally substituted in the heteroaryl radical;

$R^{12a}$ is amino, mono- or di-$((C_1-C_{18})$-alkyl)-amino, $(C_2-C_8)$-alkenylamino, $(C_2-C_8)$-alkynylamino, $(C_3-C_{12})$-cycloalkylamino, $(C_3-C_{12})$-cycloalkyl-$(C_1-C_8)$-alkylamino, the radical $R^{15}$—NH—, optionally substituted $(C_6-C_{14})$-aryl-NH, $(C_6-C_{14})$-aryl-$(C_1-C_8)$-alkyl-NH, which can also be substituted in the aryl radical, optionally substituted heteroaryl-NH or heteroaryl-$(C_1-C_8)$-alkyl-NH optionally substituted in the heteroaryl radical;

$R^{13}$ is hydrogen, $(C_1-C_6)$-alkyl, $(C_6-C_{14})$-aryl-$(C_1-C_8)$-alkyl optionally substituted in the aryl radical or $(C_3-C_8)$-cycloalkyl;

$R^{15}$ is $R^{16}$-$(C_1-C_6)$-alkyl or $R^{16}$;

$R^{16}$ is a 6- to 24-membered bicyclic or tricyclic radical which is saturated or partially unsaturated and which can also contain one to four identical or different heteroatoms from the group consisting of nitrogen, oxygen and sulfur and which can also be substituted by one or more identical or different substituents from the group consisting of $(C_1–C_4)$-alkyl and oxo;

$R^{21}$ is hydrogen, $(C_1–C_8)$-alkyl, $(C_3–C_{12})$-cycloalkyl, $(C_3–C_{12})$-cycloalkyl $(C_1 C_8)$-alkyl, $(C_6–C_{14})$-aryl, $(C_6–C_{14})$-aryl-$(C_1–C_8)$-alkyl, the radical Het- or Het $(C_1–C_8)$-alkyl, where alkyl radicals can be monosubstituted or polysubstituted by fluorine and the radicals $R^{21}$ can be identical or different if they occur several times;

$R^{22}$ is $(C_3–C_{12})$-cycloalkyl, $(C_3–C_{12})$-cycloalkyl-$(C_1–C_8)$-alkyl, $(C_6–C_{14})$-aryl, the radical Het- or Het $(C_1–C_8)$-alkyl, where alkyl radicals can be monosubstituted or polysubstituted by fluorine;

$R^{23}$ is $(C_1–C_8)$-alkyl, $(C_3 C_{12})$-cycloalkyl, $(C_3–C_{12})$-cycloalkyl-$(C_1–C_8)$-alkyl, $(C_6–C_{14})$-aryl, $(C_6 C_{14})$-aryl-$(C_1–C_8)$-alkyl, the radical Het- or Het-$(C_1–C_8)$-alkyl, where alkyl radicals can be monosubstituted or polysubstituted by fluorine;

$R^{24}$ $(C_3–C_{12})$-cycloalkyl, $(C_3–C_{12})$-cycloalkyl-$(C_1–C_8)$ alkyl, $(C_6–C_{14})$-aryl, $(C_6–C_{14})$-aryl-$(C_1–C_8)$-alkyl, the radical Het- or Het-$(C_1–C_8)$-alkyl, where alkyl radicals can be monosubstituted or polysubstituted by fluorine;

$R^{25}$ has the meanings of $R^{21}$, where the radicals $R^{25}$ can be identical or different;

$R^{26}$ has the meanings of $R^{21}$ or HO-$((C_1–C_8)$-alkyl), where alkyl radicals can be monosubstituted or polysubstituted by fluorine;

$R^{27}$ is hydrogen, $(C_3–C_{12})$-cycloalkyl, $(C_3–C_{12})$-cycloalkyl-$(C_1–C_8)$-alkyl, $(C_6–C_{14})$-aryl-$(C_1–C_8)$-alkyl, the radical Het- or Het $(C_1–C_8)$-alkyl, where alkyl radicals can be monosubstituted or polysubstituted by fluorine;

$R^{28}$ is one of the radicals $R^{21}$—, $R^{21}O$—, $R^{20}N(R^{26})$—, $R^{21}C(O)$—, $R^{21}O$—$C(O)$—, $((C_1–C_{18})$-alkyl-O—$C(O)$-$((C_1–C_6)$-alkyl)-O—$C(O)$—, $R^{21}N(R^{21})$—$C(O)$—, $R^{21}N(R^{21})$—$C(–N(R^{21}))$— or $R^{21}C(O)$—N $(R^{21})$—;

Het is a mono- or polycyclic, 4- to 14-membered, aromatic or nonaromatic ring which contains 1, 2, 3 or 4 identical or different heteroatoms from the group consisting of N, O and S as ring members and can optionally be substituted by one or more, identical or different substituents;

b, c, d and f independently of one another are 0 or 1, but cannot all simultaneously be 0;

e, g and h independently of one another are 0, 1, 2, 3, 4, 5 or 6;

in all their stereoisomeric forms and mixtures thereof in any ratio, and/or of their physiologically tolerable salts together with one or more physiologically tolerable carriers and/or additives.

2. The method as claimed in claim 1, wherein

W is $R^1$—A—$C(R^{13})$ or $R^1$—A—CH—C;

Y is a carbonyl;

Z is $N(R^0)$;

A is a bivalent radical from the group consisting of $(C_1–C_6)$-alkylene, $(C_3–C_{12})$-cycloalkylene, $(C_1–C_6)$-alkylene-$(C_3–C_{12})$-cycloalkyl, phenylene, phenylene-$(C_1–C_6)$-alkyl, $(C_1–C_6)$-alkylenephenyl, $(C_1–C_6)$-alkylenephenyl-$(C_1–C_6)$-alkyl, phenylene-$(C_2–C_6)$-alkenyl or a bivalent radical of a 5- or 6-membered saturated or unsaturated ring which can contain 1 or 2 nitrogen atoms and can be mono- or disubstituted by $(C_1–C_6)$-alkyl or doubly bonded oxygen or sulfur;

B is a bivalent radical from the group consisting of $(C_1–C_6)$-alkylene, $(C_2–C_6)$-alkenylene, phenylene, phenylene-$(C_1–C_3)$-alkyl, $(C_1–C_3)$-alkylene-phenyl;

D is $C(R^2)(R^3)$, $N(R^3)$ or CH=$C(R^3)$;

E is tetrazolyl, $(R^8O)_2P(O)$, HOS$(O)_2$, $R^0$NHS$(O)_2$ or $R^{10}CO$; R and $R^0$ independently of one another are hydrogen, $(C_1–C_8)$-alkyl, $(C_3–C_{12})$-cycloalkyl, $(C_3–C_{12})$-cycloalkyl-$(C_1–C_8)$-alkyl, optionally substituted $(C_6–C_{14})$-aryl, $(C_6–C_{14})$-aryl-$(C_1–C_8)$-alkyl optionally substituted in the aryl radical, optionally substituted heteroaryl or heteroaryl-$(C_1–C_8)$-alkyl optionally substituted in the heteroaryl radical, where alkyl radicals can be mono- or polysubstituted by fluorine;

$R^1$ is hydrogen, $(C_1–C_{10})$-alkyl, which can optionally be monosubstituted or polysubstituted by fluorine, $(C_3–C_{12})$-cycloalkyl, $(C_3–C_{12})$-cycloalkyl-$(C_1–C_8)$-alkyl, optionally substituted $R^{21}$-$((C_6–C_{14})$-aryl), $(R^{21}$-$((C_6–C_{14})$-aryl))-$(C_1–C_8)$-alkyl optionally substituted in the aryl radical, the radical Het-, Het-$(C_1–C_8)$-alkyl or one of the radicals $R^{21}O$—, $R^{22}O$—NH—, $R^{21}O$—$N(R^{23})$—, $R^{24}$NH—, $R^{25}N(R^{25})$—, HO-$((C_1–C_8)$-alkyl-$N(R^{26})$—, $R^{27}C(O)$—NH—, $R^{21}C(O)$—$N(R^{23})$—, $R^{21}C(O)$—, $R^{21}O$—$C(O)$—, $R^{28}N(R^{21})$—$C(O)$—, $R^{21}O$—N=, O= and S=;

$R^2$ is hydrogen, $(C_1–C_8)$-alkyl, optionally substituted $(C_6–C_{14})$-aryl, $(C_6–C_{14})$-aryl-$(C_1–C_8)$-alkyl optionally substituted in the aryl radical or $(C_3–C_8)$-cycloalkyl;

$R^3$ is hydrogen, $(C_1–C_8)$-alkyl, optionally substituted $(C_6–C_{14})$-aryl, $(C_6–C_{14})$-aryl $(C_1–C_8)$-alkyl, optionally substituted in the aryl radical, $(C_3 C_8)$ cycloalkyl, $(C_2–C_8)$-alkenyl, $(C_2–C_8)$-alkynyl, $(C_2–C_8)$-alkenylcarbonyl, $(C_2 C_8)$ alkynylcarbonyl, pyridyl, $R^{11}$NH, $R^4$CO, COOR$^4$, CON(CH$_3$)$R^4$, CONHR$^4$, CSNHR$^4$, COOR$^{15}$, CON(CH$_3$)$R^{15}$ or CONHR$^{15}$;

$R^4$ is hydrogen or $(C_1 C_{28})$ alkyl which can optionally be mono- or polysubstituted by identical or different radicals from the group consisting of hydroxyl, hydroxycarbonyl, aminocarbonyl, mono- or di-$((C_1–C_{18})$-alkyl)-aminocarbonyl, amino $(C_2 C_{18})$ alkylaminocarbonyl, amino-$(C_1–C_3)$-alkylphenyl-$(C_1 C_3)$ alkylaminocarbonyl, $(C_1–C_{18})$-alkylcarbonylamino-$(C_1–C_3)$-alkylphenyl-$(C_1 C_3)$-alkylaminocarbonyl, $(C_1–C_{18})$-alkylcarbonylamino-$(C_2–C_{18})$-alkylaminocarbonyl, $(C_6–C_{14})$-aryl-$(C_1–C_8)$-alkoxycarbonyl which can also be substituted in the aryl radical, amino, mercapto, $(C_1–C_{18})$-alkoxy, $(C_1–C_{18})$-alkoxycarbonyl, optionally substituted $(C_3–C_8)$-cycloalkyl, HOS$(O)_7$-$(C_1–C_3)$-alkyl, $R^9$NHS$(O)_2$-$(C_1–C_3)$-alkyl, $(R^8O)_2P(O)$-$(C_1–C_3)$-alkyl, tetrazolyl-$(C_1–C_3)$-alkyl, halogen, nitro, trifluoromethyl and the radical $R^5$;

$R^5$ is optionally substituted $(C_6–C_{14})$-aryl, $(C_6–C_{14})$-aryl-$(C_1–C_8)$-alkyl optionally substituted in the aryl radical, a mono- or bicyclic 5- to 12-membered heterocyclic ring which can be aromatic, partially hydrogenated or completely hydrogenated and which can contain one, two or three identical or different heteroatoms from the group consisting of nitrogen, oxygen and sulfur, a radical $R^6$ or a radical $R^6CO$—, where the aryl radical and, independently thereof, the heterocyclic radical can be mono- or polysubstituted by identical or different radicals from the group consisting of $(C_1–C_{18})$-alkyl, $(C_1–C_{18})$-alkoxy, halogen, nitro, amino or trifluoromethyl;

$R^6$ is $R^7R^8N$, $R^7O$ or $R^7S$ or an amino acid side chain, a natural or unnatural amino acid, imino acid, optionally N-$(C_1-C_8)$-alkylated or N-$((C_6-C_{14})$-aryl-$(C_1-C_8)$-alkylated) azaamino acid or a dipeptide radical which can also be substituted in the aryl radical and/or in which the peptide bond can be reduced to —NH—$CH_2$—, and their esters and amides, where hydrogen or hydroxymethyl can optionally stand in place of free functional groups and/or where free functional groups can be protected by protective groups customary in peptide chemistry;

$R^7$ is hydrogen, $(C_1-C_{18})$-alkyl, $(C_6-C_{14})$-aryl-$(C_1-C_8)$-alkyl, $(C_1-C_{18})$-alkylcarbonyl, $(C_1-C_{18})$-alkoxycarbonyl, $(C_6-C_{14})$-arylcarbonyl, $(C_6-C_{14})$-aryl-$(C_1-C_8)$-alkylcarbonyl or $(C_6-C_{14})$-aryl-$(C_1-C_{18})$-alkyloxycarbonyl, where the alkyl groups can optionally be substituted by an amino group and/or where the aryl radicals can be mono- or polysubstituted by identical or different radicals from the group consisting of $(C_1-C_8)$-alkyl, $(C_1-C_8)$-alkoxy, halogen, nitro, amino and trifluoromethyl, or is a natural or unnatural amino acid, imino acid, optionally N $(C_1\ C_8)$ alkylated or N $((C_6\ C_{14})$ aryl $(C_1\ C_8)$ alkylated) azaamino acid or a dipeptide radical which can also be substituted in the aryl radical and/or in which the peptide bond can be reduced to —NH—$CH_2$—;

$R^8$ is hydrogen, $(C_1-C_{18})$-alkyl, optionally substituted $(C_6-C_{14})$-aryl or $(C_6-C_{14})$-aryl-$(C_1-C_8)$-alkyl which can also be substituted in the aryl radical;

$R^9$ is hydrogen, aminocarbonyl, $(C_1-C_{18})$-alkylaminocarbonyl, $(C_3-C_8)$-cycloalkylaminocarbonyl, optionally substituted $(C_6-C_{14})$-arylaminocarbonyl, $(C_1-C_{18})$-alkyl, optionally substituted $(C_6-C_{14})$-aryl or $(C_3-C_8)$-cycloalkyl;

$R^{10}$ is hydroxyl, $(C_1-C_{18})$-alkoxy, $(C_6-C_{14})$-aryl-$(C_1-C_8)$-alkoxy which can also be substituted in the aryl radical, optionally substituted $(C_6-C_{14})$-aryloxy, amino or mono- or di-$((C_1-C_{18})$-alkyl)amino;

$R^{11}$ is hydrogen, $(C_1-C_{18})$-alkyl, $R^{12}CO$, optionally substituted $(C_6-C_{14})$-aryl-$S(O)_2$, $(C_1-C_{18})$-alkyl-$S(O)_2$, $(C_6-C_{14})$-aryl-$(C_1-C_8)$-alkyl optionally substituted in the aryl radical, $R^0NHS(O)_2$ or the radical $R^{15}$;

$R^{12}$ is hydrogen, $(C_1-C_{18})$-alkyl, $(C_2-C_8)$-alkenyl, $(C_2-C_8)$-alkynyl, optionally substituted $(C_6-C_{14})$-aryl, $(C_1-C_{18})$-alkoxy, $(C_6-C_{14})$-aryl-$(C_1-C_8)$-alkoxy which can also be substituted in the aryl radical, optionally substituted $(C_6-C_{14})$-aryloxy, amino or mono- or di-$((C_1-C_{18})$-alkyl)amino, the radical $R^{15}$ or the radical $R^{15}$—O—;

$R^{13}$ is hydrogen, $(C_1-C_6)$-alkyl, $(C_6-C_{14})$-aryl-$(C_1-C_8)$-alkyl optionally substituted in the aryl radical or $(C_3-C_8)$-cycloalkyl;

$R^{15}$ is $R^{16}$-$(C_1-C_6)$-alkyl or $R^{16}$;

$R^{16}$ is a 6- to 24-membered bicyclic or tricyclic radical which is saturated or partially unsaturated and which can also contain one to four identical or different heteroatoms from the group consisting of nitrogen, oxygen and sulfur and which can also be substituted by one or more identical or different substituents from the group consisting of $(C_1-C_4)$-alkyl and oxo;

$R^{21}$ is hydrogen, $(C_1-C_8)$-alkyl, $(C_3-C_{12})$-cycloalkyl, $(C_3-C_{12})$-cycloalkyl-$(C_1-C_8)$-alkyl, $(C_6-C_{14})$-aryl, $(C_6-C_{14})$-aryl-$(C_1-C_8)$-alkyl, the radical Het- or Het-$(C_1-C_8)$-alkyl, where alkyl radicals can be monosubstituted or polysubstituted by fluorine and the radicals $R^{21}$ can be identical or different if they occur several times;

$R^{22}$ is $(C_3-C_{12})$-cycloalkyl, $(C_3-C_{12})$-cycloalkyl-$(C_1-C_8)$-alkyl, $(C_6-C_{14})$-aryl, the radical Het- or Het-$(C_1-C_8)$-alkyl, where alkyl radicals can be monosubstituted or polysubstituted by fluorine;

$R^{23}$ is $(C_1-C_8)$-alkyl, $(C_3-C_{12})$-cycloalkyl, $(C_3-C_{12})$-cycloalkyl-$(C_1-C_8)$-alkyl, $(C_6-C_{14})$-aryl, $(C_6-C_{14})$-aryl-$(C_1-C_8)$-alkyl, the radical Het- or Het-$(C_1-C_8)$-alkyl, where alkyl radicals can be monosubstituted or polysubstituted by fluorine;

$R^{24}$ $(C_3-C_{12})$-cycloalkyl, $(C_3-C_{12})$-cycloalkyl-$(C_1-C_8)$-alkyl, $(C_6-C_{14})$-aryl, $(C_6-C_{14})$-aryl-$(C_1-C_8)$-alkyl, the radical Het- or Het-$(C_1-C_8)$-alkyl, where alkyl radicals can be monosubstituted or polysubstituted by fluorine;

$R^{25}$ has the meanings of $R^{23}$, where the radicals $R^{23}$ can be identical or different;

$R^{26}$ has the meanings of $R^{21}$ or HO-$((C_1-C_8)$-alkyl), where alkyl radicals can be monosubstituted or polysubstituted by fluorine;

$R^{27}$ is hydrogen, $(C_3-C_{12})$-cycloalkyl, $(C_3-C_{12})$-cycloalkyl-$(C_1-C_8)$-alkyl, $(C_6-C_{14})$-aryl-$(C_1-C_6)$-alkyl, the radical Het- or Het-$(C_1-C_8)$-alkyl, where alkyl radicals can be monosubstituted or polysubstituted by fluorine;

$R^{28}$ is one of the radicals $R^{21}$—, $R^{21}O$—, $R^{20}N(R^{26})$—, $R^{21}C(O)$, $R^{21}O$—C(O)—, $((C_1-C_{18})$-alkyl-O—C(O)-$((C_1-C_6)$-alkyl)-O—C(O)—, $R^{21}N(R^{21})$—C(O)—, $R^{21}N(R^{21})$-C(=N($R^{21}$))— or $R^{21}C(O)$—N($R^{21}$)—;

Het is a mono- or polycyclic, 4- to 14-membered, aromatic or nonaromatic ring which contains 1, 2, 3 or 4 identical or different heteroatoms from the group consisting of N, O and S as ring members and can optionally be substituted by one or more, identical or different substituents;

b, c, d and f independently of one another are 0 or 1, but cannot all simultaneously be 0;

e, g and h independently of one another are 0, 1, 2, 3, 4, 5 or 6;

in all their stereoisomeric forms and mixtures thereof in any ratio, and/or of their physiologically tolerable salts.

3. The method as claimed in claim 1, wherein $R^0$ is $(C_1-C_8)$-alkyl, $(C_3-C_{12})$-cycloalkyl, $(C_3-C_{12})$-cycloalkyl-$(C_1-C_8)$ alkyl, $(C_6-C_{14})$-aryl, $(C_6-C_{14})$-aryl-$(C_1-C_8)$-alkyl optionally substituted in the aryl radical, optionally substituted heteroaryl or heteroaryl-$(C_1-C_8)$-alkyl optionally substituted in the heteroaryl radical;

in all their stereoisomeric forms and mixtures thereof in any ratio, and/or of their physiologically tolerable salts.

4. The method as claimed in claim 1, wherein simultaneously W is $R^1$—A—CH—C and therein A is a phenylene radical or a methylenephenyl radical, or W is $R^1$—A—C ($R^{13}$) and therein A is a bivalent radical from the group consisting of methylene, ethylene, trimethylene, tetramethylene, pentamethylene, cyclohexylene, phenylene, phenylenemethyl, methylenephenyl, methylenephenylmethyl;

B is a bivalent radical from the group consisting of methylene, ethylene, trimethylene, tetramethylene, vinylene, phenylene, or substituted methylene or ethylene;

E is $R^{10}CO$;

R is hydrogen, $(C_1-C_6)$-alkyl or benzyl;

$R^0$ is $(C_1-C_8)$-alkyl, $(C_3-C_8)$-cycloalkyl, optionally substituted $(C_6-C_{14})$-aryl or $(C_6-C_{14})$-aryl-$(C_1-C_8)$-alkyl optionally substituted in the aryl radical;

$R^1$ is one of the radicals $R^{21}O$—, $R^{24}NH$—, $R^{25}N(R^{25})$—, HO-$((C_1-C_8)$-alkyl-N($R^{26}$)—, $R^{21}O$—C(O)— and $R^{28}N(R^{21})$—C(O)—, $R^2$ is hydrogen or $(C_1\text{-}C_8)$ alkyl;

$R^3$ is $(C_1\text{-}C_8)$ alkyl, optionally substituted $(C_6\text{-}C_{14})$ aryl, $(C_6\text{-}C_{14})$ aryl $(C_1\text{-}C_8)$ alkyl, $(C_3\text{-}C_8)$-cycloalkyl, $(C_2\text{-}C_8)$-alkenyl, $(C_2\text{-}C_8)$ alkynyl, pyridyl, $R^{11}NH$, $R^4CO$, $COOR^4$, $CONHR^4$, $CSNHR^4$, $COOR^{15}$ and $CONHR^{15}$;

and e, g and h independently of one another are the numbers 0, 1, 2 or 3;

in all their stereoisomeric forms and mixtures thereof in any ratio, and/or of their physiologically tolerable salts.

5. The method as claimed in claim 1, wherein W is $R^1\text{—}A\text{—}C(R^{13})$ and $R^{13}$ is $(C_1\text{-}C_6)$-alkyl, $(C_6\text{-}C_{14})$-aryl-$(C_1\text{-}C_8)$-alkyl optionally substituted in the aryl radical or $(C_3\text{-}C_8)$-cycloalkyl;

in all their stereoisomeric forms and mixtures thereof in any ratio, and/or of their physiologically tolerable salts.

6. The method as claimed in claim 1, wherein $R^3$ is optionally substituted $(C_6\text{-}C_{14})$-aryl, $COOR^4$, $R^{11}NH$ or $CONHR$, where —$NHR^4$ is the radical of an α-amino acid, its ω-amino-$(C_2\text{-}C_8)$-alkylamide, its $(C_1\text{-}C_8)$-alkyl ester or its $(C_6\text{-}C_{14})$-aryl-$(C_1\text{-}C_4)$-alkyl ester;

in all their stereoisomeric forms and mixtures thereof in any ratio, and/or of their physiologically tolerable salts.

7. The method as claimed in claim 1, wherein simultaneously

W is $R^1\text{—}A\text{—}C(R^{13})$;

Y is a carbonyl group;

Z is $N(R^0)$;

A is ethylene, trimethylene, tetramethylene, pentamethylene, cyclohexylene, phenylene, phenylenemethyl, methylenephenyl or methylenephenylmethyl;

B is an unsubstituted or substituted methylene radical;

D is $C(R^2)(R^3)$;

E is $R^{10}CO$;

R is hydrogen or $(C_1\text{-}C_4)$-alkyl;

$R^0$ is $(C_1\text{-}C_8)$-alkyl, $(C_3\text{-}C_8)$-cycloalkyl, optionally substituted $(C_6\text{-}C_{14})$ aryl or $C_6\text{-}C_{14}$)-aryl-$(C_1\text{-}C_8)$-alkyl optionally substituted in the aryl radical;

$R^1$ is the radical $R^{28}N(R^{21})\text{—}C(O)\text{—}$;

$R^2$ is hydrogen;

$R^3$ is the radical $CONHR^4$;

$R^4$ is methyl which is substituted by hydroxycarbonyl and a radical from the group consisting of $(C_1\text{-}C_4)$-alkyl, phenyl and benzyl, or is methyl which is substituted by $(C_1\text{-}C_8)$-alkoxycarbonyl and a radical from the group consisting of $(C_1\text{-}C_4)$-alkyl, phenyl and benzyl;

$R^{10}$ is hydroxyl or $(C_1\text{-}C_8)$-alkoxy;

$R^{13}$ is $(C_1\text{-}C_6)$-alkyl, $(C_3\text{-}C_7)$-cycloalkyl or benzyl;

b, c and d are 1 and c, f and g are 0;

b is 1 or 2;

in all their stereoisomeric forms and mixtures thereof in any ratio, and/or of their physiologically tolerable salts.

8. The method as claimed in claim 1, wherein simultaneously W is $R^1\text{—}A\text{—}CH\text{=}C$ and therein A is a phenylene radical or a methylenephenyl radical, or W is $R^1\text{—}A\text{—}C(R^{13})$ and therein A is a bivalent radical from the group consisting of methylene, ethylene, trimethylene, tetramethylene, pentamethylene, cyclohexylene, phenylene, phenylenemethyl, methylenephenyl, methylenephenylmethyl;

H is a bivalent radical from the group consisting of methylene, ethylene, trimethylene, tetramethylene, vinylene, phenylene or substituted methylene or ethylene;

E is $R^{10}$ CO;

R is hydrogen or $(C_1\text{-}C_6)$-alkyl;

$R^0$ is $(C_1\text{-}C_8)$-alkyl, $(C_3\text{-}C_8)$-cycloalkyl, optionally substituted $(C_6\text{-}C_{14})$-aryl or $(C_6\text{-}C_{14})$-aryl-$(C_1\text{-}C_8)$-alkyl optionally substituted in the aryl radical;

$R^1$ is one of the radicals $R^{21}O\text{—}$, $R^{21}O\text{—}N(R^{23})\text{—}$, $R^{24}NH\text{—}$, $R^{25}N(R^{25})\text{—}$, $HO\text{-}((C_1\text{-}C_8)\text{-alkyl})\text{-}N(R^{26})\text{—}$, $R^{21}O\text{—}C(O)\text{—}$ and $R^{28}N(R^{21})\text{—}C(O)\text{—}$;

$R^2$ is hydrogen or $(C_1\text{-}C_8)$-alkyl;

$R^3$ is $CONHR^{15}$ or $CONHR^4$ where $R^4$ herein is a $(C_1\text{-}C_8)$-alkyl radical which is unsubstituted or substituted by one or more $(C_6\text{-}C_{14})$-aryl radicals;

$R^{15}$ is $R^{16}\text{-}(C_1\text{-}C_6)$-alkyl or $R^{16}$, where $R^{16}$ is a 7- to 12-membered bridged bicyclic or tricyclic radical which is saturated or partially unsaturated and which can also contain one to four identical or different heteroatoms from the group consisting of nitrogen, oxygen and sulfur and which can also be substituted by one or more identical or different substituents from the group consisting of $(C_1\text{-}C_4)$-alkyl and oxo; and e, g and h independently of one another are the numbers 0, 1, 2 or 3 and b, c and d are 1;

in all their stereoisomeric forms and mixtures thereof in any ratio, and/or of their physiologically tolerable salts.

9. The method as claimed in claim 1, wherein

W is $R^1\text{—}A\text{—}C(R^{13})$;

Y is a carbonyl group;

Z is $N(R^0)$;

A is ethylene, trimethylene, tetramethylene, pentamethylene, cyclohexylene, phenylene, phenylenemethyl, methylenephenyl or methylenephenylmethyl;

B is an unsubstituted or substituted methylene radical;

D is $C(R^2)(R^3)$;

E is $R^{10}CO$;

R is hydrogen or $(C_1\text{-}C_4)$-alkyl;

$R^0$ is $(C_1\text{-}C_8)$-alkyl, $(C_3\text{-}C_8)$-cycloalkyl, optionally substituted $(C_6\text{-}C_{14})$ aryl or $C_6\text{-}C_{14}$-aryl-$(C_1\text{-}C_8)$-alkyl optionally substituted in the aryl radical;

$R^1$ is the radical $R^{28}N(R^{21})\text{—}C(O)\text{—}$;

$R^2$ is hydrogen;

$R^3$ is $CONHR^{15}$ or $CONHR^4$ where $R^4$ herein is a $(C_1\text{-}C_6)$ alkyl radical which is unsubstituted or substituted by one or more $(C_6\text{-}C_{10})$ aryl radicals;

$R^{10}$ is hydroxyl or $(C_1\text{-}C_8)$ alkoxy;

$R^{13}$ is $(C_1\text{-}C_6)$-alkyl, $(C_3\text{-}C_7)$-cycloalkyl or benzyl;

$R^{15}$ is an adamantyl radical or an adamantylmethyl radical;

b, c and d are 1 and e, f and g are 0;

h is 1 or 2;

in all their stereoisomeric forms and mixtures thereof in any ratio, and/or of their physiologically tolerable salts.

10. The method as claimed in claim 1, wherein simultaneously

W is $R^1\text{—}A\text{—}C(R^{13})$;

Y is a carbonyl group;

Z is $N(R^0)$;

A is ethylene, trimethylene, tetramethylene, pentamethylene, cyclohexylene, phenylene, phenylenemethyl, methylenephenyl methylenephenylmethyl;

B is an unsubstituted or substituted methylene radical or ethylene radical;

D is $C(R^2)(R^3)$;

E is $R^{10}CO$;

R is hydrogen or $(C_1–C_4)$-alkyl;

$R^0$ is $(C_1–C_8)$-alkyl, $(C_3–C_8)$-cycloalkyl, optionally substituted $(C_6–C_{14})$-aryl or $(C_6–C_{14})$-aryl-$(C_1–C_8)$-alkyl which is optionally substituted in the aryl radical;

$R^1$ is one of the radicals $R^{21}O—$, $R^{24}NH—$, $R^{25}N(R^{25})—$, $HO-((C_1–C_8)$-alkyl-$N(R^{26}))$, $R^{21}O—C(O)—$ and $R^{28}N(R^{21})—C(O)—$;

$R^2$ is hydrogen;

$R^3$ is an unsubstituted phenyl or naphthyl radical, a phenyl radical or naphthyl radical substituted by one, two or three identical or different radicals from the group consisting of $(C_1–C_4)$-alkyl, $(C_1–C_4)$-alkoxy, hydroxyl, halogen, trifluoromethyl, nitro, methylenedioxy, ethylenedioxy, hydroxycarbonyl, $(C_1–C_4)$-alkoxycarbonyl, aminocarbonyl, cyano, phenyl, phenoxy and benzyloxy, a pyridyl radical, a $(C_1–C_4)$-alkyl radical, a $(C_2–C_4)$-alkenyl radical, a $(C_2–C_4)$-alkynyl radical or a $(C_3–C_6)$-cycloalkyl radical;

$R^{10}$ is hydroxyl or $(C_1–C_8)$-alkoxy;

$R^{13}$ is $(C_1–C_6)$-alkyl, $(C_3–C_7)$-cycloalkyl or benzyl;

b, c and d are 1 and e, f and g are 0;

h is 1 or 2;

in all their stereoisomeric forms and mixtures thereof in any ratio, and/or of their physiologically tolerable salts.

11. The method as claimed in claim 1, wherein simultaneously

W is $R^1—A—C(R^{13})$;

Y is a carbonyl group;

Z is $N(R^0)$;

A is ethylene, trimethylene, tetramethylene, pentamethylene, cyclohexylene, phenylene, phenylenemethyl, methylenephenyl or methylenephenylmethyl;

B is an unsubstituted or substituted methylene radical or ethylene radical;

D is $C(R^2)(R^3)$;

E is $R^{10}CO$;

R is hydrogen or $(C_1\ C_4)$ alkyl;

$R^0$ is $(C_1–C_8)$-alkyl, $(C_3–C_8)$-cycloalkyl, optionally substituted $(C_6–C_{14})$-aryl or $(C_6–C_{14})$-aryl-$(C_1–C_8)$-alkyl optionally substituted in the aryl radical;

$R^1$ is one of the radicals $R^{21}O—$, $R^{24}NH—$, $R^{25}N(R^{25})—$, $HO-((C_1–C_8)$-alkyl-$N(R^{20}))—$, $R^{21}O—C(O)—$ and $R^{28}N(R^{21})—C(O)—$;

$R^2$ is hydrogen;

$R^3$ is $R^{11}NH$;

$R^{10}$ is hydroxyl or $(C_1–C_8)$-alkoxy;

$R^{13}$ is $(C_1–C_6)$-alkyl, $(C_3–C_7)$-cycloalkyl or benzyl;

b, c, d and e are 1 and f and g are 0;

h is 0;

in all their stereoisomeric forms and mixtures thereof in any ratio, and/or of their physiologically tolerable salts.

12. The method as claimed in claim 1, in which a substituted methylene radical or substituted ethylene radical representing the group B carries as a substituent a radical from the group consisting of $(C_1–C_8)$-alkyl, $(C_2–C_6)$-alkenyl, $(C_2–C_6)$-alkynyl, and $(C_3–C_8)$-cycloalkyl;

in all their stereoisomeric forms and mixtures thereof in any ratio, and/or of their physiologically tolerable salts.

13. The method as claimed in claim 1, in which B is an unsubstituted methylene radical or a methylene radical which is substituted by a $(C_1–C_8)$-alkyl radical;

in all their stereoisomeric forms and mixtures thereof in any ratio, and/or of their physiologically tolerable salts.

14. A method for the treatment of rheumatoid arthritis, inflammatory bowel disease, systemic lupus erythematosus or inflammatory disorders of the central nervous system comprising administering to a subject in need thereof a preparation comprising a VLA-4-antagonizing-effective amount of one or more compounds of the formula I

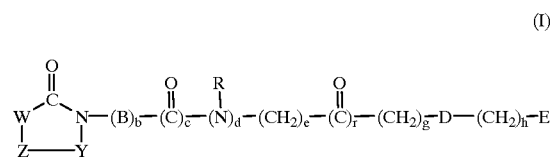

(I)

W is $R^1—A—C(R^{13})$ or $R^1—A\ CH=C$;

Y is a carbonyl;

Z is $N(R^0)$;

A is a bivalent radical from the group consisting of $C_1–C_6$-alkylene, $(C_3–C_{12})$-cycloalkylene, $(C_1\ C_6)$-alkylene-$(C_3–C_{12})$-cycloalkyl, phenylene, phenylene-$(C_1–C_6)$-alkyl, $(C_1\ C_6)$-alkylenephenyl, $(C_1–C_6)$-alkylenephenyl-$(C_1–C_6)$-alkyl, phenylene-$(C_2–C_6)$-alkenyl or a bivalent radical of a 5- or 6-membered saturated or unsaturated ring which can contain 1 or 2 nitrogen atoms and can be mono- or disubstituted by $(C_1–C_6)$-alkyl or doubly bonded oxygen or sulfur;

H is a bivalent radical from the group consisting of $(C_1–C_6)$-alkylene, $(C_2–C_6)$-alkenylene, phenylene, phenylene-$(C_1–C_3)$-alkyl, $(C_1–C_3)$-alkylenephenyl, where the bivalent $(C_1–C_6)$-alkylene radical can be unsubstituted or substituted by a radical from the group consisting of $(C_1–C_8)$-alkyl, $(C_2–C_8)$-alkenyl, $(C_2–C_8)$-alkynyl, $(C_3–C_{10})$-cycloalkyl, $(C_3–C_{10})$-cycloalkyl-$(C_1–C_6)$-alkyl, optionally substituted $(C_6–C_{14})$-aryl, $(C_6–C_{14})$-aryl $(C_1–C_6)$-alkyl optionally substituted in the aryl radical, optionally substituted heteroaryl and heteroaryl-$(C_1–C_6)$-alkyl optionally substituted in the heteroaryl radical;

D is $C(R^2)(R^3)$, $N(R^3)$ or $CH=C(R^3)$;

E is tetrazolyl, $(R^8O)_2P(O)$, $HOS(O)_2$, $R^9NHS(O)_2$ or $R^{10}CO$;

R is hydrogen, $(C_1–C_8)$-alkyl, $(C_3–C_{12})$-cycloalkyl, $(C_3\ C_{12})$-cycloalkyl-$(C_1–C_8)$-alkyl, optionally substituted $(C_6–C_{14})$-aryl, $(C_6–C_{14})$-aryl-$(C_1–C_8)$-alkyl optionally substituted in the aryl radical, optionally substituted heteroaryl or heteroaryl-$(C_1–C_8)$-alkyl optionally substituted in the heteroaryl radical, where alkyl radicals can be mono- or polysubstituted by fluorine;

$R^0$ is hydrogen, $(C_1–C_8)$-alkyl, $(C_3–C_{12})$-cycloalkyl, $(C_3–C_{12})$-cycloalkyl-$(C_1–C_8)$-alkyl, $(C_6–C_{12})$-bicycloalkyl, $(C_6\ C_{12})$-bicycloalkyl-$(C_1–C_8)$-alkyl, $(C_6–C_{12})$-tricycloalkyl, $(C_6–C_{12})$-tricycloalkyl $(C_1–C_8)$-alkyl, optionally substituted $(C_6–C_{14})$-aryl, $(C_6–C_{14})$-aryl-$(C_1–C_8)$-alkyl optionally substituted in the aryl radical, optionally substituted hetaryl, heteroaryl-$(C_1–C_8)$-alkyl optionally substituted in the heteroaryl radical, CHO, $(C_1–C_8)$-alkyl-CO, $(C_3–C_{12})$-cycloalkyl-CO, $(C_3–C_{12})$-cycloalkyl $(C_1–C_8)$-alkyl-CO, $(C_6–C_{12})$-bicycloalkyl-CO, $(C_6–C_{12})$-bicycloalkyl-$(C_1–C_8)$-alkyl-CO, $(C_6–C_{12})$-tricycloalkyl-CO, $(C_6–C_{12})$-tricycloalkyl-$(C_1–C_8)$-alkyl-CO, optionally substituted $(C_6–C_{14})$-aryl-CO, $(C_6–C_{14})$-aryl-$(C_1–C_8)$-alkyl-CO optionally substituted in the aryl radical, optionally substituted heteroaryl CO, heteroaryl-$(C_1-C_8)$-alkyl-CO optionally substituted in the heteroaryl radical, $(C_1-C_8)$-alkyl-S(O)$_n$, $(C_3-C_{12})$-cycloalkyl-S(O)$_n$, $(C_3-C_{12})$-cycloalkyl-$(C_1-C_8)$-alkyl-S(O)$_n$, $(C_6-C_{12})$-bicycloalkyl-S(O)$_n$, $(C_6-C_{12})$-bicycloalkyl-$(C_1-C_8)$ alkyl-S(O)$_n$, $(C_6-C_{12})$-tricycloalkyl-S(O)$_n$, $(C_6-C_{12})$-tricycloalkyl-$(C_1-C_8)$-alkyl S(O)$_n$, optionally substituted $(C_6-C_{14})$-aryl-S(O)$_n$, $(C_6-C_{14})$-aryl-$(C_1-C_8)$ alkyl-S(O)$_n$ optionally substituted in the aryl radical, optionally substituted hetaryl-S(O)$_n$ or heteroaryl-$(C_1-C_8)$-alkyl-S(O)$_n$ optionally substituted in the heteroaryl radical, where n is 1 or 2;

$R^1$ is hydrogen, $(C_1-C_{10})$-alkyl, which can optionally be mono substituted or polysubstituted by fluorine, $(C_3-C_{12})$-cycloalkyl, $(C_3-C_{12})$-cycloalkyl $(C_1-C_8)$-alkyl, optionally substituted $R^{21}$-$((C_6-C_{14})$-aryl), $(R^{21}$-$((C_6-C_{14})$-aryl)) $(C_1-C_8$-alkyl optionally substituted in the aryl radical, the radical Het-, Het-$(C_1-C_8)$-alkyl or one of the radicals $R^{21}O$—, $R^{22}O$—NH—, $R^{21}O$—N$(R^{23})$—, $R^{24}NH$—, $R^{25}N(R^{25})$—, HO—$((C_1-C_8)$-alkyl)-N$(R^{26})$—, $R^{27}C(O)$—NH—, $R^{21}C(O)$—N$(R^{23})$—, $R^{21}C(O)$—, $R^{21}O$—C(O)—, $R^{28}N(R^{21})$—C(O)—, $R^{21}O$—NH, O| and S|;

$R^2$ is hydrogen, $(C_1-C_8)$-alkyl, optionally substituted $(C_6-C_{14})$-aryl, $(C_6-C_{14})$-aryl-$(C_1-C_8)$-alkyl optionally substituted in the aryl radical or $(C_3-C_8)$ cycloalkyl;

$R^3$ is hydrogen, $(C_1-C_8)$-alkyl, optionally substituted $(C_6-C_{14})$-aryl, $(C_6-C_{14})$-aryl-$(C_1-C_8)$-alkyl optionally substituted in the aryl radical, $(C_3-C_8)$-cycloalkyl, $(C_2-C_8)$-alkenyl, $(C_2-C_8)$-alkynyl, $(C_2-C_8)$-alkenylcarbonyl, $(C_2-C_8)$-alkynylcarbonyl, pyridyl, $R^{11}NH$, $R^4CO$, $COOR^6$, $CON(CH_3)R^4$, $CONHR^4$, $CSNHR^4$, $COOR^{15}$, $CON(CH_3)R^{15}$ or $CONHR^{15}$;

$R^4$ is hydrogen or $(C_1-C_{28})$-alkyl which can optionally be mono- or polysubstituted by identical or different radicals from the group consisting of hydroxyl, hydroxycarbonyl, aminocarbonyl, mono- or di-$((C_1-C_{18})$-alkyl)-aminocarbonyl, amino-$(C_2-C_{18})$-alkylaminocarbonyl, amino $(C_1-C_3)$-alkylphenyl-$(C_1-C_3)$-alkylaminocarbonyl, $(C_1-C_{18})$-alkylcarbonylamino-$(C_1-C_3)$-alkylphenyl $(C_1-C_3)$-alkylaminocarbonyl, $(C_1-C_{18})$-alkylcarbonylamino-$(C_2-C_{18})$-alkylaminocarbonyl, $(C_6-C_{14})$-aryl-$(C_1-C_8)$-alkoxycarbonyl which can also be substituted in the aryl radical, amino, mercapto, $(C_1-C_{18})$-alkoxy, $(C_1-C_{18})$-alkoxycarbonyl, optionally substituted $(C_3-C_8)$-cycloalkyl, HOS(O)$_2$-$(C_1-C_3)$-alkyl, $R^9NHS(O)_2$—$(C_1-C_3)$-alkyl, $(R^8O)_2P(O)$—$(C_1-C_3)$-alkyl, tetrazolyl-$(C_1-C_3)$-alkyl, halogen, nitro, trifluoromethyl or the radical $R^3$;

$R^5$ is optionally substituted $(C_3-C_{14})$-aryl, $(C_6-C_{14})$-aryl-$(C_1-C_8)$-alkyl optionally substituted in the aryl radical, a mono- or bicyclic 5- to 12-membered heterocyclic ring which can be aromatic, partially hydrogenated or completely hydrogenated and which can contain one, two or three identical or different heteroatoms from the group consisting of nitrogen, oxygen and sulfur, a radical $R^6$ or a radical $R^6CO$—, where the aryl radical and, independently thereof, the heterocyclic radical can be mono- or polysubstituted by identical or different radicals from the group consisting of $(C_1-C_{18})$-alkyl, $(C_1-C_{18})$-alkoxy, halogen, nitro, amino and trifluoromethyl;

$R^6$ is $R^7R^8N$, $R^7O$ or $R^7S$ or an amino acid side chain, a natural or unnatural amino acid, imino acid, optionally N—$(C_1-C_8)$-alkylated or N—$((C_6-C_{14})$-aryl-$(C_1-C_8)$-alkylated) azaamino acid or a dipeptide radical which can also be substituted in the aryl radical and/or reduced in the peptide bond to —NH—CH$_2$—, and their esters and amides, where hydrogen or hydroxymethyl can optionally stand in place of free functional groups and/or where free functional groups can be protected by protective groups customary in peptide chemistry;

$R^7$ is hydrogen, $(C_1-C_{18})$-alkyl, $(C_6-C_{14})$-aryl-$(C_1-C_8)$-alkyl, $(C_1-C_{18})$-alkylcarbonyl, $(C_1-C_{18})$-alkoxycarbonyl, $(C_6-C_{14})$-arylcarbonyl, $(C_6-C_{14})$-aryl-$(C_1-C_8)$-alkylcarbonyl or $(C_6-C_{14})$-aryl-$(C_1-C_{18})$-alkyloxycarbonyl, where the alkyl groups can optionally be substituted by an amino group and/or where the aryl radicals can be mono- or polysubstituted by identical or different radicals from the group consisting of $(C_1-C_8)$-alkyl, $(C_1-C_8)$-alkoxy, halogen, nitro, amino and trifluoromethyl, or is a natural or unnatural amino acid, imino acid, optionally N—$(C_1-C_8)$-alkylated or N—$((C_6-C_{14})$-aryl-$(C_1-C_8)$-alkylated) azaamino acid or a dipeptide radical which can also be substituted in the aryl radical and/or reduced in the peptide bond to —NH—CH$_2$—;

$R^8$ is hydrogen, $(C_1-C_{18})$-alkyl, optionally substituted $(C_6-C_{14})$-aryl or $(C_6-C_{14})$-aryl-$(C_1-C_8)$-alkyl which can also be substituted in the aryl radical;

$R^9$ is hydrogen, aminocarbonyl, $(C_1-C_{18})$-alkylaminocarbonyl, $(C_3-C_8)$-cycloalkylaminocarbonyl, optionally substituted $(C_6-C_{14})$-arylaminocarbonyl, $(C_1-C_{18})$-alkyl, optionally substituted $(C_6-C_{14})$-aryl or $(C_3-C_8)$-cycloalkyl;

$R^{10}$ is hydroxyl, $(C_1-C_{18})$-alkoxy, $(C_6-C_{14})$-aryl-$(C_1-C_8)$-alkoxy which can also be substituted in the aryl radical, optionally substituted $(C_6-C_{14})$-aryloxy, amino or mono- or di-$((C_1-C_{18})$-alkyl)amino;

$R^{11}$ is hydrogen, $(C_1-C_{18})$-alkyl, $R^{12}CO$, $R^{12a}CS$, optionally substituted $(C_6-C_{14})$-aryl-S(O)$_2$, $(C_1-C_{18})$-alkyl-S(O)$_2$, $(C_6-C_{14})$-aryl-$(C_1-C_8)$-alkyl optionally substituted in the aryl radical, $R^9NHS(O)_2$ or the radical $R^{15}$;

$R^{12}$ is hydrogen, $(C_1-C_{18})$-alkyl, $(C_2-C_8)$-alkenyl, $(C_2-C_8)$-alkynyl, optionally substituted $(C_6-C_{14})$-aryl, $(C_1-C_{18})$-alkoxy, $(C_6-C_{14})$-aryl-$(C_1-C_8)$-alkoxy which can also be substituted in the aryl radical, optionally substituted $(C_6-C_{14})$-aryloxy, the radical $R^{15}$, the radical $R^{15}$—O—, amino, mono- or di-$((C_1-C_{18})$-alkyl)amino, $(C_2-C_8)$-alkenylamino, $(C_2-C_8)$-alkynylamino, $(C_3-C_{12})$-cycloalkylamino, $(C_3-C_{12})$-cycloalkyl-$(C_1-C_8)$-alkylamino, the radical $R^{15}$—NH—, optionally substituted $(C_6-C_{14})$-aryl-NH, $(C_6-C_{14})$-aryl-$(C_1-C_8)$-alkyl-NH, which can also be substituted in the aryl radical, optionally substituted heteroaryl-NH or heteroaryl-$(C_1-C_8)$-alkyl-NH optionally substituted in the heteroaryl radical;

$R^{12a}$ is amino, mono- or di-$((C_1-C_{18})$-alkyl)-amino, $(C_2-C_8)$-alkenylamino, $(C_2-C_8)$-alkynylamino, $(C_3-C_{12})$-cycloalkylamino, $(C_3-C_{12})$-cycloalkyl-$(C_1-C_8)$-alkylamino, the radical $R^{15}$—NH—, optionally substituted $(C_6-C_{14})$-aryl-NH, $(C_6-C_{14})$-aryl-$(C_1-C_8)$-alkyl-NH, which can also be substituted in the aryl radical, optionally substituted heteroaryl-NH or heteroaryl-$(C_1-C_8)$-alkyl-NH optionally substituted in the heteroaryl radical;

$R^{13}$ is hydrogen, $(C_1-C_6)$-alkyl, $(C_6-C_{14})$-aryl-$(C_1-C_8)$-alkyl optionally substituted in the aryl radical or $(C_3-C_8)$-cycloalkyl;

$R^{15}$ is $R^{16}$—$(C_1$–$C_6)$alkyl or $R^{16}$;

$R^{16}$ is a 6- to 24-membered bicyclic or tricyclic radical which is saturated or partially unsaturated and which can also contain one to four identical or different heteroatoms from the group consisting of nitrogen, oxygen and sulfur and which can also be substituted by one or more identical or different substituents from the group consisting of $(C_1$–$C_4)$-alkyl and oxo;

$R^{21}$ is hydrogen, $(C_1$–$C_8)$-alkyl, $(C_3$–$C_{12})$-cycloalkyl, $(C_3$–$C_{12})$-cycloalkyl-$(C_1$–$C_8)$-alkyl, $(C_6$–$C_{14})$-aryl, $(C_6$–$C_{14})$-aryl-$(C_1$–$C_8)$-alkyl, the radical Hct- or Hct-$(C_1$–$C_8)$-alkyl, where alkyl radicals can be monosubstituted or polysubstituted by fluorine and the radicals $R^{21}$ can be identical or different if they occur several times;

$R^{22}$ is $(C_3$–$C_{12})$-cycloalkyl, $(C_3$–$C_{12})$-cycloalkyl-$(C_1$–$C_8)$-alkyl, $(C_6$–$C_{14})$-aryl the radical Het- or Het-$(C_1$–$C_8)$-alkyl, where alkyl radicals can be monosubstituted or polysubstituted by fluorine;

$R^{23}$ is $(C_1$–$C_8)$-alkyl, $(C_3$–$C_{12})$-cycloalkyl, $(C_3$–$C_{12})$-cycloalkyl-$(C_1$–$C_8)$-alkyl, $(C_6$–$C_{14})$-aryl, $(C_6$–$C_{14})$-aryl-$(C_1$–$C_8)$-alkyl, the radical Het- or Het-$(C_1$–$C_8)$-alkyl, where alkyl radicals can be monosubstituted or polysubstituted by fluorine;

$R^{24}$ $(C_3$–$C_{12})$-cycloalkyl, $(C_3$–$C_{12})$-cycloalkyl-$(C_1$–$C_8)$-alkyl, $(C_6$–$C_{14})$-aryl, $(C_6$–$C_{14})$-aryl-$(C_1$–$C_8)$-alkyl, the radical Het- or Het-$(C_1$–$C_8)$-alkyl, where alkyl radicals can be monosubstituted or polysubstituted by fluorine;

$R^{25}$ has the meanings of $R^{23}$, where the radicals $R^{25}$ can be identical or different;

$R^{26}$ has the meanings of $R^{21}$ or HO—$((C_1$–$C_8)$-alkyl), where alkyl radicals can be monosubstituted or polysubstituted by fluorine;

$R^{27}$ is hydrogen, $(C_3$–$C_{12})$-cycloalkyl, $(C_3$–$C_{12})$-cycloalkyl-$(C_1$–$C_8)$-alkyl, $(C_6$–$C_{14})$-aryl-$(C_1$–$C_8)$-alkyl, the radical Het- or Het-$(C_1$–$C_8)$-alkyl, where alkyl radicals can be monosubstituted or polysubstituted by fluorine;

$R^{28}$ is one of the radicals $R^{21}$—, $R^{21}$O, $R^{26}$N($R^{26}$)—, $R^{12}$C(O)—, $R^{21}$O—C(O)—, (($C_1$–$C_{18}$)-alkyl-O—C(O)—(($C_1$–$C_6$)-alkyl)-O—C(O)—, $R^{21}$N($R^{21}$)—C(O)—, $R^{21}$N($R^{21}$)—C(—N($R^{21}$))— or $R^{21}$C(O)—N($R^{21}$)—;

Het is a mono- or polycyclic, 4- to 14-membered, aromatic or nonaromatic ring which contains 1, 2, 3 or 4 identical or different heteroatoms from the group consisting of N, O and S as ring members and can optionally be substituted by one or more, identical or different substituents;

b, c, d and f independently of one another are 0 or 1, but cannot all simultaneously be 0;

e, g and h independently of one another are 0, 1, 2, 3, 4, 5 or 6;

in all their stereoisomeric forms and mixtures thereof in any ratio, and/or of their physiologically tolerable salts together with one or more physiologically tolerable carriers and/or additives.

15. A method for the treatment of asthma or allergies comprising administering to a subject in need thereof a preparation comprising a VLA-4-antagonizing-effective amount of one or more compounds of the formula I

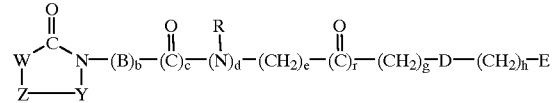

in which

W is $R^1$—A—C($R^{13}$) or $R^1$—A—CH—C;

Y is a carbonyl;

Z is N($R^0$);

A is a bivalent radical from the group consisting of $(C_1$–$C_6)$-alkylene, $(C_3$–$C_{12})$-cycloalkylene, $(C_1$–$C_6)$-alkylene-$(C_3$–$C_{12})$-cycloalkyl, phenylene, phenylene-$(C_1$–$C_6)$-alkyl, $(C_1$–$C_6)$-alkylenephenyl, $(C_1$–$C_6)$-alkylenephenyl-$(C_1$–$C_6)$-alkyl, phenylene-$(C_2$–$C_6)$-alkenyl or a bivalent radical of a 5- or 6-membered saturated or unsaturated ring which can contain 1 or 2 nitrogen atoms and can be mono- or disubstituted by $(C_1$–$C_6)$-alkyl or doubly bonded oxygen or sulfur;

B is a bivalent radical from the group consisting of $(C_1$–$C_6)$-alkylene, $(C_2$–$C_6)$-alkenylene, phenylene, phenylene-$(C_1$–$C_3)$-alkyl, $(C_1$–$C_3)$-alkylenephenyl, where the bivalent $(C_1$–$C_6)$-alkylene radical can be unsubstituted or substituted by a radical from the group consisting of $(C_1$–$C_8)$-alkyl, $(C_2$–$C_8)$-alkenyl, $(C_2$–$C_8)$-alkynyl, $(C_3$–$C_{10})$-cycloalkyl, $(C_3$–$C_{10})$-cycloalkyl-$(C_1$–$C_6)$-alkyl, optionally substituted $(C_6$–$C_{14})$-aryl, $(C_6$–$C_{14})$-aryl-$(C_1$–$C_6)$-alkyl optionally substituted in the aryl radical, optionally substituted heteroaryl and heteroaryl-$(C_1$–$C_6)$-alkyl optionally substituted in the heteroaryl radical;

D is C($R^2$)($R^3$), N($R^3$) or CH|C($R^3$);

E is tetrazolyl, ($R^8$O)$_2$P(O), HOS(O)$_2$, $R^0$NHS(O)$_2$ or $R^{10}$CO;

R is hydrogen, $(C_1$–$C_8)$-alkyl, $(C_3$–$C_{13})$-cycloalkyl, $(C_3$–$C_{12})$-cycloalkyl-$(C_1$–$C_8)$-alkyl, optionally substituted $(C_6$–$C_{14})$-aryl, $(C_6$–$C_{14})$-aryl-$(C_1$–$C_8)$-alkyl optionally substituted in the aryl radical, optionally substituted heteroaryl or heteroaryl-$(C_1$–$C_8)$-alkyl optionally substituted in the heteroaryl radical, where alkyl radicals can be mono- or polysubstituted by fluorine;

$R^0$ is hydrogen, $(C_1$–$C_8)$-alkyl, $(C_3$–$C_{12})$-cycloalkyl, $(C_3$–$C_{12})$-cycloalkyl-$(C_1$–$C_8)$-alkyl, $(C_6$–$C_{12})$-bicycloalkyl, $(C_6$–$C_{12})$-bicycloalkyl-$(C_1$–$C_8)$-alkyl, $(C_6$–$C_{12})$-tricycloalkyl, $(C_6$–$C_{12})$-tricycloalkyl-$(C_1$–$C_8)$-alkyl, optionally substituted $(C_6$–$C_{14})$-aryl, $(C_6$–$C_{14})$-aryl-$(C_1$–$C_8)$-alkyl optionally substituted in the aryl radical, optionally substituted heteroaryl, heteroaryl-$(C_1$–$C_8)$-alkyl optionally substituted in the heteroaryl radical. CHO. $(C_1$–$C_8)$-alkyl-CO, $(C_3$–$C_{12})$-cycloalkyl-CO, $(C_3$–$C_{12})$-cycloalkyl-$(C_1$–$C_8)$-alkyl-CO, $(C_6$–$C_{12})$-bicycloalkyl-CO, $(C_6$–$C_{12})$-bicycloalkyl-$(C_1$–$C_8)$-alkyl-CO, $(C_6$–$C_{12})$-tricycloalkyl-CO, $(C_6$–$C_{12})$-tricycloalkyl-$(C_1$–$C_8)$-alkyl-CO, optionally substituted $(C_6$–$C_{14})$-aryl-CO, $(C_6$–$C_{14})$-aryl-$(C_1$–$C_8)$-alkyl-CO optionally substituted in the aryl radical, optionally substituted heteroaryl CO, heteroaryl-$(C_1$–$C_8)$-alkyl-CO optionally substituted in the heteroaryl radical, $(C_1$–$C_8)$-alkyl-S(O)$_n$, $(C_3$–$C_{12})$-cycloalkyl-S(O)$_n$, $(C_3$–$C_{12})$-cycloalkyl-$(C_1$–$C_8)$-alkyl-S(O)$_n$, $(C_6$–$C_{12})$-bicycloalkyl-S(O)$_n$, $(C_6$–$C_{12})$-bicycloalkyl-$(C_1$–$C_8)$-alkyl-S(O)$_n$, $(C_6$–$C_{12})$- tricycloalkyl-S(O)$_n$, $(C_6-C_{12})$-tricycloalkyl-$(C_1-C_8)$-alkyl-S(O)$_n$, optionally substituted $(C_6-C_{14})$-aryl-S(O)$_n$, $(C_6-C_{14})$-aryl-$(C_1-C_8)$-alkyl-S(O)$_n$ optionally substituted in the aryl radical, optionally substituted heteroaryl-S(O)$_n$ or heteroaryl-$(C_1-C_8)$-alkyl-S(O)$_n$ optionally substituted in the heteroaryl radical, where n is 1 or 2;

$R^1$ is hydrogen, $(C_1-C_{10})$-alkyl, which can optionally be mono substituted or polysubstituted by fluorine, $(C_3-C_{12})$-cycloalkyl, $(C_3-C_{12})$-cycloalkyl-$(C_1-C_8)$-alkyl, optionally substituted $R^{21}$—$((C_6-C_{14})$-aryl), $(R^{21}$—$((C_0-C_{14})$-aryl))-$(C_1-C_8)$-alkyl optionally substituted in the aryl radical, the radical Het-, Het-$(C_1-C_8)$-alkyl or one of the radicals $R^{21}$O—, $R^{22}$O—NH—, $R^{21}$O—N($R^{23}$)—, $R^{24}$NH—, $R^{25}$N($R^{25}$)—, HO—$((C_1-C_8)$-alkyl)-N($R^{26}$)—, $R^{27}$C(O)—NH—, $R^{21}$C(O)—N($R^{23}$), $R^{21}$C(O)—, $R^{21}$O—C(O)—, $R^{28}$N($R^{21}$)—C(O)—, $R^{21}$O—N=, O= and S=;

$R^2$ is hydrogen, $(C_1-C_8)$-alkyl, optionally substituted $(C_6-C_{14})$-aryl, $(C_6-C_{14})$-aryl-$(C_1-C_8)$-alkyl optionally substituted in the aryl radical or $(C_3-C_8)$-cycloalkyl;

$R^3$ is hydrogen, $(C_1-C_8)$-alkyl, optionally substituted $(C_0-C_{14})$-aryl, $(C_6-C_{14})$-aryl-$(C_1-C_8)$-alkyl optionally substituted in the aryl radical, $(C_3-C_8)$-cycloalkyl, $(C_2-C_8)$-alkenyl, $(C_2-C_8)$-alkynyl, $(C_2-C_8)$-alkenylcarbonyl, $(C_2-C_8)$-alkynylcarbonyl, pyridyl, $R^{11}$NH, $R^4$CO, COOR$^4$, CON(CH$_3$)R$^4$, CONHR$^4$, CSNHR$^4$, COOR$^{15}$, CON(CH$_3$)R$^{15}$ or CONHR$^{15}$;

$R^4$ is hydrogen or $(C_1-C_{18})$-alkyl which can optionally be mono- or polysubstituted by identical or different radicals from the group consisting of hydroxyl, hydroxycarbonyl, aminocarbonyl, mono or di-$((C_1-C_{18})$-alkyl)-aminocarbonyl, amino-$(C_2-C_{18})$-alkylaminocarbonyl, amino-$(C_1-C_3)$-alkylphenyl-$(C_1-C_3)$-alkylaminocarbonyl, $(C_1-C_{18})$-alkylcarbonylamino-$(C_1-C_3)$-alkylphenyl-$(C_1-C_3)$-alkylaminocarbonyl, $(C_1-C_{18})$-alkylcarbonylamino-$(C_2-C_{18})$-alkylaminocarbonyl, $(C_6-C_{14})$-aryl $(C_1-C_8)$-alkoxycarbonyl which can also be substituted in the aryl radical, amino, mercapto, $(C_1-C_{18})$-alkoxy, $(C_1-C_{18})$-alkoxycarbonyl, optionally substituted $(C_3-C_8)$-cycloalkyl, HOS(O)$_2$-$(C_1-C_3)$-alkyl, $R^9$NHS(O)$_2$—$(C_1-C_3)$-alkyl, $(R^8$O)$_2$P(O)—$(C_1-C_3)$-alkyl, tetrazolyl-$(C_1-C_3)$-alkyl, halogen, nitro, trifluoromethyl or the radical $R^5$;

$R^5$ is optionally substituted $(C_6-C_{14})$-aryl, $(C_6-C_{14})$-aryl-$(C_1-C_8)$-alkyl optionally substituted in the aryl radical, a mono- or bicyclic 5- to 12-membered heterocyclic ring which can be aromatic, partially hydrogenated or completely hydrogenated and which can contain one, two or three identical or different heteroatoms from the group consisting of nitrogen, oxygen and sulfur, a radical $R^6$ or a radical $R^6$CO—, where the aryl radical and, independently thereof, the heterocyclic radical can be mono- or polysubstituted by identical or different radicals from the group consisting of $(C_1-C_{18})$-alkyl, $(C_1-C_{18})$-alkoxy, halogen, nitro, amino and trifluoromethyl;

$R^6$ is $R^7R^8$N, $R^7$O or $R^7$S or an amino acid side chain, a natural unnatural amino acid, imino acid, optionally N—$(C_1-C_8)$-alkylated or N—$((C_6-C_{14})$-aryl-$(C_1-C_8)$-alkylated) azaamino acid or a dipeptide radical which can also be substituted in the aryl radical and/or reduced in the peptide bond to —NH—CH$_2$—, and their esters and amides, where hydrogen or hydroxymethyl can optionally stand in place of free functional groups and/or where free functional groups can be protected by protective groups customary in peptide chemistry;

$R^7$ is hydrogen, $(C_1-C_{18})$-alkyl, $(C_6-C_{14})$-aryl-$(C_1-C_8)$-alkyl, $(C_1-C_{10})$-alkylcarbonyl, $(C_1-C_{18})$-alkoxycarbonyl, $(C_6-C_{14})$-arylcarbonyl, $(C_6-C_{14})$-aryl $(C_1-C_8)$-alkylcarbonyl or $(C_6-C_{14})$-aryl-$(C_1-C_{18})$-alkyloxycarbonyl, where the alkyl groups can optionally be substituted by an amino group and/or where the aryl radicals can be mono- or polysubstituted by identical or different radicals from the group consisting of $(C_1-C_8)$-alkyl, $(C_1-C_8)$-alkoxy, halogen, nitro, amino and trifluoromethyl, or is a natural or unnatural amino acid, imino acid, optionally N—$(C_1-C_8)$-alkylated or N—$((C_6-C_{14})$-aryl-$(C_1-C_8)$ alkylated) azaamino acid or a dipeptide radical which can also be substituted in the aryl radical and/or reduced in the peptide bond to —NH—CH$_4$—;

$R^8$ is hydrogen, $(C_1-C_{18})$-alkyl, optionally substituted $(C_6-C_{14})$-aryl or $(C_6-C_{14})$-aryl-$(C_1-C_8)$-alkyl which can also be substituted in the aryl radical;

$R^9$ is hydrogen, aminocarbonyl, $(C_1-C_{18})$ alkylaminocarbonyl, $(C_3-C_8)$-cycloalkylaminocarbonyl, optionally substituted $(C_6-C_{14})$-arylaminocarbonyl, $(C_1-C_{18})$-alkyl, optionally substituted $(C_6-C_{14})$-aryl or $(C_3-C_8)$-cycloalkyl;

$R^{10}$ is hydroxyl, $(C_1-C_{18})$-alkoxy, $(C_6-C_{14})$-aryl-$(C_1-C_8)$-alkoxy which can also be substituted in the aryl radical, optionally substituted $(C_6-C_{14})$-aryloxy, amino or mono- or di-$((C_1-C_{18})$-alkyl)amino;

$R^{11}$ is hydrogen, $(C_1-C_{18})$-alkyl, $R^{12}$CO, $R^{12a}$CS, optionally substituted $(C_6-C_{14})$-aryl-S(O)$_2$, $(C_1-C_{18})$-alkyl-S(O)$_2$, $(C_6-C_{14})$-aryl-$(C_1-C_8)$-alkyl optionally substituted in the aryl radical, $R^9$NHS(O)$_2$ or the radical $R^{15}$;

$R^{12}$ is hydrogen, $(C_1-C_{18})$-alkyl, $(C_2-C_8)$-alkenyl, $(C_2-C_8)$-alkynyl, optionally substituted $(C_6-C_{14})$-aryl, $(C_1-C_{18})$-alkoxy, $(C_6-C_{14})$-aryl-$(C_1-C_8)$-alkoxy which can also be substituted in the aryl radical, optionally substituted $(C_6-C_{14})$-aryloxy, the radical $R^{15}$, the radical R —O—, amino, mono- or di-$((C_1-C_{18})$-alkyl) amino, $(C_2-C_8)$-alkenylamino, $(C_2-C_8)$-alkynylamino, $(C_3-C_{12})$-cycloalkylamino, $(C_3-C_{12})$-cycloalkyl-$(C_1-C_8)$-alkylamino, the radical $R^{15}$—NH—, optionally substituted $(C_6-C_{14})$-aryl-NH, $(C_6-C_{14})$-aryl-$(C_1-C_8)$-alkyl-NH, which can also be substituted in the aryl radical, optionally substituted heteroaryl-NH or heteroaryl-$(C_1-C_8)$-aryl-NH optionally substituted in the heteroaryl radical;

$R^{12a}$ is amino, mono- or di-$((C_1-C_{18})$-alkyl)-amino, $(C_2-C_8)$-alkenylamino, $(C_2-C_8)$-alkynylamino, $(C_3-C_{12})$-cycloalkylamino, $(C_3-C_{12})$-cycloalkyl-$(C_1-C_8)$-alkylamino, the radical $R^{15}$—NH—, optionally substituted $(C_6-C_{14})$-aryl-NH, $(C_6-C_{14})$-aryl-$(C_1-C_8)$-alkyl-NH, which can also be substituted in the aryl radical, optionally substituted heteroaryl-NH or heteroaryl-$(C_1-C_8)$-alkyl-NH optionally substituted in the heteroaryl radical;

$R^{13}$ is hydrogen, $(C_1-C_6)$-alkyl, $(C_6-C_{14})$-aryl-$(C_1-C_8)$-alkyl optionally substituted in the aryl radical or $(C_3-C_8)$-cycloalkyl;

$R^{15}$ is $R^{16}$-$(C_1-C_6)$-alkyl or $R^{16}$;

$R^{16}$ is a 6- to 24-membered bicyclic or tricyclic radical which is saturated or partially unsaturated and which can also contain one to four identical or different heteroatoms from the group consisting of nitrogen, oxygen and sulfur and which can also be substituted by one or more identical or different substituents from the group consisting of $(C_1-C_4)$-alkyl and oxo;

$R^{21}$ is hydrogen, $(C_1-C_8)$-alkyl, $(C_3-C_{12})$-cycloalkyl, $(C_3-C_{12})$-cycloalkyl-$(C_1-C_8)$-alkyl, $(C_6-C_{14})$-aryl, $(C_6-C_{14})$-aryl-$(C_1-C_8)$-alkyl, the radical Het- or Het-$(C_1-C_8)$-alkyl, where alkyl radicals can be monosubstituted or polysubstituted by fluorine and the radicals $R^{21}$ can be identical or different if they occur several times;

$R^{22}$ is $(C_3-C_{12})$-cycloalkyl, $(C_3-C_{12})$-cycloalkyl-$(C_1-C_8)$-alkyl, $(C_6-C_{14})$-aryl, the radical Het- or Het-$(C_1-C_8)$-alkyl, where alkyl radicals can be monosubstituted or polysubstituted by fluorine;

$R^{23}$ is $(C_1-C_8)$-alkyl, $(C_3-C_{12})$-cycloalkyl, $(C_3-C_{12})$-cycloalkyl-$(C_1-C_8)$-alkyl, $(C_6-C_{14})$-aryl, $(C_6-C_{14})$-aryl-$(C_1-C_8)$-alkyl, the radical Het- or Het-$(C_1-C_8)$-alkyl, where alkyl radicals can be monosubstituted or polysubstituted by fluorine;

$R^{24}$ $(C_3-C_{12})$-cycloalkyl, $(C_3-C_{12})$-cycloalkyl-$(C_1-C_8)$-alkyl, $(C_6-C_{14})$-aryl, $(C_6-C_{14})$-aryl-$(C_1-C_8)$-alkyl, the radical Het- or Het-$(C_1-C_8)$-alkyl, where alkyl radicals can be monosubstituted or polysubstituted by fluorine;

$R^{25}$ has the meanings of $R^{23}$, where the radicals $R^{25}$ can be identical or different;

$R^{26}$ has the meanings of $R^{21}$ or HO—$((C_1-C_8)$-alkyl), where alkyl radicals can be monosubstituted or polysubstituted by fluorine;

$R^{27}$ is hydrogen, $(C_3-C_{12})$-cycloalkyl, $(C_{13}-C_{12})$-cycloalkyl-$(C_1-C_8)$-alkyl, $(C_6-C_{14})$-aryl-$(C_1-C_8)$-alkyl, the radical Het- or Het-$(C_1-C_8)$-alkyl, where alkyl radicals can be monosubstituted or polysubstituted by fluorine;

$R^{28}$ is one of the radicals $R^{21}$—, $R^{21}O$—, $R^{26}N(R^{26})$—, $R^{21}C(O)$—, $R^{12}O$—$C(O)$—, $((C_1-c_{18})$-alkyl-O—C(O)—$((C_1-C_6)$-alkyl)-O—C(O)—, $R^{21}N(R^{21})$—C(O)—, $R^{21}N(R^{21})$—C(=N(R^{21}))$— or $R^{21}C(O)$—N(R^{21})$—;

Het is a mono- or polycyclic, 4 to 14-membered, aromatic or nonaromatic ring which contains 1, 2, 3 or 4 identical or different heteroatoms from the group consisting of N, O and S as ring members and can optionally be substituted by one or more, identical or different substituents;

b, c, d and f independently of one another are 0 or 1, but cannot all simultaneously be 0;

e, g and h independently of one another are 0, 1, 2, 3, 4, 5 or 6; in all their stereoisomeric forms and mixtures thereof in any ratio, and/or of their physiologically tolerable salts together with one or more physiologically tolerable carriers and/or additives.

16. A method for treating restenoses or diabetes, or for the therapy of malaria comprising administering to a subject in need thereof a preparation comprising a VLA-4-antagonizing-effective amount of one or more compounds of the formula I

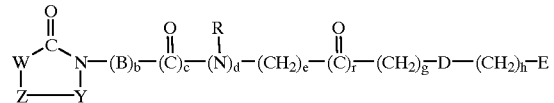

(I)

in which

W is $R^1$—A—$C(R^{13})$ or $R^1$—A—CH—C;

Y is a carbonyl;

Z is $N(R^0)$;

A is a bivalent radical from the group consisting of $(C_1-C_6)$-alkylene, $(C_3-C_{12})$-cycloalkylene, $(C_1-C_6)$-alkylene-$(C_3-C_{12})$-cycloalkyl, phenylene, phenylene-$(C_1-C_6)$-alkyl, $(C_1-C_6)$-alkylenephenyl, $(C_1-C_6)$-alkylenephenyl-$(C_1-C_6)$-alkyl, phenylene-$(C_2-C_6)$-alkenyl or a bivalent radical of a 5- or 6-membered saturated or unsaturated ring which can contain 1 or 2 nitrogen atoms and can be mono- or disubstituted by $(C_1-C_6)$-alkyl or doubly bonded oxygen or sulfur;

B is a bivalent radical from the group consisting of $(C_1-C_6)$-alkylene, $(C_2-C_6)$-alkenylene, phenylene, phenylene-$(C_1-C_3)$-alkyl, $(C_1-C_3)$-alkylenephenyl, where the bivalent $(C_1-C_6)$-alkylene radical can be unsubstituted or substituted by a radical from the group consisting of $(C_1-C_8)$-alkyl, $(C_2-C_8)$-alkenyl, $(C_2-C_8)$-alkynyl, $(C_3-C_{10})$-cycloalkyl, $(C_3-C_{10})$-cycloalkyl-$(C_1-C_6)$-alkyl, optionally substituted $(C_6-C_{14})$-aryl, $(C_6-C_{14})$-aryl-$(C_1-C_6)$-alkyl optionally substituted in the aryl radical, optionally substituted heteroaryl and heteroaryl-$(C_1-C_6)$-alkyl optionally substituted in the heteroaryl radical;

D is $C(R^2)(R^3)$, $N(R^3)$ or $CH=C(R^3)$;

E is tetrazolyl, $(R^8O)_2P(O)$, $HOS(O)_2$, $R^0NHS(O)_2$ or $R^{10}CO$;

R is hydrogen, $(C_1-C_8)$-alkyl, $(C_3-C_{12})$-cycloalkyl, $(C_3-C_{12})$-cycloalkyl-$(C_1-C_8)$-alkyl, optionally substituted $(C_6-C_{14})$-aryl, $(C_6-C_{14})$-aryl-$(C_1-C_8)$-alkyl optionally substituted in the aryl radical, optionally substituted heteroaryl or heteroaryl-$(C_1-C_8)$-alkyl optionally substituted in the heteroaryl radical, where alkyl radicals can be mono- or polysubstituted by fluorine;

$R^0$ is hydrogen, $(C_1-C_8)$-alkyl, $(C_3-C_{12})$-cycloalkyl, $(C_3-C_{12})$-cycloalkyl-$(C_1-C_8)$-alkyl, $(C_6-C_{12})$-bicycloalkyl, $(C_6-C_{12})$-bicycloalkyl-$(C_1-C_8)$-alkyl, $(C_6-C_{12})$-tricycloalkyl, $(C_6-C_{12})$-tricycloalkyl-$(C_1-C_8)$-alkyl, optionally substituted $(C_6-C_{14})$-aryl, $(C_6-C_{14})$-aryl-$(C_1-C_8)$ alkyl optionally substituted in the aryl radical, optionally substituted heteroaryl, heteroaryl-$(C_1-c_8)$-alkyl optionally substituted in the heteroaryl radical, CHO, $(C_1-C_8)$-alkyl-CO, $(C_3-C_{12})$-cycloalkyl-CO, $(C_3-c_{12})$ cycloalkyl-$(C_1-C_8)$-alkyl-CO, $(C_6-C_{13})$-bicycloalkyl-CO, $(C_6-C_{12})$-bicycloalkyl-$(C_1-C_8)$-alkyl-CO, $(C_6-C_{12})$-tricycloalkyl-CO, $(C_6-C_{12})$-tricycloalkyl $(C_1-C_8)$-alkyl-CO, optionally substituted $(C_6-C_{14})$-aryl-CO, $(C_6-C_{14})$-aryl-$(C_1-C_8)$-alkyl-CO optionally substituted in the aryl radical, optionally substituted heteroaryl-CO, heteroaryl-$(C_1-C_8)$-alkyl-CO optionally substituted in the heteroaryl radical, $(C_1-C_8)$-alkyl-$S(O)_n$, $(C_3-C_{12})$-cycloalkyl-$S(O)_n$, $(C_3-C_{12})$-cycloalkyl-$(C_1-C_8)$-alkyl-$S(O)_n$, $(C_6-C_{12}$- bicycloalkyl-S(O)$_n$, (C$_6$–C$_{12}$)-bicycloalkyl-(C$_1$–C$_8$)-alkyl-S(O)$_n$, (C$_6$–C$_{12}$)-tricycloalkyl-S(O)$_n$, (C$_6$–C$_{12}$)-tricycloalkyl-(C$_1$–C$_8$)-alkyl-S(O)$_n$, optionally substituted (C$_6$–C$_{14}$)-aryl-S(O)$_n$, (C$_6$–C$_{14}$)-aryl-(C$_1$–C$_8$)-alkyl-S(O)$_n$ optionally substituted in the aryl radical, optionally substituted heteroaryl-S(O)$_n$ or heteroaryl-(C$_1$–C$_8$)-alkyl-S(O)$_n$ optionally substituted in the heteroaryl radical, where n is 1 or 2;

R$^1$ is hydrogen, (C$_1$–C$_{10}$)-alkyl, which can optionally be mono substituted or polysubstituted by fluorine, (C$_3$–C$_{12}$)-cycloalkyl, (C$_3$–C$_{12}$)-cycloalkyl-(C$_1$–C$_8$)-alkyl, optionally substituted R$^{21}$—((C$_6$–C$_{14}$)-aryl), (R$^{21}$—((C$_6$–C$_{14}$)-aryl))—(C$_1$–C$_8$)-alkyl optionally substituted in the aryl radical, the radical Het-, Het-(C$_1$–C$_8$) alkyl or one of the radicals R$^{21}$O—, R$^{22}$O—NH—, R$^{21}$O—N(R$^{25}$)—, R$^{24}$NH—, R$^{25}$N(R$^{25}$)—, HO—((C$_1$–C$_8$)-alkyl)—N(R$^{26}$)—, R$^{27}$C(O)—NH—, R$^{21}$C(O)—N(R$^{23}$), R$^{21}$C(O)—, R$^{21}$O—C(O)—, R$^{28}$N(R$^{21}$)—C(O)—, R$^{21}$O—N=, O| and S—;

R$^2$ is hydrogen, (C$_1$–C$_8$)-alkyl, optionally substituted (C$_6$–C$_{14}$)-aryl, (C$_6$–C$_{14}$)-aryl-(C$_1$–C$_8$)-alkyl optionally substituted in the aryl radical or (C$_3$–C$_8$) cycloalkyl;

R$^3$ is hydrogen, (C$_1$–C$_8$)-alkyl, optionally substituted (C$_6$–C$_{14}$)-aryl, (C$_6$–C$_{14}$)-aryl-(C$_1$–C$_8$)-alkyl optionally substituted in the aryl radical, (C$_3$–C$_8$)-cycloalkyl, (C$_2$–C$_8$)-alkenyl, (C$_2$–C$_8$)-alkynyl, (C$_2$–C$_8$)-alkenylcarbonyl, (C$_2$–C$_8$)-alkynylcarbonyl, pyridyl, R$^{11}$NH, R$^d$CO, COOR$^4$, CON(CH$_3$)R$^4$, CONHR$^4$, CSNHR$^4$, COOR$^{15}$, CON(CH$_3$)R$^{15}$ or CONHR$^{15}$;

R$^4$ is hydrogen or (C$_1$–C$_{28}$)-alkyl which can optionally be mono- or polysubstituted by identical or different radicals from the group consisting of hydroxyl, hydroxycarbonyl, aminocarbonyl, mono- or di-((C$_1$–C$_{18}$)-alkyl)-aminocarbonyl, amino-(C$_2$–C$_{18}$)-alkylaminocarbonyl, amino-(C$_1$–C$_3$)-alkylphenyl-(C$_1$–C$_3$)-alkylaminocarbonyl, (C$_1$–C$_{18}$)-alkylcarbonylamino-(C$_1$–C$_3$)-alkylphenyl-(C$_1$–C$_3$)-alkylaminocarbonyl, (C$_1$–C$_{18}$)-alkylcarbonylamino-(C$_3$–C$_{18}$)-alkylaminocarbonyl, (C$_6$–C$_{14}$)-aryl-(C$_1$–C$_8$)-alkoxycarbonyl which can also be substituted in the aryl radical, amino, mercapto, (C$_1$–C$_{18}$)-alkoxy, (C$_1$–C$_{18}$)-alkoxycarbonyl, optionally substituted (C$_3$–C$_8$)-cycloalkyl, HOS(O)$_2$— (C$_1$–C$_3$)-alkyl, R$^9$NHS(O)$_2$—(C$_1$–C$_3$)-alkyl, (R$^8$O)$_2$P(O)—(C$_1$–C$_3$)-alkyl, tetrazolyl-(C$_1$–C$_3$)-alkyl, halogen, nitro, trifluoromethyl or the radical R$^5$;

R$^5$ is optionally substituted (C$_6$–C$_{14}$)-aryl, (C$_6$–C$_{14}$)-aryl-(C$_1$–C$_8$)-alkyl optionally substituted in the aryl radical, a mono- a bicyclic 5- to 12-membered heterocyclic ring which can be aromatic, partially hydrogenated or completely hydrogenated and which can contain one, two or three identical or different heteroatoms from the group consisting of nitrogen, oxygen and sulfur, a radical R$^6$ or a radical R$^6$CO—, where the aryl radical and, independently thereof, the heterocyclic radical can be mono- or polysubstituted by identical or different radicals from the group consisting of (C$_1$–C$_{18}$)-alkyl, (C$_1$–C$_{18}$)-alkoxy, halogen, nitro, amino and trifluoromethyl;

R$^6$ is R$^7$R$^8$N, R$^7$O or R$^7$S or an amino acid side chain, a natural or unnatural amino acid, imino acid, optionally N—(C$_1$–C$_8$)-alkylated or N—((C$_6$–C$_{14}$) aryl (C$_1$–C$_8$)-alkylated) azaamino acid or a dipeptide radical which can also be substituted in the aryl radical and/or reduced in the peptide bond to —NH—CH$_2$—, and their esters and amides, where hydrogen or hydroxymethyl can optionally stand in place of free functional groups and/or where free functional groups can be protected by protective groups customary in peptide chemistry;

R$^7$ is hydrogen, (C$_1$–C$_{18}$)-alkyl, (C$_6$–C$_{14}$)-aryl-(C$_1$–C$_8$)-alkyl, (C$_1$–C$_{18}$)-alkylcarbonyl, (C$_1$–C$_{18}$)-alkoxycarbonyl, (C$_6$–C$_{14}$)-arylcarbonyl, (C$_6$–C$_{14}$)-aryl-(C$_1$–C$_8$)-alkylcarbonyl or (C$_6$–C$_{14}$)-aryl-(C$_1$–C$_{18}$)-alkyloxycarbonyl, where the alkyl groups can optionally be substituted by an amino group and/or where the aryl radicals can be mono- or polysubstituted by identical or different radicals from the group consisting of (C$_1$–C$_8$)-alkyl, (C$_1$–C$_8$)-alkoxy, halogen, nitro, amino and trifluoromethyl, or is a natural or unnatural amino acid, imino acid, optionally N—(C$_1$–C$_8$)-alkylated or N—((C$_6$–C$_{14}$)-aryl-(C$_1$–C$_8$)-alkylated) azaamino acid or a dipeptide radical which can also be substituted in the aryl radical and/or reduced in the peptide bond to —NH—CH$_2$—;

R$^8$ is hydrogen, (C$_1$–C$_{18}$)-alkyl, optionally substituted (C$_6$–C$_{14}$)-aryl or (C$_6$–C$_{14}$)-aryl-(C$_1$–C$_8$)-alkyl which can also be substituted in the aryl radical;

R$^9$ is hydrogen, aminocarbonyl, (C$_1$–C$_{18}$)-alkylaminocarbonyl, (C$_3$–C$_8$)-cycloalkylaminocarbonyl, optionally substituted (C$_6$–C$_{14}$)-arylaminocarbonyl, (C$_1$–C$_{18}$)-alkyl, optionally substituted (C$_6$–C$_{14}$)-aryl or (C$_3$–C$_8$)-cycloalkyl;

R$^{10}$ is hydroxyl, (C$_1$–C$_{18}$)-alkoxy, (C$_6$–C$_{14}$)-aryl-(C$_1$–C$_8$)-alkoxy which can also be substituted in the aryl radical, optionally substituted (C$_6$–C$_{14}$)-aryloxy, amino or mono- or di-((C$_1$–C$_{18}$)-alkyl)amino;

R$^{11}$ is hydrogen, (C$_1$–C$_{18}$)-alkyl, R$^{12}$CO, R$^{12a}$CS, optionally substituted (C$_6$–C$_{14}$)-aryl-(S(O)$_3$, (C$_1$–C$_{18}$)-alkyl-S(O)$_2$, (C$_6$–C$_{14}$)-aryl-(C$_1$–C$_8$)-alkyl optionally substituted in the aryl radical, R$^9$NHS(O)$_2$ or the radical R$^{15}$;

R$^{12}$ is hydrogen, (C$_1$–C$_{18}$)-alkyl, (C$_2$–C$_8$)-alkenyl, (C$_2$–C$_8$)-alkynyl, optionally substituted (C$_6$–C$_{14}$)-aryl, (C$_1$–C$_{18}$)-alkoxy, (C$_6$–C$_{14}$)-aryl-(C$_1$–C$_8$)-alkoxy which can also be substituted in the aryl radical, optionally substituted (C$_6$–C$_{14}$)-aryloxy, the radical R$^{15}$, the radical R$^{15}$—O—, amino, mono- or di-((C$_1$–C$_{18}$)-alkyl)amino, (C$_2$–C$_8$)-alkenylamino, (C$_2$–C$_8$)-alkynylamino, (C$_3$–C$_{12}$)-cycloalkylamino, cycloalkylamino, (C$_3$–C$_{12}$)-cycloalkyl-(C$_1$–C$_8$)-alkylamino, the radical R$^{15}$—NH—, optionally substituted (C$_6$–C$_{14}$)-aryl-NH, (C$_6$–C$_{14}$)-aryl-(C$_1$–C$_8$)-alkyl-NH, which can also be substituted in the aryl radical, optionally substituted heteroaryl-NH or heteroaryl-(C$_1$–C$_8$)-alkyl-NH optionally substituted in the heteroaryl radical;

R$^{12a}$ is amino, mono- or di-((C$_1$–C$_{18}$)-alkyl)-amino, (C$_2$–C$_8$)-alkenylamino, (C$_2$–C$_8$)-alkynylamino, (C$_3$–C$_{12}$)-cycloalkylamino, (C$_3$–C$_{12}$)-cycloalkyl-(C$_1$–C$_8$)-alkylamino, the radical R$^{15}$—NH—, optionally substituted (C$_6$–C$_{14}$)-aryl-NH, (C$_6$–C$_{14}$)-aryl-(C$_1$–C$_8$)-alkyl-NH, which can also be substituted in the aryl radical, optionally substituted heteroaryl-NH or heteroaryl-(C$_1$–C$_8$)-alkyl-NH optionally substituted in the heteroaryl radical;

R$^{13}$ is hydrogen, (C$_1$–C$_6$)-alkyl, (C$_6$–C$_{14}$)-aryl-(C$_1$–C$_6$)-alkyl optionally substituted in the aryl radical or (C$_3$–C$_8$)-cycloalkyl;

R$^{15}$ is R$^{16}$-(C$_1$–C$_6$)-alkyl or R$^{16}$;

R$^{16}$ is a 6- to 24-membered bicyclic or tricyclic radical which is saturated or partially unsaturated and which can also contain one to four identical or different heteroatoms from the groups consisting of nitrogen, oxygen and sulfur and which can also be substituted by one or more identical or different substituents form the group consisting of $(C_1-C_4)$-alkyl and oxo;

$R^{21}$ is hydrogen, $(C_1-C_8)$-alkyl, $(C_3-C_{12})$-cycloalkyl, $(C_3-C_{12})$-cycloalkyl-$(C_1-C_8)$-alkyl, $(C_6-C_{14})$-aryl, $(C_6-C_{14})$-aryl-$(C_1-C_8)$-alkyl, the radical Het- or Het-$(C_1-C_8)$-alkyl, where alkyl radicals can be monosubstituted or polysubstituted by fluorine and the radicals $R^{21}$ can be identical or different if they occur several times;

$R^{22}$ is $(C_3-C_{12})$-cycloalkyl, $(C_3-C_{12})$-cycloalkyl-$(C_1-C_8)$-alkyl, $(C_6-C_{14})$-aryl, the radical Het- or Het-$(C_1-C_8)$-alkyl, where alkyl radicals can be monosubstituted or polysubstituted by fluorine;

$R^{23}$ is $(C_1-C_8)$-alkyl, $(C_3-C_{12})$-cycloalkyl, $(C_3-C_{12})$-cycloalkyl-$(C_1-C_8)$-alkyl, $(C_6-C_{14})$-aryl, $(C_6-C_{14})$-aryl-$(C_1-C_8)$-alkyl, the radical Het- or Het-$(C_1-C_8)$-alkyl, where alkyl radicals can be monosubstituted or polysubstituted by fluorine;

$R^{24}$ $(C_3-C_{12})$-cycloalkyl, $(C_3-C_{12})$-cycloalkyl-$(C_1-C_8)$-alkyl, $(C_6-C_{14})$-aryl, $(C_6-C_{14})$-aryl-$(C_1-C_8)$-alkyl, the radical Het- or Het-$(C_1-C_8)$-alkyl, where alkyl radicals can be monosubstituted or polysubstituted by fluorine;

$R^{25}$ has the meanings of $R^{23}$, where the radicals $R^{25}$ can be identical or different;

$R^{26}$ has the meanings of $R^{21}$ or HO—($(C_1-C_8)$-alkyl), where alkyl radicals can be monosubstituted or polysubstituted by fluorine;

$R^{27}$ is hydrogen, $(C_3-C_{12})$-cycloalkyl, $(C_3-C_{12})$-cycloalkyl-$(C_1-C_8)$-alkyl, $(C_6-C_{14})$-aryl-$(C_1-C_8)$-alkyl, the radical Het- or Het-$(C_1-C_8)$-alkyl, where alkyl radicals can be monosubstituted or polysubstituted by fluorine;

$R^{28}$ is one of the radicals $R^{21}$—, $R^{21}O$—, $R^{26}N(R^{26})$—, $R^{21}C(O)$—, $R^{21}O$—$C(O)$—, (($(C_1-C_{18})$-alkyl-O—$C(O)$—(($(C_1-C_6)$-alkyl)-O—$C(O)$—, $R^{21}N(R^{21})$—$C(O)$—, $R^{21}N(R^{21})$—$C(=N(R^{21}))$— or $R^{21}C(O)$—$N(R^{21})$—;

Het is a mono- or polycyclic, 4- to 14-membered, aromatic or nonaromatic ring which contains 1, 2, 3 or 4 identical or different heteroatoms from the group consisting of N, O and S as ring members and can optionally be substituted by one or more, identical or different substituents;

b, c, d and f independently of one another are 0 or 1, but cannot all simultaneously be 0;

e, g and h independently of one another are 0, 1, 2, 3, 4, 5 or 6;

in all their stereoisomeric forms and mixtures thereof in any ratio, and/or of their physiologically tolerable salts together with one or more physiologically tolerable carriers and/or additives.

17. A method for inhibition of the VLA-4-receptor comprising administering to a subject in need thereof a preparation comprising a VLA-4-antagonizing-effective amount of one or more compounds of the formula I

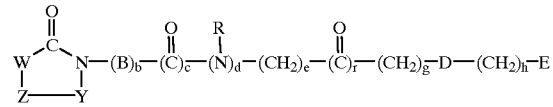

in which

W is $R^1$—A—$C(R^{13})$ or $R^1$—A—CH=C;

Y is a carbonyl;

Z is $N(R^0)$;

A is a bivalent radical from the group consisting of $(C_1-C_6)$-alkylene, $(C_3-C_{12})$-cycloalkylene, $(C_1-C_6)$-alkylene-$(C_3-C_{12})$-cycloalkyl, phenylene, phenylene-$(C_1-C_6)$-alkyl, $(C_1-C_6)$-alkylenephenyl, $(C_1-C_6)$-alkylenephenyl-$(C_1-C_6)$-alkyl, phenylene-$(C_2-C_6)$-alkenyl or a bivalent radical or a 5- or 6-membered saturated or unsaturated ring which can contain 1 or 2 nitrogen atoms and can be mono- or disubstituted by $(C_1-C_6)$-alkyl or doubly bonded oxygen or sulfur;

B is a bivalent radical from the group consisting of $(C_1-C_6)$-alkylene, $(C_2-C_6)$-alkenylene, phenylene, phenylene-$(C_1-C_3)$-alkyl, $(C_1-C_3)$-alkylenephenyl, where the bivalent $(C_1-C_6)$-alkylene radical can be unsubstituted or substituted by a radical from the group consisting of $(C_1-C_8)$-alkyl, $(C_2-C_8)$-alkenyl, $(C_2-C_8)$-alkynyl, $(C_3-C_{10})$-cycloalkyl, $(C_3-C_{10})$-cycloalkyl-$(C_1-C_6)$-alkyl, optionally substituted $(C_6-C_{14})$-aryl, $(C_6-C_{14})$-aryl-$(C_1-C_6)$-alkyl optionally substituted in the aryl radical, optionally substituted heteroaryl and heteroaryl-$(C_1-C_6)$-alkyl optionally substituted in the heteroaryl radical;

D is $C(R^2)(R^3)$, $N(R^3)$ or $CH=C(R^3)$;

E is tetrazolyl, $(R^8O)_2P(O)$, $HOS(O)_2$, $R^9NHS(O)_2$ or $R^{10}CO$;

R is hydrogen, $(C_1-C_8)$-alkyl, $(C_3-C_{12})$-cycloalkyl, $(C_3-C_{12})$-cycloalkyl-$(C_1-C_8)$-alkyl, optionally substituted $(C_6-C_{14})$-aryl, $(C_6-C_{14})$-aryl-$(C_1-C_8)$-alkyl optionally substituted in the aryl radical, optionally substituted heteroaryl or heteroaryl-$(C_1-C_8)$-alkyl optionally substituted in the heteroaryl radical, where alkyl radicals can be mono- or polysubstituted by fluorine;

$R^0$ is hydrogen; $(C_1-C_8)$-alkyl, $(C_3-C_{12})$-cycloalkyl, $(C_3-C_{12})$-cycloalkyl $(C_1-C_8)$-alkyl, $(C_6-C_{12})$-bicycloalkyl, $(C_6-C_{12})$-bicycloalkyl-$(C_1-c_8)$-alkyl, $(C_6-C_{12})$-tricycloalkyl, $(C_6-C_{12})$-tricycloalkyl-$(C_1-C_8)$-alkyl, optionally substituted $(C_6-C_{14})$-aryl, $(C_6-C_{14})$-aryl-$(C_1-C_8)$-alkyl optionally substituted in the aryl radical, optionally substituted heteroaryl, heteroaryl-$(C_1-C_8)$-alkyl optionally substituted in the heteroaryl radical, CHO, $(C_1-C_8)$-alkyl-CO, $(C_3-C_{12})$-cycloalkyl-CO, $(C_3-C_{12})$-cycloalkyl-$(C_1-C_8)$-alkyl-CO, $(C_6-C_{12})$-bicycloalkyl-CO, $(C_6-C_{12})$-bicycloalkyl-$(C_1-C_8)$-alkyl-CO, $(C_6-C_{12})$-tricycloalkyl-CO, $(C_6-C_{12})$-tricycloalkyl-$(C_1-C_8)$-alkyl-CO, optionally substituted $(C_6-C_{14})$-aryl-CO, $(C_6-C_{14})$-aryl-$(C_1-C_8)$-alkyl-CO optionally substituted in the aryl radical, optionally substituted heteroaryl-CO, heteroaryl-$(C_1-C_8)$-alkyl-CO optionally substituted in the heteroaryl radical, $(C_1-C_8)$-alkyl-$S(O)_n$, $(C_3-C_{12})$-cycloalkyl-$S(O)_n$, $(C_3-C_{12})$-cycloalkyl-$(C_1-C_8)$-alkyl-$S(O)_n$, $(C_6-C_{12})$-bicycloalkyl-$S(O)_n$, $(C_6-C_{12})$-bicycloalkyl-$(C_1-C_8)$- alkyl-S(O)$_n$, (C$_6$–C$_{12}$)-tricycloalkyl-S(O)$_n$, (C$_6$–C$_{12}$)-tricycloalkyl-(C$_1$–C$_8$)-alkyl-S(O)$_n$, optionally substituted (C$_6$–C$_{14}$)-aryl-S(O)$_n$, (C$_6$–C$_{14}$)-aryl-(C$_1$–C$_8$)-alkyl-S(O)$_n$ optionally substituted in the aryl radical, optionally substituted heteroaryl-S(O)$_n$ or heteroaryl-(C$_1$–C$_8$)-alkyl-S(O)$_n$ optionally substituted in the heteroaryl radical, where n is 1 or 2;

R$^1$ is hydrogen, (C$_1$–C$_{10}$)-alkyl, which can optionally be mono substituted or polysubstituted by fluorine, (C$_3$–C$_{12}$)-cycloalkyl, (C$_3$–C$_{12}$)-cycloalkyl-(C$_1$–C$_8$)-alkyl, optionally substituted R$^{21}$—((C$_6$–C$_{14}$)-aryl), (R$^{21}$—((C$_6$–C$_{14}$)-aryl)-(C$_1$–C$_8$)-alkyl optionally substituted in the aryl radical, the radical Het-, Het-(C$_1$–C$_8$)-alkyl or one of the radicals R$^{21}$O—, R$^{22}$O—NH—, R$^{21}$O—N(R$^{23}$)—, R$^{24}$NH—, R$^{25}$N(R$^{25}$)—, HO—((C$_1$–C$_8$)-alkyl)-N(R$^{26}$)—, R$^{27}$C(O)—NH—, R$^{21}$C(O)—N(R$^{23}$)—, R$^{21}$C(O)—, R$^{21}$O—C(O)—, R$^{28}$N(R$^{21}$)—C(O)—, R$^{21}$O—N=, O= and S=;

R$^2$ is hydrogen, (C$_1$–C$_8$)-alkyl, optionally substituted (C$_6$–C$_{14}$)-aryl, (C$_6$–C$_{14}$)-aryl-(C$_1$–C$_8$)-alkyl optionally substituted in the aryl radical or (C$_3$–C$_8$)-cycloalkyl;

R$^3$ is hydrogen, (C$_1$–C$_8$)-alkyl, optionally substituted (C$_6$–C$_{14}$)-aryl, (C$_6$–C$_{14}$)-aryl-(C$_1$–C$_8$)-alkyl optionally substituted in the aryl radical, (C$_3$–C$_8$)-cycloalkyl, (C$_2$–C$_8$)-alkenyl, (C$_2$–C$_8$)-alkynyl, (C$_2$–C$_8$)-alkenylcarbonyl, (C$_2$–C$_8$)-alkynylcarbonyl, pyridyl, R$^{11}$NH, R$^4$CO, COOR$^4$, CON(CH$_3$)R$^4$, CONHR$^4$, CSNHR$^4$, COOR$^{15}$, CON(CH$_3$)R$^{15}$ or CONHR$^{15}$;

R$^4$ is hydrogen or (C$_1$–C$_{28}$)-alkyl which can optionally be mono- or polysubstituted by identical or different radicals from the group consisting of hydroxyl, hydroxycarbonyl, aminocarbonyl, mono- or di-((C$_1$–C$_{18}$)-alkyl)-aminocarbonyl, amino-(C$_2$–C$_{18}$) alkylaminocarbonyl, amino-(C$_1$–C$_3$)-alkylphenyl-(C$_1$–C$_3$)-alkylaminocarbonyl, (C$_1$–C$_{18}$)-alkylcarbonylamino-(C$_1$–C$_3$)-alkylphenyl-(C$_1$–C$_3$)-alkylaminocarbonyl, (C$_1$–C$_{18}$)-alkylcarbonylamino-(C$_2$–C$_{18}$)-alkylaminocarbonyl, (C$_6$–C$_{14}$)-aryl-(C$_1$–C$_8$)-alkoxycarbonyl which can also be substituted in the aryl radical, amino, mercapto, (C$_1$–C$_{18}$)-alkoxy, (C$_1$–C$_{18}$)-alkoxycarbonyl, optionally substituted (C$_3$–C$_8$)-cycloalkyl, HOS(O)$_2$—(C$_1$–C$_3$)-alkyl, R$^9$NHS(O)$_2$—(C$_1$–C$_3$)-alkyl, (R$^8$O)$_2$P(O)—(C$_1$–C$_3$)-alkyl, tetrazolyl-(C$_1$–C$_3$)-alkyl, halogen, nitro, trifluoromethyl or the radical R$^5$;

R$^5$ is optionally substituted (C$_6$–C$_{14}$)-aryl, (C$_6$–C$_{14}$)-aryl-(C$_1$–C$_8$) alkyl optionally substituted in the aryl radical, mono- or bicyclic 5- to 12-membered heterocyclic ring which can be aromatic, partially hydrogenated or completely hydrogenated and which can contain one, two or three identical or different heteroatoms from the group consisting of nitrogen, oxygen and sulfur, a radical R$^0$ or a radical R$^6$CO—, where the aryl radical and, independently thereof, the heterocyclic radical can be mono- or polysubstituted by identical or different radicals from the group consisting of (C$_1$–C$_{18}$) alkyl, (C$_1$–C$_{18}$)-alkoxy, halogen, nitro, amino and trifluoromethyl;

R$^6$ is R$^7$R$^8$N, R$^7$O or R$^7$S or an amino acid side chain, a natural or unnatural amino acid, imino acid, optionally N—(C$_1$–C$_8$)-alkylated or N-13 ((C$_6$–C$_{14}$)-aryl-(C$_1$–C$_8$)-alkylated) azaamino acid or a dipeptide radical which can also be substituted in the aryl radical and/or reduced in the peptide bond to —NH—CH$_2$—, and their esters and amides, where hydrogen or hydroxymethyl can optionally stand in place of free functional groups and/or where free functional groups can be protected by protective groups customary in peptide chemistry;

R$^7$ is hydrogen, (C$_1$–C$_{18}$)-alkyl, (C$_6$–C$_{14}$)-aryl-(C$_1$–C$_8$)-alkyl, (C$_1$–C$_{18}$)-alkylcarbonyl, (C$_1$–C$_{18}$)-alkoxycarbonyl, (C$_6$–C$_{14}$)-arylcarbonyl, (C$_6$–C$_{14}$)-aryl-(C$_1$–C$_8$)-alkylcarbonyl or (C$_6$–C$_{14}$)-aryl-(C$_1$–C$_{18}$)-alkyloxycarbonyl, where the alkyl groups can optionally be substituted by an amino group and/or where the aryl radicals can be mono- or polysubstituted by identical or different radicals from the group consisting of (C$_1$–C$_8$)-alkyl, (C$_1$–C$_8$)-alkoxy, halogen, nitro, amino and trifluoromethyl, or is a natural or unnatural amino acid, imino acid, optionally N—(C$_1$–C$_8$)-alkylated or N-13 ((C$_6$–C$_{14}$)-aryl-(C$_1$–C$_8$)-alkylated) azaamino acid or a dipeptide radical which can also be substituted in the aryl radical and/or reduced in the peptide bond to —NH—CH$_2$—;

R$^8$ is hydrogen, (C$_1$–C$_{18}$)-alkyl, optionally substituted (C$_6$–C$_{14}$)-aryl or (C$_6$–C$_{14}$)-aryl-(C$_1$–C$_8$)-alkyl which can also be substituted in the aryl radical;

R$^9$ is hydrogen, aminocarbonyl, (C$_1$–C$_{18}$)-alkylaminocarbonyl, (C$_3$–C$_8$)-cycloalkylaminocarbonyl, optionally substituted (C$_6$–C$_{14}$)-arylaminocarbonyl, (C$_1$–C$_{18}$)-alkyl, optionally substituted (C$_6$–C$_{14}$)-aryl or (C$_3$–C$_8$)-cycloalkyl;

R$^{10}$ is hydroxyl, (C$_1$–C$_{18}$)-alkoxy, (C$_6$–C$_{14}$)-aryl-(C$_1$–C$_8$)-alkoxy which can also be substituted in the aryl radical, optionally substituted (C$_6$–C$_{14}$)-aryloxy, amino or mono- or di-((C$_1$–C$_{18}$)-alkyl)amino;

R$^{11}$ is hydrogen, (C$_1$–C$_{18}$)-alkyl, R$^{12}$CO, R$^{12a}$CS, optionally substituted (C$_6$–C$_{14}$)-aryl-S(O)$_2$, (C$_1$–C$_{10}$)-alkyl-S(O)$_2$, (C$_6$–C$_{14}$)-aryl-(C$_1$–C$_8$)-alkyl optionally substituted in the aryl radical, R$^9$NHS(O)$_2$ or the radical R$^{15}$;

R$^{12}$ is hydrogen, (C$_1$–C$_{18}$)-alkyl, (C$_2$–C$_8$)-alkenyl, (C$_2$–C$_8$)-alkynyl, optionally substituted (C$_6$–C$_{14}$)-aryl, (C$_1$–C$_{18}$)-alkoxy, (C$_6$–C$_{14}$)-aryl-(C$_1$–C$_8$)-alkoxy which can also be substituted in the aryl radical, optionally substituted (C$_6$–C$_{14}$)-aryloxy, the radical R$^{15}$, the radical R$^{15}$—O—, amino, mono- or di-((C$_1$–C$_{18}$)-alkyl)amino, (C$_2$–C$_8$)-alkenylamino, (C$_2$–C$_8$)-alkynylamino, (C$_3$–C$_{12}$)-cycloalkylamino, (C$_3$–C$_{12}$)-cycloalkyl-(C$_1$–C$_8$)-alkylamino, the radical R$^{15}$—NH—, optionally substituted (C$_6$–C$_{14}$)-aryl-NH, (C$_6$–C$_{14}$)-aryl-(C$_1$–C$_8$)-alkyl-NH, which can also be substituted in the aryl radical, optionally substituted heteroaryl-NH or heteroaryl-(C$_1$–C$_8$)-alkyl-NH optionally substituted in the heteroaryl radical;

R$^{12a}$ is amino, mono- or di-((C$_1$–C$_{18}$)-alkyl)-amino, (C$_2$–C$_8$)-alkenylamino, (C$_2$–C$_8$)-alkynylamino, (C$_3$–C$_{12}$)-cycloalkylamino, (C$_3$–C$_{12}$)-cycloalkyl-(C$_1$–C$_8$)-alkylamino, the radical R$^{15}$—NH—, optionally substituted (C$_6$–C$_{14}$)-aryl-NH, (C$_6$–C$_{14}$)-aryl-(C$_1$–C$_8$)-alkyl-NH, which can also be substituted in the aryl radical, optionally substituted heteroaryl-NH or heteroaryl-(C$_1$–C$_8$)-alkyl-NH optionally substituted in the heteroaryl radical;

R$^{13}$ is hydrogen, (C$_1$–C$_6$)-alkyl, (C$_6$–C$_{14}$)-aryl-(C$_1$–C$_8$)-alkyl optionally substituted in the aryl radical or (C$_3$–C$_8$)-cycloalkyl;

R$^{15}$ is R$^{16}$—(C$_1$–C$_6$)-alkyl or R$^{16}$;

R$^{16}$ is a 6- to 24-membered bicyclic or tricyclic radical which is saturated or partially unsaturated and which can also contain one to four identical or different heteroatoms from the group consisting of nitrogen, oxygen and sulfur and which can also be substituted by one or more identical or different substituents from the group consisting of $(C_1-C_4)$-alkyl and oxo;

$R^{21}$ is hydrogen, $(C_1-C_8)$-alkyl, $(C_3-C_{12})$-cycloalkyl, $(C_3-C_{12})$-cycloalkyl-$(C_1-C_8)$-alkyl, $(C_6-C_{14})$aryl, $(C_6-C_{14})$-aryl-$(C_1-C_8)$-alkyl, the radical Het- or Het-$(C_1-C_8)$-alkyl, where alkyl radicals can be monosubstituted or polysubstituted by fluorine and the radicals $R^{21}$ can be identical or different if they occur several times;

$R^{22}$ is $(C_3-C_{12})$-cycloalkyl, $(C_3-C_{12})$-cycloalkyl-$(C_1-C_8)$-alkyl, $(C_6-C_{14})$-aryl, the radical Het- or Het-$(C_1-C_8)$-alkyl, where alkyl radicals can be monosubstituted or polysubstituted by fluorine;

$R^{23}$ is $(C_1-C_8)$-alkyl, $(C_3-C_{12})$-cycloalkyl, $(C_3-C_{12})$-cycloalkyl-$(C_1-C_8)$-alkyl, $(C_6-C_{14})$-aryl, $(C_6-C_{14})$-aryl-$(C_1-C_8)$-alkyl, the radical Het- or Het-$(C_1-C_8)$-alkyl, where alkyl radicals can be monosubstituted or polysubstituted by fluorine;

$R^{24}$ $(C_3-C_{12})$-cycloalkyl, $(C_3-C_{12})$-cycloalkyl-$(C_1-C_8)$-alkyl, $(C_6-C_{14})$-aryl, $(C_6-C_{14})$-aryl-$(C_1-C_8)$-alkyl, the radical Het- or Het-$(C_1-C_8)$-alkyl, where alkyl radicals can be monosubstituted or polysubstituted by fluorine;

$R^{25}$ has the means of $R^{23}$, where the radicals $R^{25}$ can be identical or different;

$R^{26}$ has the meanings of $R^{21}$ or HO—$((C_1-C_8)$-alkyl), where alkyl radicals can be monosubstituted or polysubstituted by fluorine;

$R^{27}$ is hydrogen, $(C_3-C_{12})$-cycloalkyl, $(C_3-C_{12})$-cycloalkyl $(C_1-C_8)$-alkyl, $(C_6-C_{14})$-aryl-$(C_1-C_8)$-alkyl, the radical Het- or Het-$(C_1-C_8)$-alkyl, where alkyl radicals can be monosubstituted or polysubstituted by fluorine;

$R^{28}$ is one of the radicals $R^{21}$—, $R^{21}O$—, $R^{20}N(R^{20})$, $R^{21}C(O)$—, $R^{21}O$—$C(O)$—, $((C_1-C_{18})$-alkyl-O—$C(O)$—$((C_1-C_6)$-alkyl)-O—$C(O)$—, $R^{21}N(R^{21})$—$C(O)$—, $R^{21}N(R^{21})$—$C(=N(R^{21}))$— or $R^{21}C(O)$—$N(R^{21})$;

Het is a mono- or polycyclic, 4- to 14-membered, aromatic or nonaromatic ring which contains 1, 2, 3 or 4 identical or different heteroatoms from the group consisting of N, O and S as ring members and can optionally be substituted by one or more, identical or different substituents;

b, c, d and f independently of one another are 0 or 1, but cannot all simultaneously be 0;

e, g and h independently of one another are 1, 2, 3, 4, 5 or 6;

in all their stereoisomeric forms and mixtures thereof in any ratio, and/or of their physiologically tolerable salts together with one or more physiologically tolerable carriers and/or additives.

* * * * *